United States Patent
Fujimiya et al.

(10) Patent No.: US 10,512,660 B2
(45) Date of Patent: Dec. 24, 2019

(54) ACTIVATOR FOR MESENCHYMAL STEM CELLS, ACTIVATED MESENCHYMAL STEM CELLS, AND METHOD FOR PRODUCING SAME

(71) Applicant: Sapporo Medical University, Sapporo-shi (JP)

(72) Inventors: Mineko Fujimiya, Sapporo (JP); Kanna Nagaishi, Sapporo (JP); Yuka Mizue, Sapporo (JP); Takako Chikenji, Sapporo (JP)

(73) Assignee: Sapporo Medical University, Hokkaido (JP)

( * ) Notice: Subject to any disclaimer, the term of this patent is extended or adjusted under 35 U.S.C. 154(b) by 277 days.

(21) Appl. No.: 15/121,569

(22) PCT Filed: Mar. 11, 2015

(86) PCT No.: PCT/JP2015/057217
§ 371 (c)(1),
(2) Date: Oct. 20, 2016

(87) PCT Pub. No.: WO2015/137419
PCT Pub. Date: Sep. 17, 2015

(65) Prior Publication Data
US 2017/0071984 A1    Mar. 16, 2017

(30) Foreign Application Priority Data

Mar. 11, 2014 (JP) .................. 2014-048202

(51) Int. Cl.
*A61K 35/28* (2015.01)
*C12N 5/0775* (2010.01)

(52) U.S. Cl.
CPC ............ *A61K 35/28* (2013.01); *C12N 5/0663* (2013.01); *C12N 2500/84* (2013.01)

(58) Field of Classification Search
CPC ............ C12N 5/0663; C12N 2502/025; C12N 2500/84; A61K 35/28
See application file for complete search history.

(56) References Cited

U.S. PATENT DOCUMENTS

| | | | |
|---|---|---|---|
| 2005/0059152 A1 | 3/2005 | Tanavde et al. | |
| 2007/0178591 A1 | 8/2007 | Honmou et al. | |
| 2011/0076770 A1 | 3/2011 | Sakai et al. | |
| 2013/0072466 A1* | 3/2013 | Choi et al. | A61K 31/5685 514/181 |
| 2014/0295554 A1 | 10/2014 | Kim et al. | |

FOREIGN PATENT DOCUMENTS

| | | |
|---|---|---|
| EP | 2 308 964 A1 | 4/2011 |
| JP | 2001-072572 A | 3/2001 |
| JP | 2006-034111 A | 2/2006 |
| JP | 2006-325444 A | 12/2006 |
| JP | 2009-284819 A | 12/2009 |
| JP | 2011-067175 A | 4/2011 |
| JP | 2011-160799 A | 8/2011 |
| JP | 2013-018756 A | 1/2013 |
| JP | 2013-147479 A | 8/2013 |
| JP | 2013-155122 A | 8/2013 |
| WO | WO 2005/007176 A1 | 1/2005 |
| WO | WO 2011/087103 A1 | 7/2011 |
| WO | WO 2013/009100 A1 | 1/2013 |

OTHER PUBLICATIONS

Hao H. et al., "Culturing on Wharton's Jelly Extract Delays Mesenchymal Stem Cell Senescence through p53 and p16INK4a/pRb Pathways", PLoS ONE, Mar. 13, 2013, vol. 8, No. 3: e58314. doi:10.1371/journal.pone.0058314 (11 total pages). (Year: 2013).*
Kim S-M. et al. "Alternative Xeno-Free Biomaterials Derived from Human Umbilical Cord for the Self Renewal Ex-vivo Expansion of Mesenchymal Stem Cells", Stem Cells and Development, 2013, vol. 22, No. 22, pp. 3025-3038. (Year: 2013).*
Phadnis S.M. et al. "Mesenchymal Stem Cells Derived from Bone Marrow of Diabetic Patients Portrait Unique Markers Influenced by the Diabetic Microenvironment", The Review of Diabetic Studies, 2009, vol. 6, No. 4, pp. 260-270. (Year: 2009).*
Shin K.S. et al., "Culture and in vitro hepatogenic differentiation of placenta-derived stem cells, using placenta extract as an alternative to serum", Cell Proliferation, 2010, vol. 43, pp. 435-444. (Year: 2010).*
Kawakatsu et al., "Placental extract protects bone marrow-derived stem/progenitor cells against radiation injury through anti-inflammatory activity", Journal of Radiation Research, 2013, vol. 54, pp. 268-276. (Year: 2013).*
Djouad et al., Arthritis Rheum, 52(5):1595-1603 (2005).
Ezquer et al., Biol Blood Marrow Transplant, 14:631-40 (2008).
Fujimiya, Cardioangiology, 72(4):426-30 (2012).
Kim et al., Biol. Pharm. Bull., 33(6):1004-10 (2010).
Lee et al., PNAS, 103(46):17438-43 (2006).
Nagaishi et al., Regenerative Medicine, vol. 13, special extra issue, p. 330 (2014).
Ortiz et al., PNAS, 100(14):8407-11 (2003).
PCT/JP2015/057217 International Search Report issued by Japanese Patent Office dated Jun. 16, 2015.
Sobolewski et al., Placenta, 26:747-52 (2005).
Tanaka et al., J Gastroenterol, 46:143-52 (2011).
Watanabe et al., J Gastroenterol, 49:270-82 (2014).

(Continued)

*Primary Examiner* — Satyendra K Singh
(74) *Attorney, Agent, or Firm* — RatnerPrestia

(57) ABSTRACT

[Problem] To activate an abnormal mesenchymal stem cell whose therapeutic effect is lost or reduced, or rather which has a disease-exacerbating effect so as to be in a state suitable for cell transplant therapy.

[Solution] An activator for mesenchymal stem cells, mesenchymal stem cells activated by the activator, a method for producing the same, and a pharmaceutical containing the activated mesenchymal stem cells are provided.

20 Claims, 33 Drawing Sheets

Specification includes a Sequence Listing.

(56) References Cited

OTHER PUBLICATIONS

Zappia et al., Blood, 106(5):1755-61 (2005).
Extended European Search Report for Application No. 15 76 1691.3 dated Oct. 10, 2017.
Sun et al., Database Medline XP-002773912 (2007).
Klinkhammer et al., PLoS One (2014) 9 (3): e92115.
Carrion (Carrion et al, Lupus (2010) 19, 317-322).
Noh, et al., Nephrol Dial Transplant (2012) 27:218-225.
Stenderup et al., Bone (2003) 33:919-926.
Kim et al., BMC Cell Biology (2013) 14:38.
Ra et al., Journal of Translational Medicine (2011), 9:181.

\* cited by examiner

Bar 100μm

1; DM-MSC-WJ(−)

2-8; DM-MSC-WJ(+)

1; DM-MSC-WJ(−)

2-6; DM-MSC-WJ(+)

1 P
2 P+PM
3 PM

Bar 100μm

1  WJ(-)
2  WJ-#001(+)
3  WJ-#002(+)
4  P-#001(+)
5  P-#002(+)
6  PM-#001-Mince (+)
7  PM-#002-Thin strip (+)
8  PM-#002-Mince (+)

A.

B.

$P < 0.05$
1 STZ-DM-MSC-WJ v.s. STZ-DM-MSC
2 STZ-DM-MSC-WJ v.s. STZ-vehicle

A. Histological finding (PAS staining):glomerulus

B. Histological finding (PAS staining):renal tubule

C. Histological finding (Azan staining):glomerulus

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
atgggtgtga accacgagaa a                                              21

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
ggatacattg ggggtaggaa                                                20

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
tacttcaaca agcccacagg c                                              21

<210> SEQ ID NO 4
<211> LENGTH: 22
<212> TYPE: DNA
<213> ORGANISM: Artificial Sequence
<220> FEATURE:
<223> OTHER INFORMATION: PCR primer

<400> SEQUENCE: 4
tcagcggagc acagtacatc tc                                             22

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
tccctggaga agagctacga ac                                             22

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
ccaatgaaag atggctggaa g                                              21

<210> SEQ ID NO 7
<211> LENGTH: 22
<212> TYPE: DNA
<213> ORGANISM: Artificial Sequence

```
<220> FEATURE:
<223> OTHER INFORMATION: PCR primer

<400> SEQUENCE: 7
tgtacctggg aggagtcttc ca                                              22

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
cagtcgcttc acagagcaat g                                               21

<210> SEQ ID NO 9
<211> LENGTH: 24
<212> TYPE: DNA
<213> ORGANISM: Artificial Sequence
<220> FEATURE:
<223> OTHER INFORMATION: PCR primer

<400> SEQUENCE: 9
ctgacagacc ccaaaagatt aagg                                            24

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
cttgtcgaga tgctgctgtg a                                               21

<210> SEQ ID NO 11
<211> LENGTH: 21
<212> TYPE: DNA
<213> ORGANISM: Artificial Sequence
<220> FEATURE:
<223> OTHER INFORMATION: PCR primer

<400> SEQUENCE: 11
gccaaggcac actcattgaa a                                               21

<210> SEQ ID NO 12
<211> LENGTH: 24
<212> TYPE: DNA
<213> ORGANISM: Artificial Sequence
<220> FEATURE:
<223> OTHER INFORMATION: PCR primer

<400> SEQUENCE: 12
cttttgccag ttcctccaga tatc                                            24

<210> SEQ ID NO 13
<211> LENGTH: 22
<212> TYPE: DNA
<213> ORGANISM: Artificial Sequence
<220> FEATURE:
<223> OTHER INFORMATION: PCR primer

<400> SEQUENCE: 13
caggccacag aattgaaaca tc                                              22
```

```
<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
ccagcgtctt ccaagtgaaa g                                              21

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
tatggctcgg acaccactcc                                                20

<210> SEQ ID NO 16
<211> LENGTH: 22
<212> TYPE: DNA
<213> ORGANISM: Artificial Sequence
<220> FEATURE:
<223> OTHER INFORMATION: PCR primer

<400> SEQUENCE: 16
gacaaagacg actgcaaggt tg                                             22
```

ACTIVATOR FOR MESENCHYMAL STEM CELLS, ACTIVATED MESENCHYMAL STEM CELLS, AND METHOD FOR PRODUCING SAME

CROSS-REFERENCE TO RELATED APPLICATIONS

This application is a U.S. National Phase Application of PCT International Application PCT/JP2015/057217, filed Mar. 11, 2015 which claims priority to Japanese Application No. 2014-048202, filed Mar. 11, 2014, the contents of which are incorporated herein by reference in their entireties for all purposes.

TECHNICAL FIELD

The present invention relates to an activator for mesenchymal stem cells, mesenchymal stem cells activated by the activator, a method for producing the same, and a pharmaceutical containing the activated mesenchymal stem cells.

BACKGROUND OF THE INVENTION

Globally, the number of diabetic patients continuously increases. Various complications caused by chronic hyperglycemia due to diabetes threaten QOL and life of the patients, which has become a serious problem.

The so-called three major diabetic complications: diabetic nephropathy, diabetic retinopathy and diabetic neuropathy are developed due to organ damage caused by microangiopathy, which is a pathological change occurring in thin blood vessels, mainly capillaries. These complications can be prevented to a certain extent by appropriately controlling blood glucose with dietary therapy, drug therapy or the like. However, when the complications become serious, there is no fundamental therapy.

It is known that mesenchymal stem cells (hereinafter, also referred to as "MSCs") are cells capable of differentiating into not only mesenchymal cells but also diverse cells beyond the germ layer and have an ability of controlling the tissue development, repair and reproduction.

Since the isolation and cultivation of mesenchymal stem cells are easy and mesenchymal stem cells have a vigous proliferation potential, it is possible to ensure the number of transplantable cells in a short period. In addition, mesenchymal stem cells can be transplanted autologously with no immunological rejection, which causes few ethical problems. Furthermore, allogenic transplantation of mesenchymal stem cells without pretreatment is realistic because of their low immunogenicity. Accordingly, the therapeutic applications of mesenchymal stem cells as a material for ideal cell transplant therapy for diverse diseases are proceeding.

For example, the therapeutic effects of mesenchymal stem cells have been confirmed in diabetes and its complications described above (Non Patent Literatures 1 and 2) as well as diseases such as brain and cardiovascular disease (Patent Literature 1), autoimmune disease (Non Patent Literature 3), experimental autoimmune encephalomyelitis model of multiple sclerosis (Non Patent Literature 4), and inflammatory disease (refer to Non Patent Literature 5 on pulmonary fibrosis model, refer to Non Patent Literature 6 on inflammatory bowel disease).

When used for disease therapy, it is necessary to prepare mesenchymal stem cells with a certain level of quality rapidly and in a large amount. In order to allow the mesenchymal stem cells obtained from donors to proliferate in vitro, growth promoting substances, cell culture substrates and the like are variously examined. For example, Patent Literature 2 discloses that an umbilical cord extract can be used as a serum alternative on cultivation of stem cells in a serum free medium. Concerning the quality of cells, for example, Patent Literature 3 discloses a cell growth medium for suppressing senescence of mesenchymal stem cells during subculturing.

However, the umbilical cord extract disclosed in Patent Literature 2 is simply the serum alternative. The medium in Patent Literature 3 intends to maintain the quality or suppress the degree of deterioration of mesenchymal stem cells during in vitro proliferation, and does not improve or modify the quality of mesenchymal stem cells that are not appropriate for therapy, i.e. low quality mesenchymal stem cells.

CITATION LIST

Patent Literatures

Patent Literature 1: WO2005/007176
Patent Literature 2: WO2013/009100
Patent Literature 3: JP2006-325444 A

Non-Patent Literatures

Non-Patent Literature 1: Ezquer, F. E. et al., Biol Blood Marrow Transplant, 2008; 14 (6): 631-40
Non-Patent Literature 2: Lee, R. H. et al., Proc Natl Acad Sci USA, 2006; 103 (46): 17438-43
Non-Patent Literature 3: Djouad, F. et al., Arthritis Rheum, 2005; 52(5): 1595-1603
Non-Patent Literature 4: Zappia E. et al., Blood 2005; 106: 1755-1761
Non-Patent Literature 5: Ortiz, A. L. et al., Proc Natl Acad Sci USA, 2003; 100 (14): 8407-8411
Non-Patent Literature 6: Tanaka H. et al., J Gastroenterol, 2011; 46:143-152

SUMMARY OF THE INVENTION

Technical Problem

The present inventors have found that mesenchymal stem cells obtained from subjects developing diabetes or rheumatoid arthritis have inferior therapeutic effects on diabetes and its complications and rheumatoid arthritis to those of mesenchymal stem cells derived from healthy subjects, or rather have effects of exacerbating these diseases.

This finding indicates that autologous transplant therapy with mesenchymal stem cells obtained from subjects developing diabetes or rheumatoid arthritis, especially the subjects in severe condition, does not have an expectable effect. Therefore, it is necessary for effective autologous transplant therapy to previously obtain autologous mesenchymal stem cells before the onset or before the mesenchymal stem cells become abnormal and the therapeutic effects are lost. However, mesenchymal stem cell collection is invasive and becomes a large burden on a healthy person physically and economically. Additionally, in the case of diseases progressing with few subjective symptoms in the early phase, such as diabetes, mesenchymal stem cells have already become abnormal at diagnosis. Consequently, there is a possibility that the autologous transplant therapy cannot be applied due to the above-described reasons.

Therefore, an object of the present invention is to activate an abnormal mesenchymal stem cell whose therapeutic effect is lost or reduced, or rather which has a disease-exacerbating effect so as to be in a state suitable for cell transplant therapy.

Solution to Problem

The present inventors have found that an extract from mammalian fetal appendage activates abnormal mesenchymal stem cells and have completed the following inventions:

(1) An activator for abnormal mesenchymal stem cell, including an extract from mammalian fetal appendage as an active ingredient;

(2) The activator according to (1), wherein the fetal appendage is an umbilical cord tissue, a placental tissue or a placental membrane;

(3) The activator according to (1) or (2), wherein the extract does not contain cells that are derived from the mammal and have proliferation potency;

(4) The activator according to any one of (1) to (3), wherein the abnormal mesenchymal stem cell is a bone-marrow-derived mesenchymal stem cell;

(5) The activator according to any one of (1) to (4), wherein the abnormal mesenchymal stem cell is separated from a subject with a disease;

(6) The activator according to (5), wherein the disease is diabetes, an autoimmune disease, a chronic inflammatory disease, an allergic disease or osteoporosis;

(7) The activator according to (5), wherein the disease is diabetes or rheumatoid arthritis;

(8) A method for producing an activated mesenchymal stem cell including:
treating an abnormal mesenchymal stem cell separated from a subject with an activator that includes an extract from mammalian fetal appendage as an active ingredient;

(9) The method for producing a mesenchymal stem cell according to (8), wherein the abnormal mesenchymal stem cell is a bone-marrow-derived mesenchymal stem cell;

(10) The method for producing a mesenchymal stem cell according to (8) or (9), wherein the subject is a subject with a disease;

(11) The method for producing a mesenchymal stem cell according to (10), wherein the disease is diabetes, an autoimmune disease, a chronic inflammatory disease, an allergic disease or osteoporosis;

(12) The method for producing a mesenchymal stem cell according to (10), wherein the disease is diabetes or rheumatoid arthritis;

(13) A mesenchymal stem cell for the treatment and/or prevention of a disease, wherein the cell is produced by the method according to any one of (8) to (12);

(14) The mesenchymal stem cell according to (13), wherein the disease is diabetes or its complications, an autoimmune disease, a chronic inflammatory disease, an allergic disease or osteoporosis;

(15) The mesenchymal stem cell according to (13), wherein the disease is diabetic nephropathy, diabetic retinopathy, diabetic neuropathy or rheumatoid arthritis; and

(16) A pharmaceutical for the treatment and/or prevention of a disease including the mesenchymal stem cell according to any one of (13) to (15) and/or its culture.

Advantageous Effects of Invention

According to the present invention, it is possible to activate an abnormal mesenchymal stem cell obtained from a subject so as to be in a state suitable for cell transplant therapy. Accordingly, it enables the autologous transplant therapy to be applied to patients who were unsuitable for the autologous cell transplant therapy because of the abnormalization of the autologous mesenchymal stem cells. The activator of the present invention does not contain cells that are derived from a fetal appendage donor mammal and have proliferation potency. Therefore, it is not necessary to remove the cells derived from the donor after the activation treatment, which is advantageous in that an extra cell processing step is not accompanied.

Figure 13:
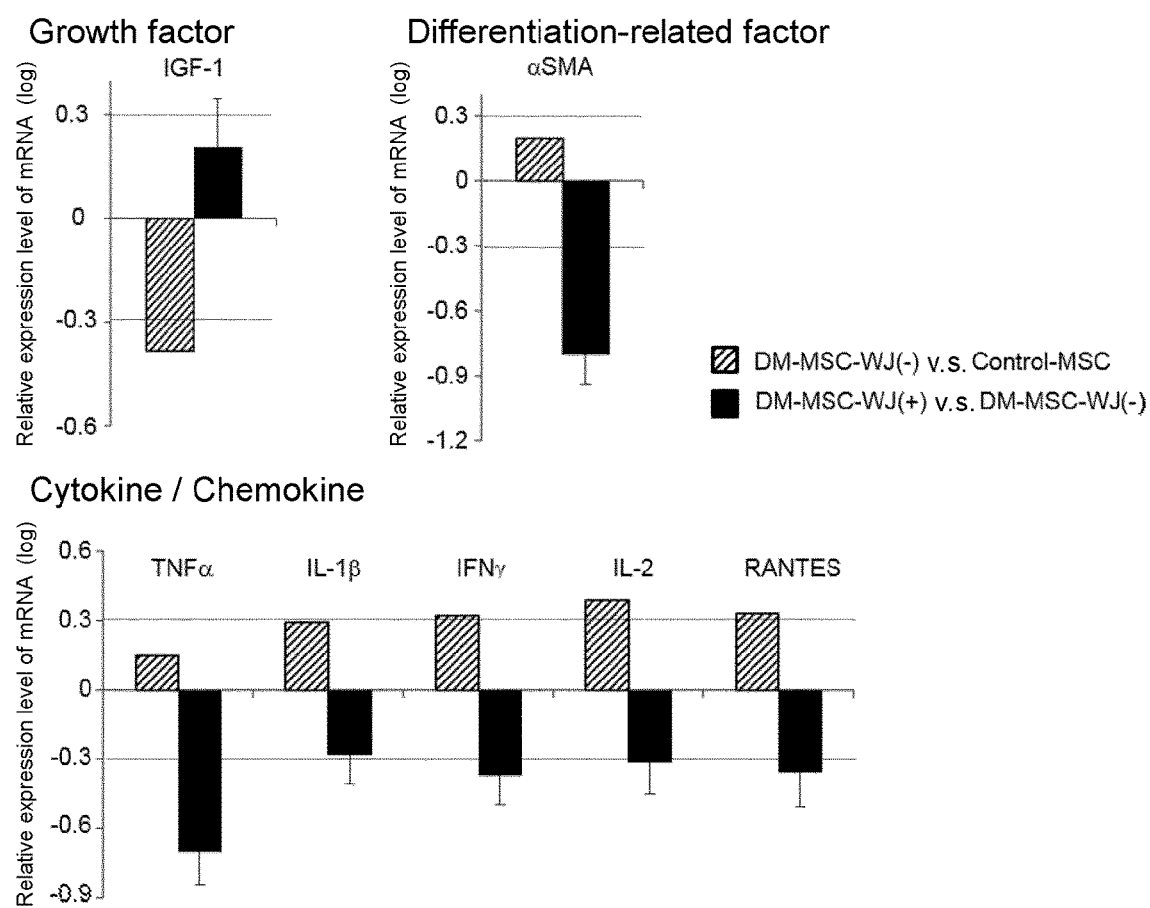
Figure 14:
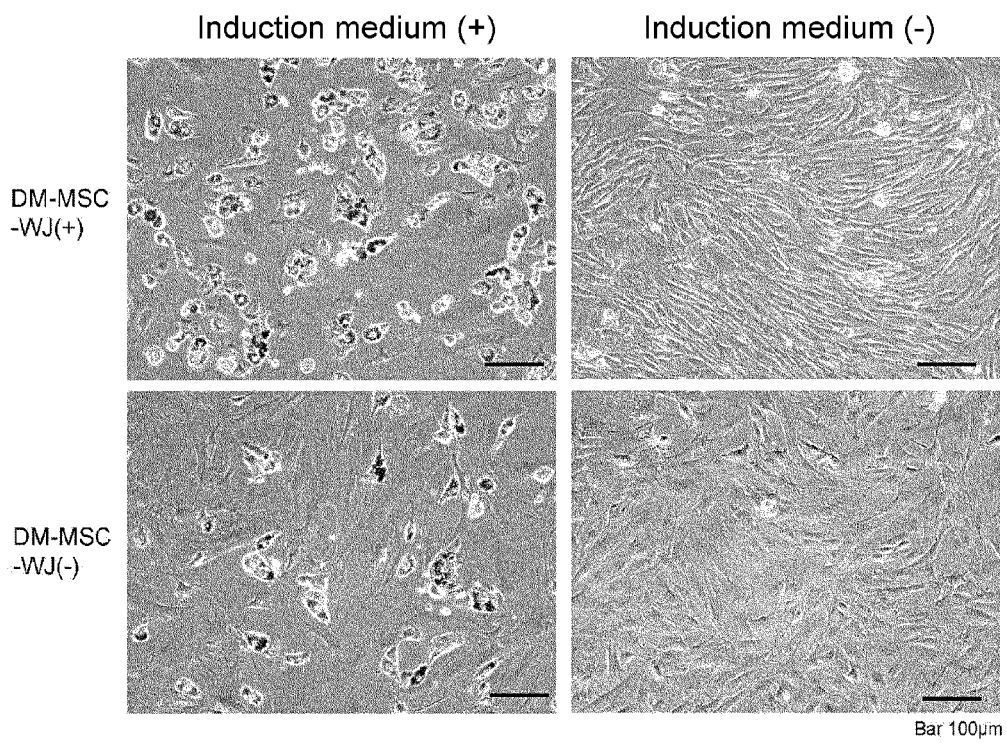
Figure 15:
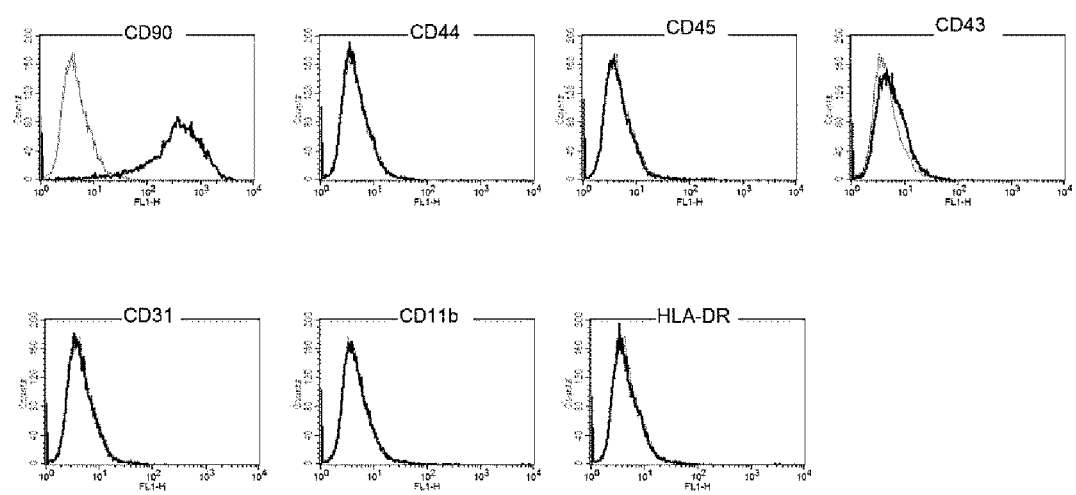
Figure 21:
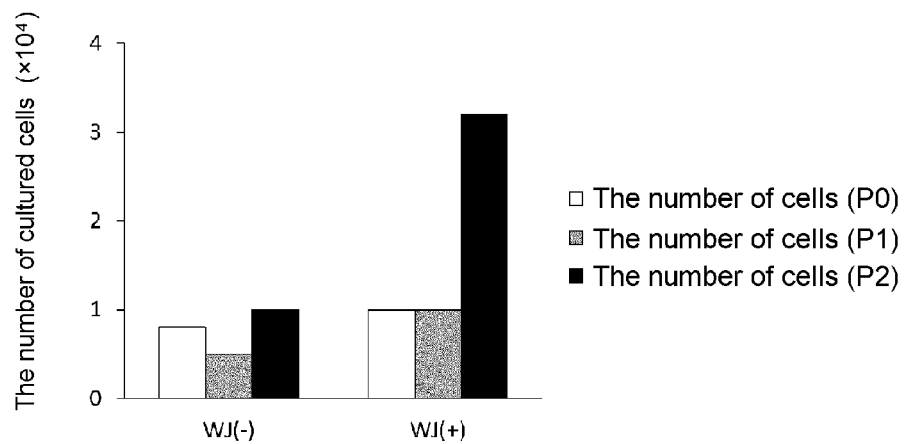
Figure 23:
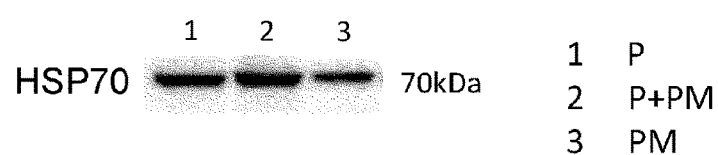
Figure 24:
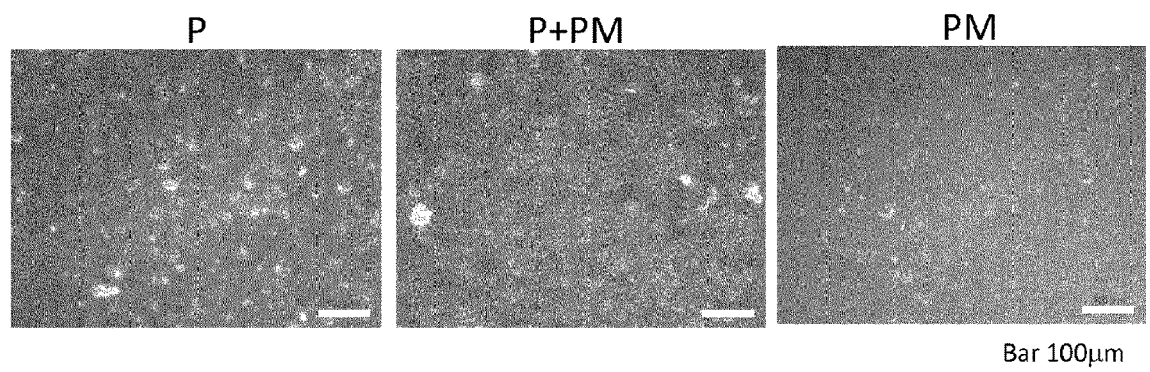
Figure 25:
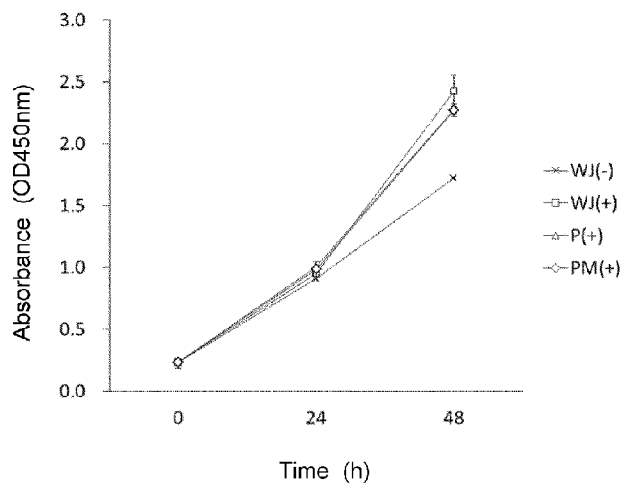
Figure 25:
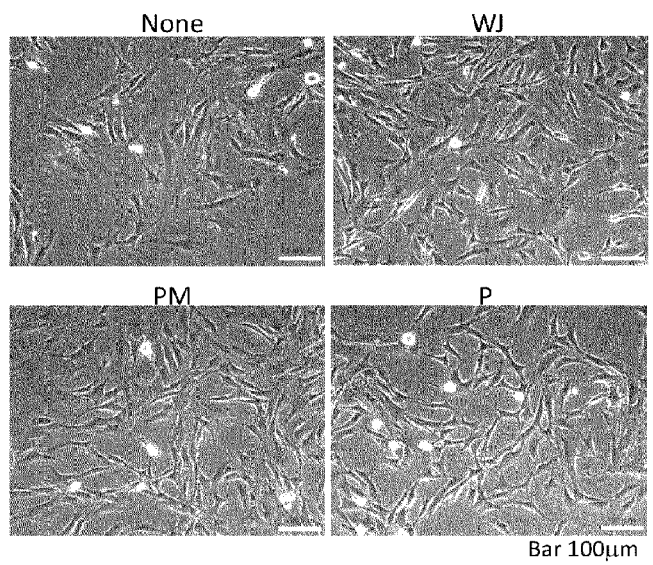
Figure 25:
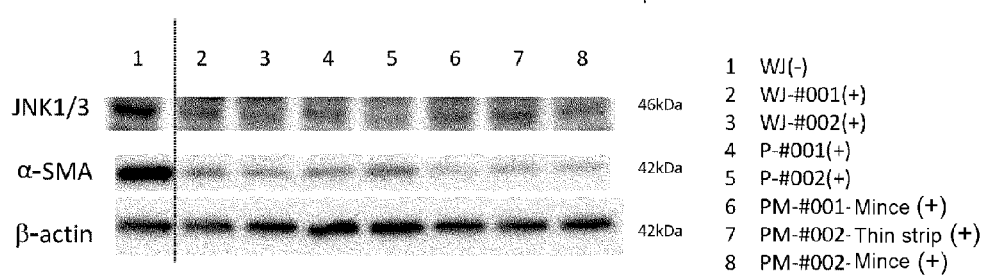
Figure 30:
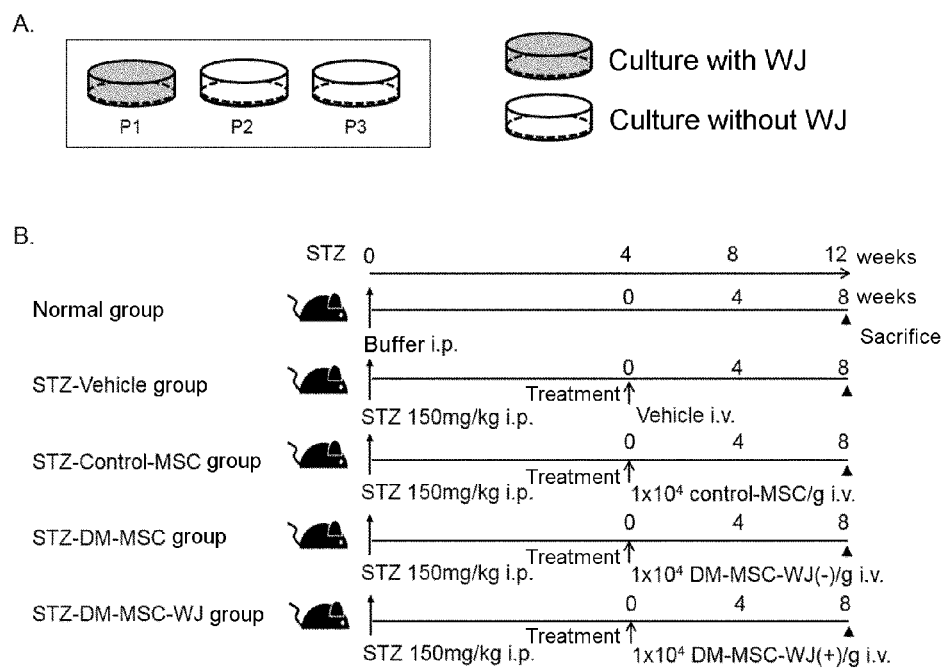
Figure 31:
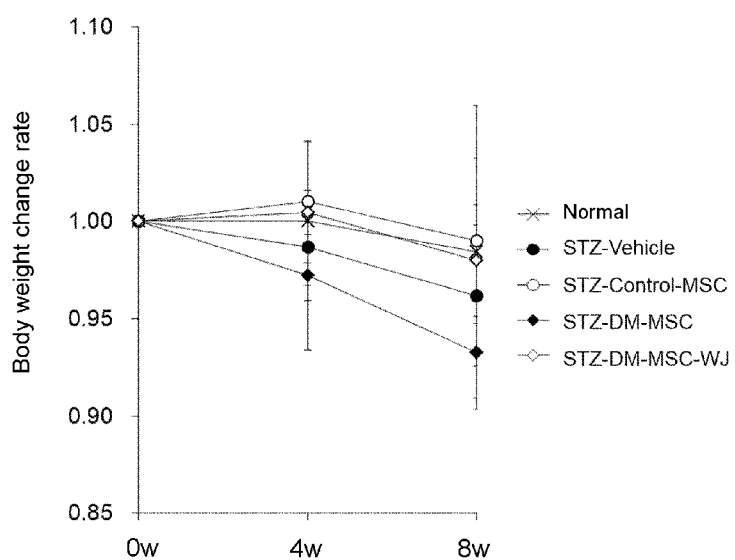
Figure 32:
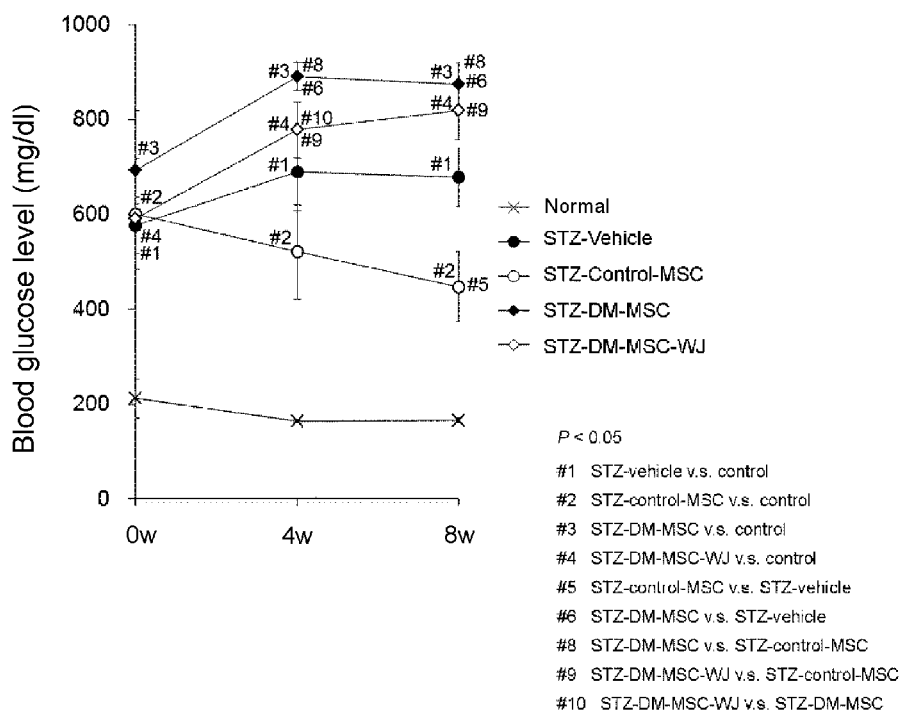
Figure 33:
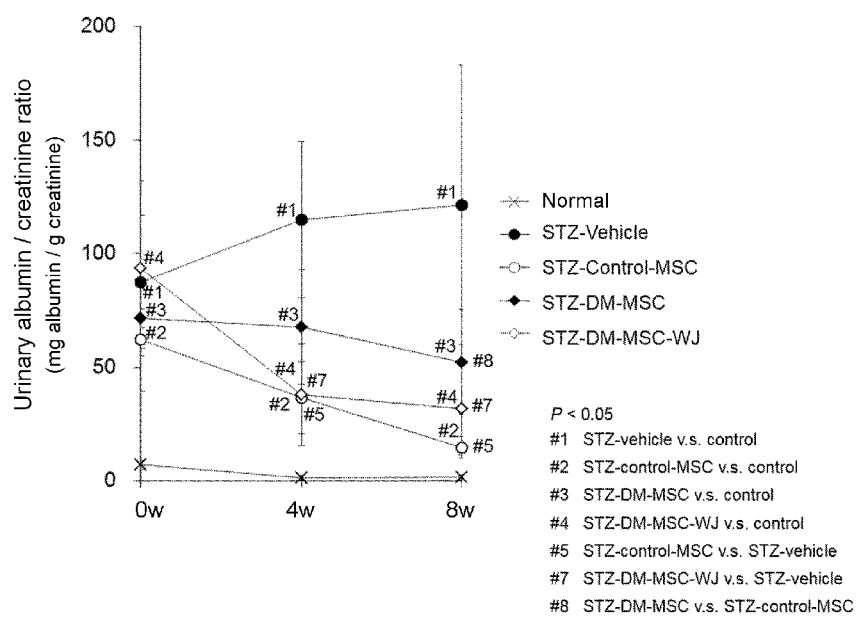
Figure 34:
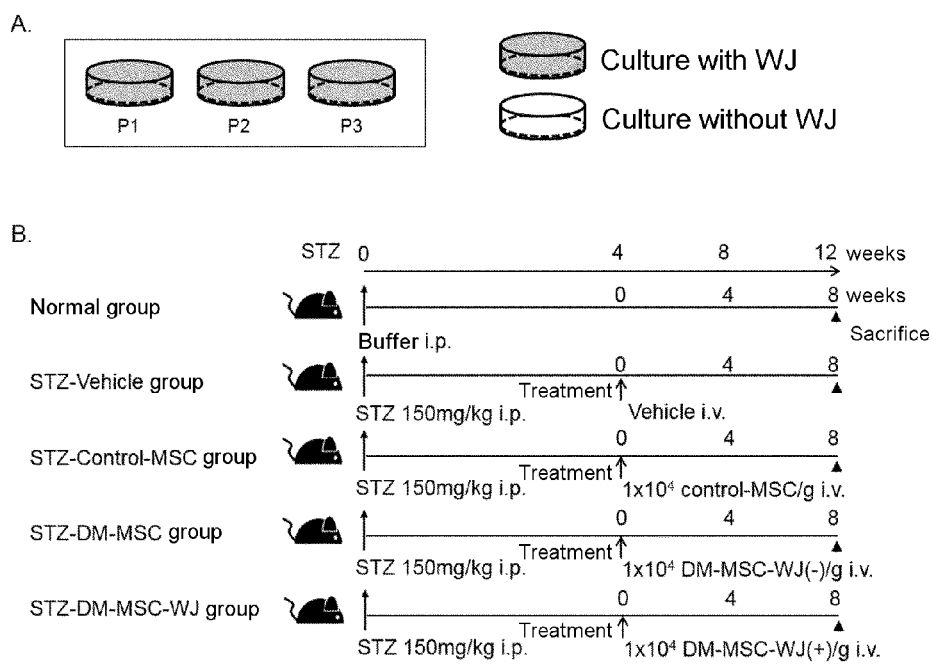
Figure 35:
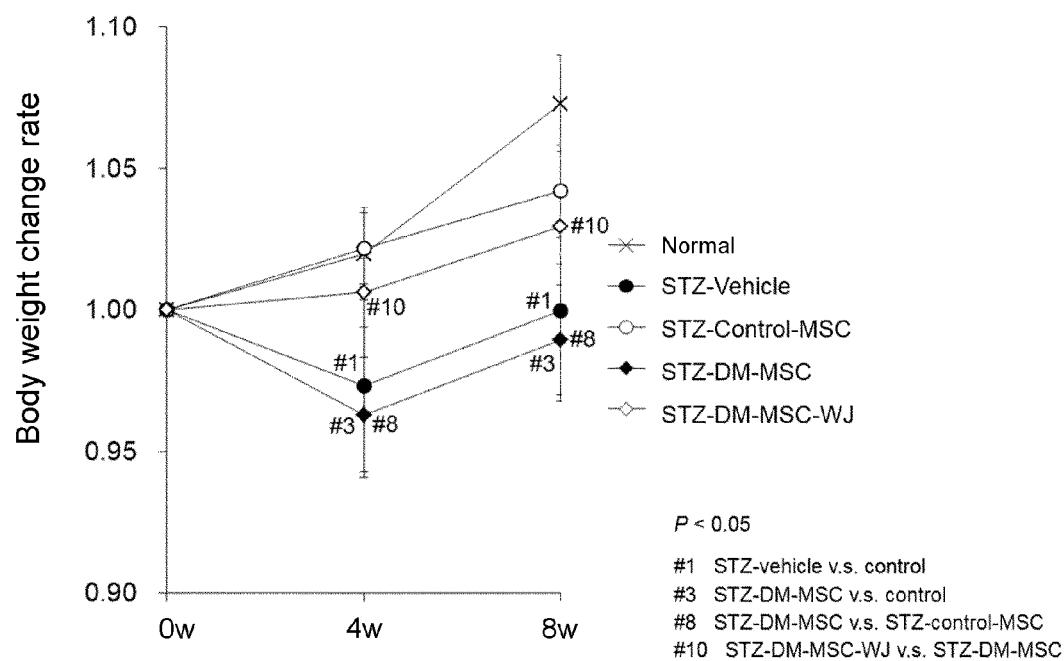
Figure 36:
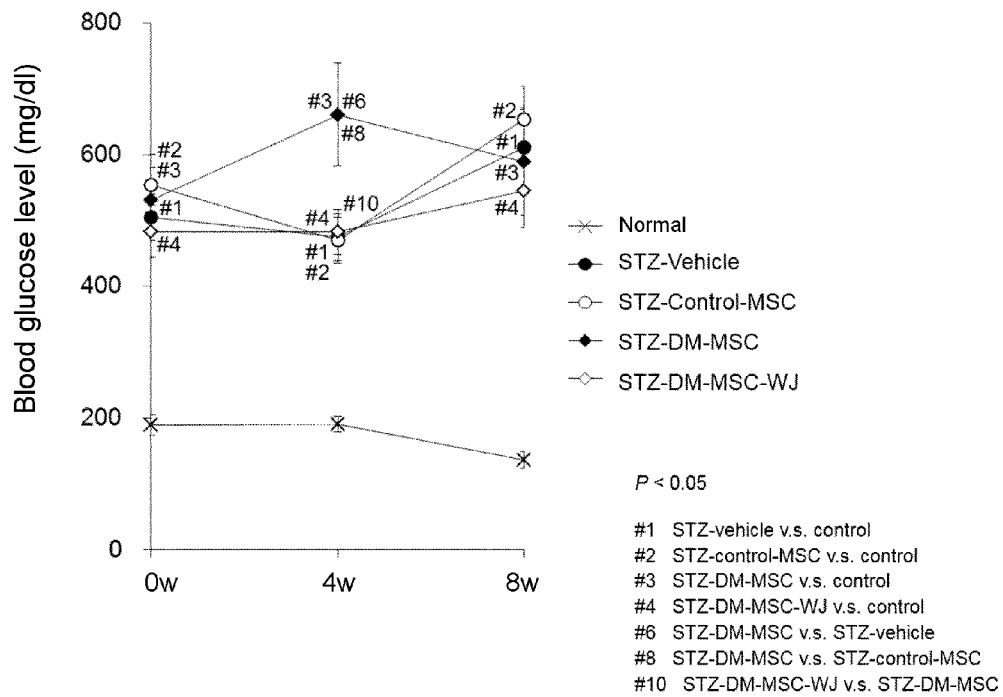
Figure 37:
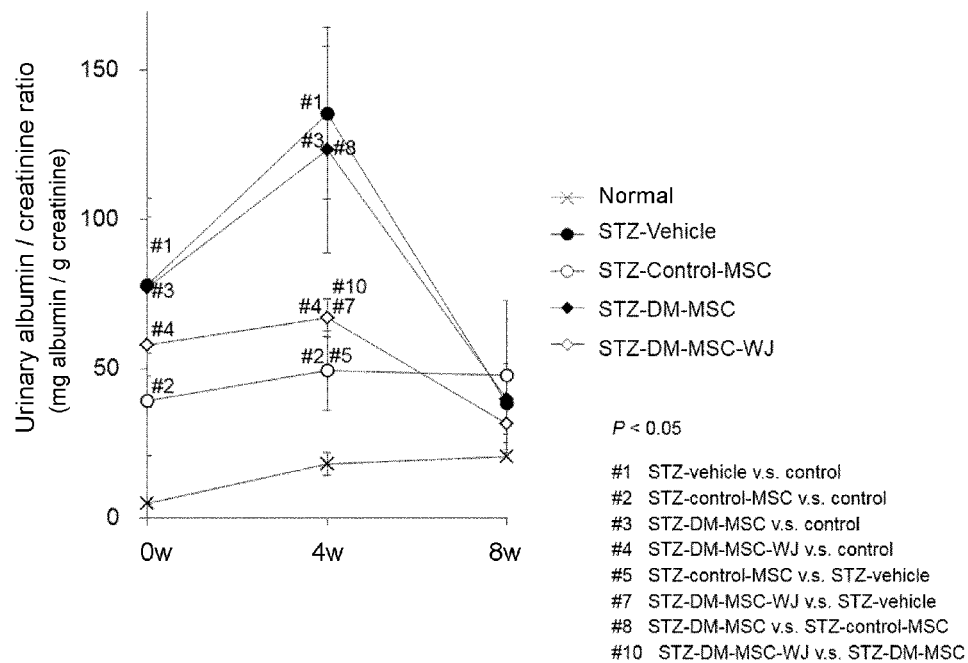
Figure 38:
Figure 38:
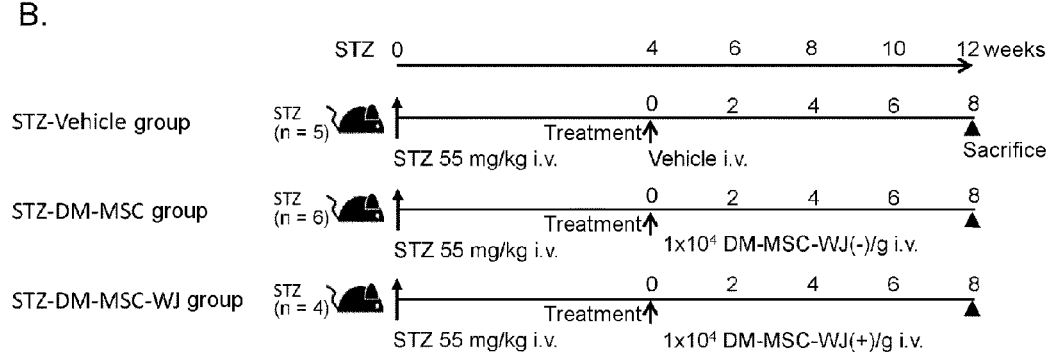
Figure 39:
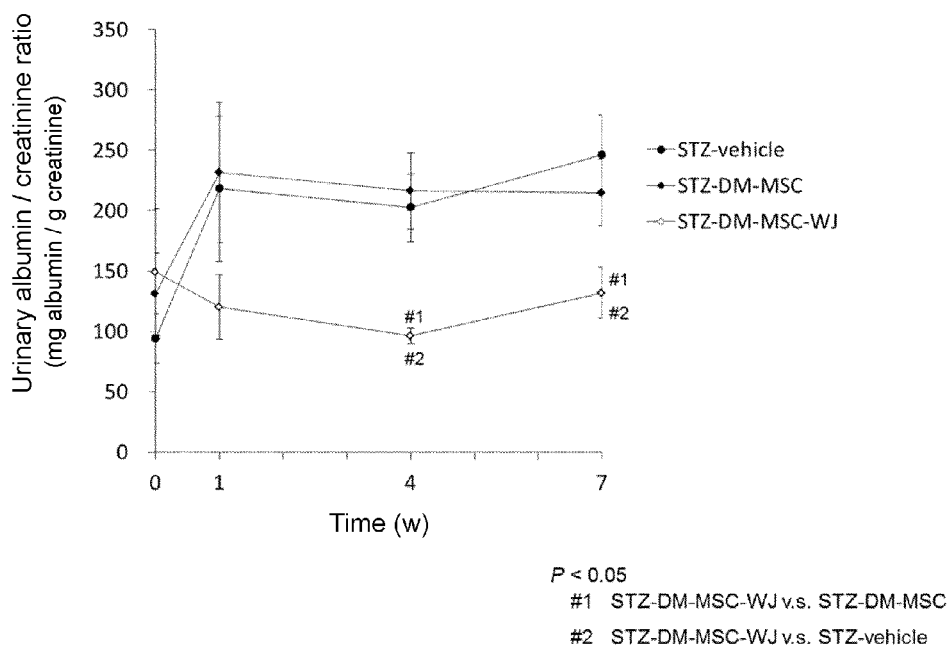
Figure 40:
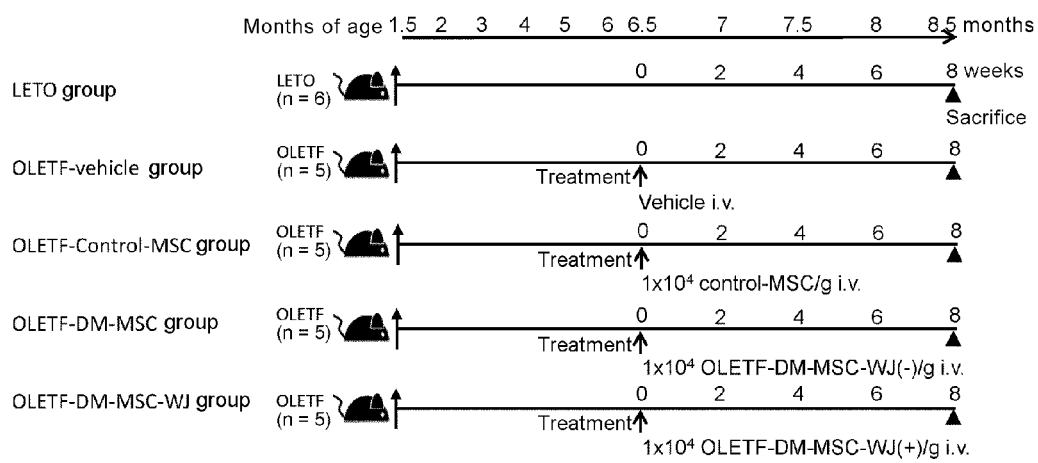
Figure 41:
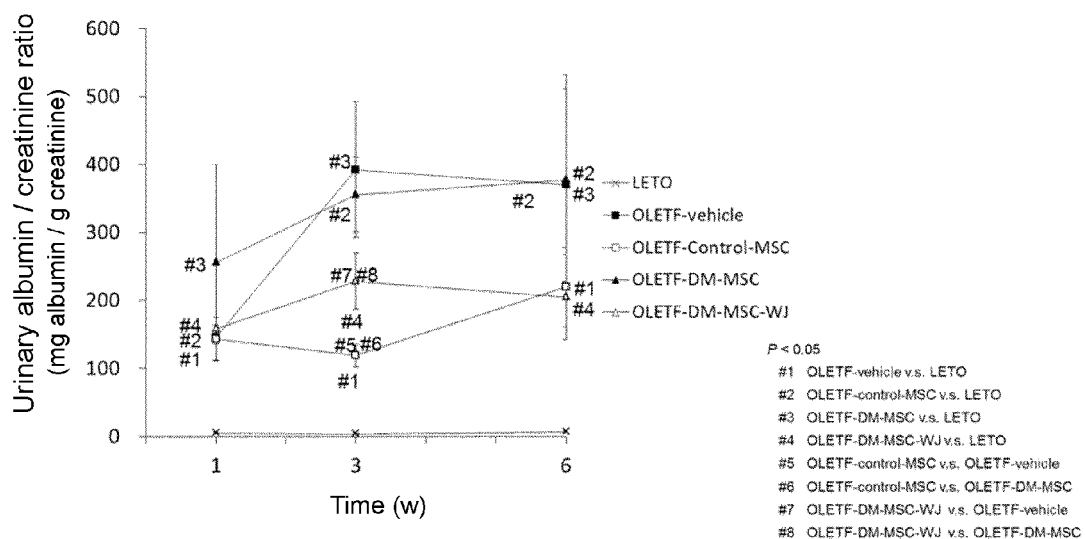
Figure 42:
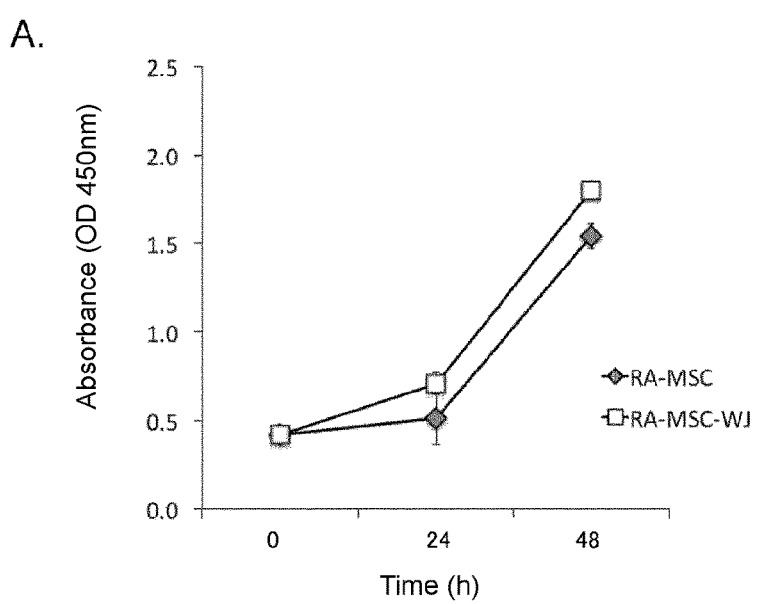
Figure 42:
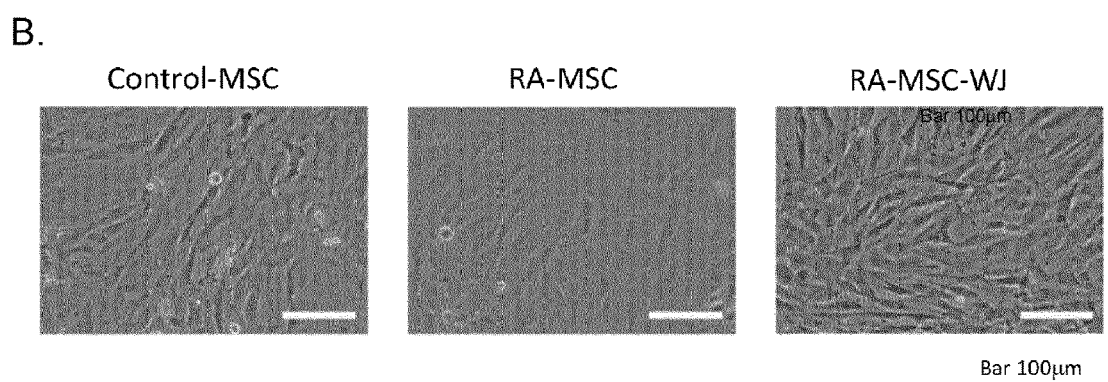
Figure 43:
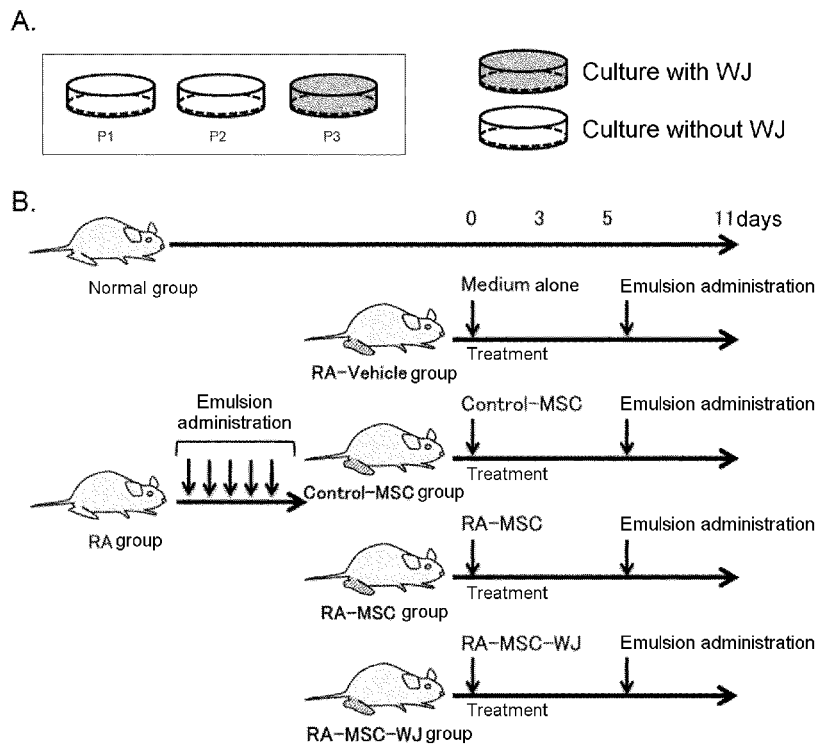
Figure 44:
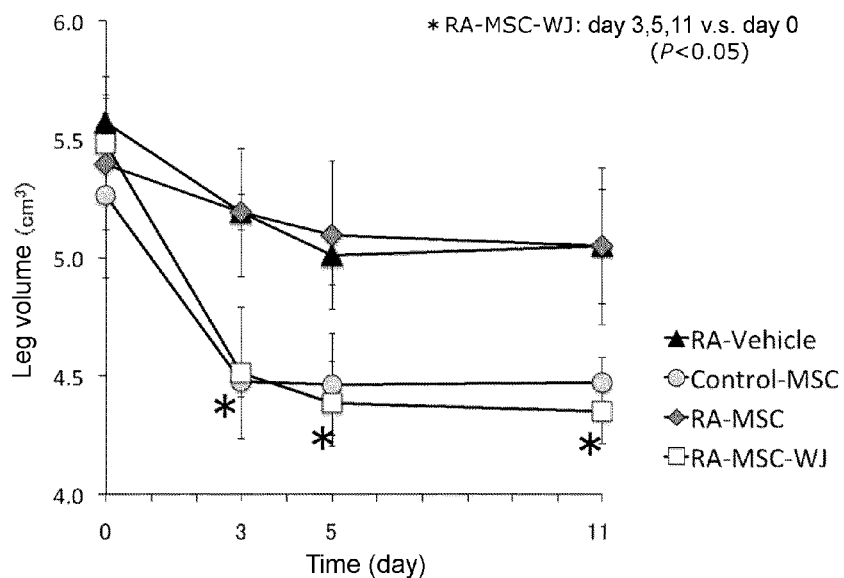
Figure 45:
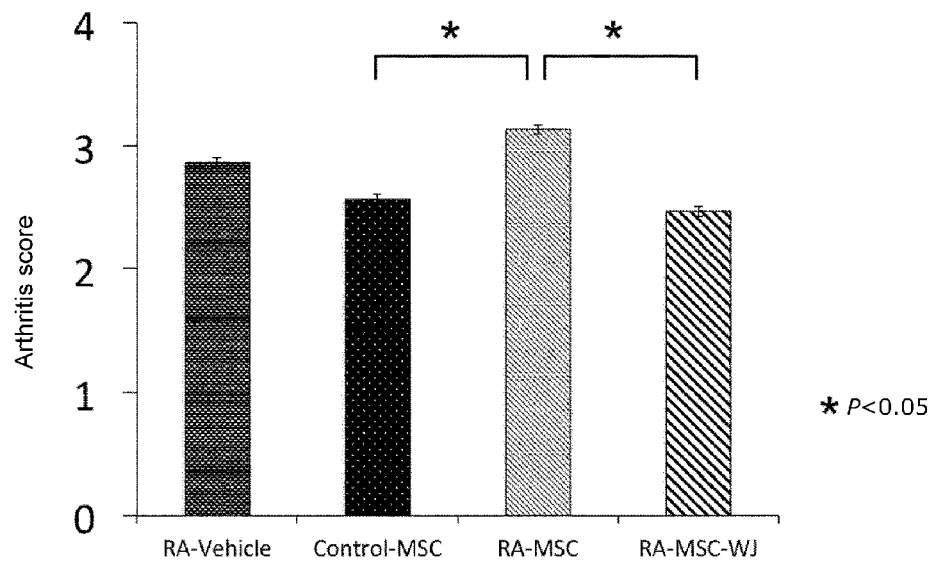
Figure 46:
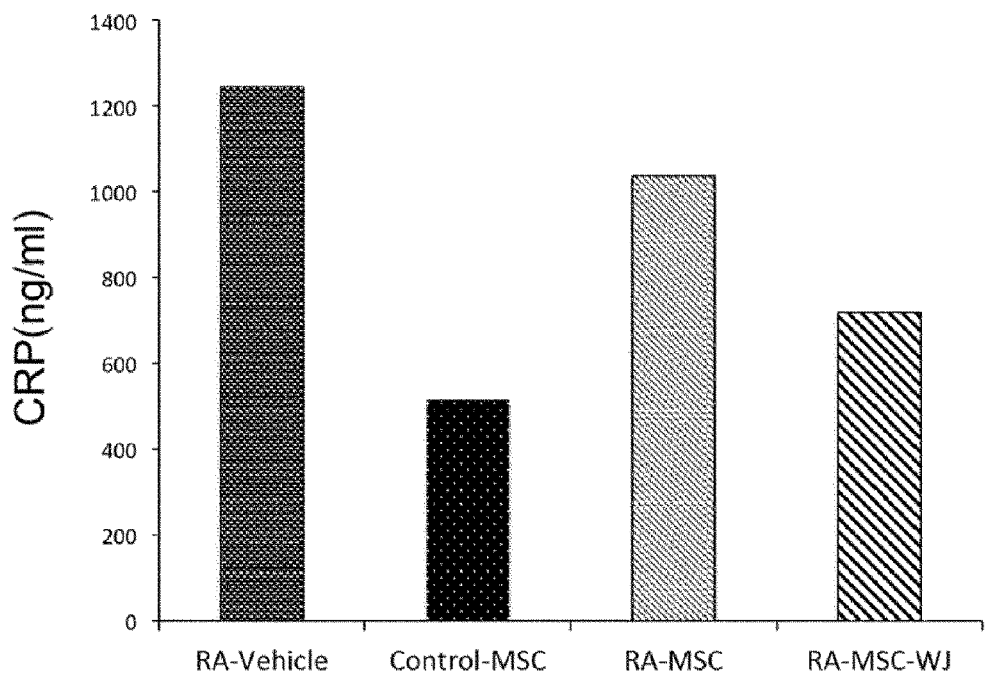

FIG. 13 is a graph showing the ratio of gene expression level of the growth factor, differentiation-related factor and cytokine/chemokine in Control-MSCs, DM-MSCs-WJ (−) and DM-MSCs-WJ (+), wherein each slash bar indicates the gene expression level in DM-MSCs-WJ (−)/the gene expression level in Control-MSCs and each black bar indicates the gene expression level in DM-MSCs-WJ (+)/the gene expression level in DM-MSCs-WJ (−);

FIG. 14 shows bright field microscopy images showing the differentiation of DM-MSCs-WJ (−) and DM-MSCs-WJ (+) into adipocytes;

FIG. 15 shows the results of flow cytometry analysis on the expression of the surface antigens in DM-MSCs-WJ (+), wherein dashed lines correspond to isotype control and solid lines correspond to target antibodies;

FIG. 16A shows the results of MTT assays and FIG. 16B shows phase contrast microscopy images of mesenchymal stem cells from STZ-induced type I diabetes model rats wherein the cells were subjected to the activation treatment with umbilical cord tissue extracts; the characters on the photographs of FIG. 16B indicate concentrations (mg/mL) of the umbilical cord tissue extracts in the activation treatment;

FIG. 17A shows the results of MTT assays and FIG. 17B shows phase contrast microscopy images of mesenchymal stem cells from OLETF Type II diabetes model rats wherein the cells were subjected to the activation treatment with umbilical cord tissue extracts; the characters on the photographs of FIG. 17B indicate concentrations (mg/mL) of the umbilical cord tissue extracts in the activation treatment;

FIG. 18A shows the results of MTT assays and FIG. 18B shows phase contrast microscopy images of mesenchymal stem cells from STZ-induced type I diabetes model rats wherein the cells were subjected to the activation treatment with various concentration of the umbilical cord tissue extracts and with or without fetal bovine serum (FBS), and FIG. 18C shows Western blotting analysis on the expression of JNK1/3 and α-SMA proteins in the mesenchymal stem cells; the characters on the photographs of FIG. 18B indicate concentrations (mg/mL) of the umbilical cord tissue extracts in the activation treatment;

FIG. 19A shows the results of MTT assays and FIG. 19B shows phase contrast microscopy images of mesenchymal stem cells from OLETF Type II diabetes model rats wherein the cells were subjected to the activation treatment with various concentration of the umbilical cord tissue extracts and with or without FBS, and FIG. 19C shows Western blotting analysis on the expression of JNK1/3 and α-SMA proteins in the mesenchymal stem cells; the characters on the photographs of FIG. 19B indicate concentrations (mg/mL) of the umbilical cord tissue extracts in the activation treatment;

FIG. 20A shows the results of MTT assays and FIG. 20B shows phase contrast microscopy images of mesenchymal stem cells derived from patients with type II diabetes wherein the cells were subjected to the activation treatment with various concentration of the umbilical cord tissue extracts and with or without FBS; the characters on the photographs of FIG. 20B indicate concentrations (mg/mL) of the umbilical cord tissue extracts in the activation treatment;

FIG. 21 is a graph showing the total number of cells in each passages obtained by culturing the bone marrow fluid of patients with type II diabetes with the umbilical cord tissue extracts at the concentration of 1.0 mg/mL in the presence of FBS;

FIG. 22A shows the results of MTT assays and FIG. 22B shows phase contrast microscopy images of mesenchymal stem cells derived from a patient with type I diabetes wherein the cells were subjected to the activation treatment with the umbilical cord tissue extract; the characters on photographs of FIG. 22B indicate whether the umbilical cord tissue extract is added in the activation treatment and the lower photograph shows mesenchymal stem cells from a healthy individual;

FIG. 23 shows Western blotting of exosome fractions with anti-HSP70 antibodies, wherein the exosome fractions were prepared from a placental tissue extract (P) and a placental membrane extract (PM), which are another examples of extract from fetal appendage;

FIG. 24 shows images of culture of placental tissue extracts and placental membrane extracts;

FIG. 25A shows the results of MTT assays and FIG. 25B shows phase contrast microscopy images of mesenchymal stem cells from STZ-induced type I diabetes model rats wherein the cells were subjected to the activation treatment with the placental tissue extract or the placental membrane extract, and FIG. 25C shows Western blotting analysis on the expression of JNK1/3 and α-SMA proteins in the mesenchymal stem cells;

FIG. 26A shows the results of MTT assays, FIG. 26B shows phase contrast microscopy images, and FIG. 26C shows electron microscopy images of DM-MSCs-WJ (−) cultured in a medium with or without L-Glutamate;

FIG. 27A shows the results of MTT assays, FIG. 27B shows phase contrast microscopy images, and FIG. 27C shows electron microscopy images of DM-MSCs-WJ (−) cultured in a medium with or without hyaluronic acid or in a medium with an umbilical cord tissue extract in which hyaluronic acid is digested or in a medium with an umbilical cord tissue extract in which hyaluronic acid is not digested;

FIG. 28A shows the results of MTT assays, FIG. 28B shows phase contrast microscopy images, FIG. 28C shows electron microscopy images and FIG. 28D shows Western blotting analysis on the expression of JNK1/3 and α-SMA proteins of DM-MSCs-WJ (−) cultured in a medium with an umbilical cord tissue extract or exosome fractions of the extract;

FIG. 29A shows the results of MTT assays, FIG. 29B shows phase contrast microscopy images and FIG. 29C shows Western blotting analysis on the expression of JNK1/3 and α-SMA proteins of DM-MSCs-WJ (−) cultured in a medium with a placenta tissue extract or exosome fractions of the extract;

FIG. 30A is a view showing the activation protocol of DM-MSCs-WJ (+) for use in the evaluation of therapeutic effects on STZ-induced type I diabetic nephropathy model mice (STZ mice) (9-1. of Example 9) and FIG. 30B is a view showing therapeutic trial plans;

FIG. 31 is a graph showing the body weight change rate in the therapeutic trial for STZ mice (9-1. of Example 9);

FIG. 32 is a graph showing the blood glucose level in the therapeutic trial for STZ mice (9-1. of Example 9);

FIG. 33 is a graph showing the urinary albumin/creatinine ratio in the therapeutic trial for STZ mice (9-1. of Example 9);

FIG. 34A is a view showing the activation protocol of DM-MSCs-WJ (+) for use in the evaluation of therapeutic effects on STZ mice (9-2. of Example 9), and FIG. 34B is a view showing therapeutic trial plans;

FIG. 35 is a graph showing the body weight change rate in the therapeutic trial for STZ mice (9-2. of Example 9);

FIG. 36 is a graph showing the blood glucose level in the therapeutic trial for STZ mice (9-2. of Example 9);

FIG. 37 is a graph showing the urinary albumin/creatinine ratio in the therapeutic trial for STZ mice (9-2. of Example 9);

FIG. 38A is a view showing the activation protocol of DM-MSCs-WJ (+) for use in the evaluation of therapeutic effects on STZ-induced type I diabetic nephropathy model rats (STZ rats) (10-1. of Example 10) and FIG. 38B is a view showing therapeutic trial plans;

FIG. 39 is a graph showing the urinary albumin/creatinine ratio in the therapeutic trial for STZ rats (10-1. of Example 10);

FIG. 40A is a view showing the activation protocol of mesenchymal stem cells from OLETF Type II diabetes model rats (OLETF-DM-MSCs-WJ (+)) for use in the evaluation of therapeutic effects on OLETF type II diabetic nephropathy model rats (OLETF rats) (10-2. of Example 10) and FIG. 40B is a view showing therapeutic trial plans;

FIG. 41 is a graph showing the urinary albumin/creatinine ratio in the therapeutic trial for OLETF rats (10-2. of Example 10);

FIG. 42A shows the results of MTT assays and FIG. 42B shows phase contrast microscopy images of mesenchymal stem cells from rheumatoid arthritis model rats (RA rats) (RA-MSCs-WJ) wherein the cells were subjected to the activation treatment with the umbilical cord tissue extract and mesenchymal stem cells from RA rats (RA-MSCs) wherein the cells were not subjected to the activation treatment;

FIG. 43A is a view showing the activation protocol of mesenchymal stem cells from RA rats for use in the evaluation of therapeutic effects on RA rats (11-3. of Example 11) and FIG. 43B is a view showing therapeutic trial plans;

FIG. 44 is a graph showing leg volumes in the therapeutic trial for RA rats;

FIG. 45 is a graph showing arthritis scores in the therapeutic trial for RA rats;

FIG. 46 is a graph showing serum CRP levels in the therapeutic trial for RA rats;

FIG. 47A is a view showing therapeutic trial plans of Control-MSCs and

Figure 49:
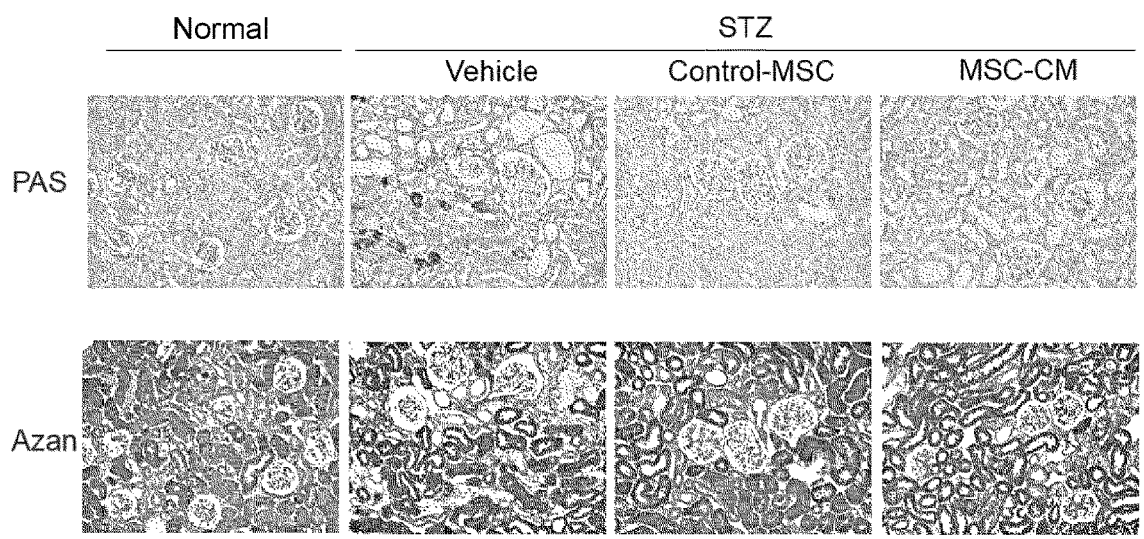

FIG. 47B is a view showing therapeutic trial plans of the culture supernatant of the MSCs (MSC-CM) for STZ mice (1-1. of Reference example 1);

FIG. 48A is a graph showing the urinary albumin/creatinine ratio in the therapeutic trial of Control-MSCs and FIG. 48B is a graph showing the urinary albumin/creatinine ratio in the therapeutic trial of MSC-CM for STZ mice (1-1. of Reference example 1);

FIG. 49 shows images of PAS- and Azan-stained kidney tissue sections in therapeutic trials of Control-MSCs and MSC-CM for STZ mice (1-1. of Reference example 1);

FIG. 50A is a view showing therapeutic trial plans of Control-MSCs and

Figure 51:
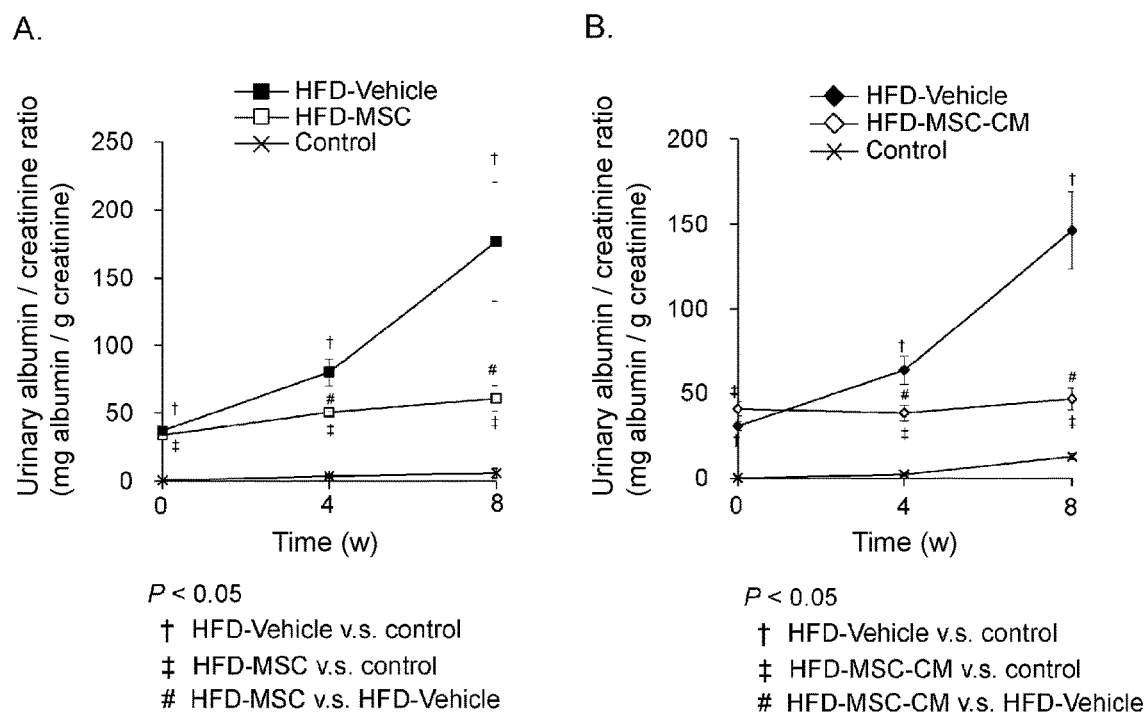
Figure 52:
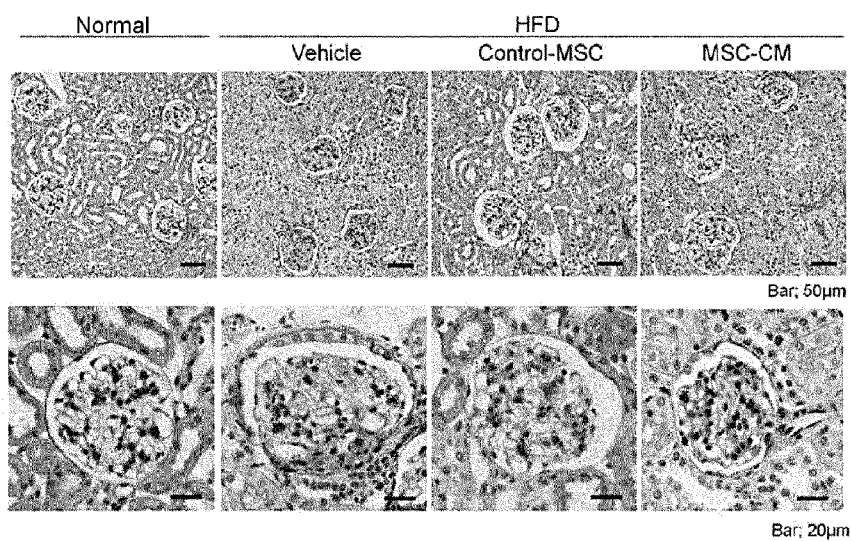
Figure 52:
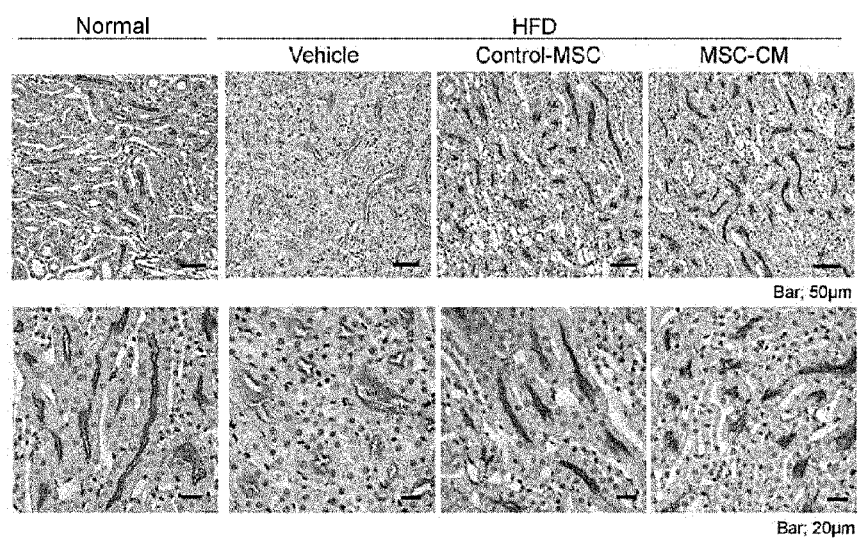
Figure 52:
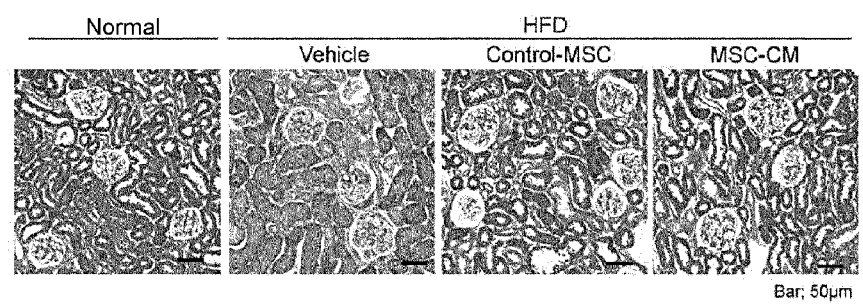

FIG. 50B is a view showing therapeutic trial plans of MSC-CM for high fat diet-induced type II diabetic nephropathy model mice (HFD mice) (1-2. of Reference example 1);

FIG. 51A is a graph showing the urinary albumin/creatinine ratio in the therapeutic trial of Control-MSCs and FIG. 51B is a graph showing the urinary albumin/creatinine ratio in the therapeutic trial of MSC-CM for HFD mice (1-2. of Reference example 1); and FIG. 52 shows images of PAS- and Azan-stained kidney tissue sections in therapeutic trials of Control-MSCs and MSC-CM for HFD mice (1-2. of Reference example 1).

DETAILED DESCRIPTION OF THE INVENTION

A first embodiment of the present invention relates to an activator for abnormal mesenchymal stem cell, including an extract from mammalian fetal appendage as an active ingredient. Furthermore, a second embodiment of the present invention relates to a method for producing an activated mesenchymal stem cell including: treating an abnormal mesenchymal stem cell separated from a subject with the activator of the first embodiment.

Extract

The fetal appendage is an organ that is formed in the uterus during pregnancy and plays a role in supporting the developing fetus, and is composed of the placenta, umbilical cord, placental membrane (consisting of three layers: amnion, chorion and decidua) and amniotic fluid. The placenta is a chorionic tissue serving as a place where substances are exchanged between fetus and mother, contains various growth factors and cytokines, and produces hormones. The umbilical cord is an organ that connects fetus to placenta and is composed of two umbilical arteries and one umbilical vein, Wharton's jelly, a connective tissue called umbilical cord stroma, and an amniotic sheath covering the periphery thereof.

The Wharton's jelly contains a small number of cells and an extracellular matrix such as collagen, glycosaminoglycan and mucin. The glycosaminoglycan in the Wharton's jelly mainly includes hyaluronic acid and also includes sulfated glycosaminoglycan such as keratan sulfate, chondroitin-6-sulfate and heparan sulfate.

It is also known that Wharton's jelly contains growth factors such as Insulin-like Growth Factor-1 (IGF-1), Platelet-Derived Growth Factor (PDGF), Epidermal Growth Factor (EGF) and Fibroblast Growth Factor (FGF) (K. Sobolewski et al., Placenta (2005), 26, 747-752).

The fetal appendage used in the present invention is ejected from a mother body as an afterbirth or taken out from a mother body by cesarean section. The extract of the present invention can be prepared from the whole fetal appendage obtained from a mother body. Alternatively, apart of a fetal appendage, namely, one or more organs or tissues of the fetal appendage may be used as an extraction material. In this case, from the viewpoint of activation activity and extraction efficiency, the extraction material preferably includes an umbilical cord tissue, a placental tissue or a placental membrane. The fetal appendage may be used to prepare an extract immediately after being obtained or it may be used after storage under refrigeration or freezing in a sterile container in order to avoid contamination.

The fetal appendage can be obtained from a mammal. In one of the preferred embodiments of the present invention, the fetal appendage is obtained from a human. It is also possible to use fetal appendages obtained from animals other than the human (for example, primates such as chimpanzees, rodents such as mice, rats, guinea pigs and hamsters, Artiodactyla, such as cows, goats, sheep and pigs, and Perissodactyla such as horses; and rabbits, dogs and cats).

Taking the safety in the subsequent cell transplant therapy into consideration, it is preferable that the fetal appendages are obtained from individuals whose species is identical or related to the species of the individuals to which mesenchymal stem cells are to be administered.

The extract used in the present invention can be prepared by extracting from the fetal appendages obtained as described above with an extraction medium. The fetal appendage is preferably used for extraction after rinsing unwanted components attached thereto with physiological saline or the like.

The rinsed fetal appendage may be used for extraction in the form as it is and is preferably used after being cut or crushed in order to improve the extraction efficiency. For example, the frozen fetal appendage is crushed with a mixer so that the extraction is achieved by a simpler operation. In one of the preferred embodiments of the present invention, when using an umbilical cord tissue, as described below, an umbilical cord tissue substantially maintaining its three-dimensional structure is used for extraction, which is obtained by appropriately cutting the umbilical cord tissue.

The term "umbilical cord tissue substantially maintaining its three-dimensional structure" used herein means an umbilical cord tissue obtained by cutting the umbilical cord tissue into a shape or size suitable for extraction using a scalpel, scissors, tweezers and other cutting devices or manually, without treatments to crush or uniformize the tissue (e.g., homogenization treatment).

If the three-dimensional structure of the umbilical cord tissue is crushed by homogenization or the like and the tissue is extracted, the extract may be foamed, the amount of the viscous component attached to an instrument, a container or the like may increase and thus the extraction efficiency may be reduced. The umbilical cord tissue is cut so as to substantially maintain its three-dimensional structure, whereby efficient extraction of the active ingredient is achieved simultaneously with the prevention of undesired foam formation.

The cutting direction is not limited as long as the three-dimensional structure of the umbilical cord tissue is maintained. Because of the structure of the umbilical cord tissue, it is preferable to cut the tissue along the longitudinal direction of the umbilical cord.

The extraction medium used in the present invention may be any medium generally used in the field of biochemistry as long as it has no negative influence on the activity of the active ingredient contained in the fetal appendage. An aqueous medium is preferred. An aqueous medium commonly used for cell culture and preparation is more preferred. Examples thereof include distilled water, physiological saline, phosphate buffered saline and media commonly used for cell culture such as α-MEM and DMEM.

Taking the safety of the subsequent cell transplant therapy into consideration, it is preferable that the extraction medium does not contain any components which may have an inconvenient influence on recipient individuals.

In one of the preferred embodiments of the present invention, the activation of a mesenchymal stem cell is performed by culturing the mesenchymal stem cell using an extract itself as a medium. In this case, as an extraction medium, those skilled in the art may appropriately select the cell culture medium which can sufficiently extract an active ingredient in a fetal appendage and is suitable for mesenchymal stem cell cultivation.

The extraction is performed by immersing a fetal appendage in an extraction medium and leaving to stand or shaking at 2° C. to 25° C., preferably at 2° C. to 8° C., more preferably at 4° C. for 24 hours to 144 hours, preferably for 48 hours to 96 hours, more preferably for 72 hours. The shaking rate is set to the level where the liquid during extraction is not excessively foamed. The amount of the extraction medium to be used is from 0.2 mL to 100 mL, preferably from 0.5 mL to 20 mL, and more preferably from 1 mL to 10 mL, per 1 g of wet weight of the fetal appendage. This amount is appropriately adjusted depending on the extent of cutting of the fetal appendage, the extraction temperature, the shaking rate or the like.

The extract liquid containing the fetal appendage after extraction can be used with removal of unnecessary solids derived from the fetal appendage by recovering the supernatant fraction obtained after leaving to stand or centrifugation or by recovering the filtrate after filtration.

The fetal appendage after extraction is reusable as long as the active ingredient is extracted. In other words, it is possible to obtain further extract by adding an extraction medium again to the fetal appendage after extraction of the active ingredient and performing the extraction treatment. The extraction is thus performed a plurality of times so that the yield of the active ingredient can be improved.

The extract thus obtained can be used in the form of liquid as it is. Alternatively, the extract may be concentrated or dried so as not to impair the activity of the active ingredient contained in the extract, and the concentrated or dried extract may be used with diluting or dissolving in an appropriate liquid at the time of use. Furthermore, the extract may be used immediately after preparation or may be used after storage under refrigeration or freezing.

In one of the preferred embodiments of the present invention, the extract does not contain cells that are derived from a fetal appendage donor mammal and have proliferation potency. This is because when the cells that are derived from the donor and have proliferation potency are contaminated, the target mesenchymal stem cells as well as the donor-derived cells may increase during the activation treatment, and the use of these cells for the cell transplant therapy may cause undesirable effects, such as rejection and graft versus host disease on recipient individuals.

Such extract without the cells having proliferation potency can be obtained by, for example, subjecting the fetal appendage to the cell killing treatment such as radiation exposure. Such extract can also be obtained without the cell removal treatment, by the above extraction method using the umbilical cord tissue substantially maintaining its three-dimensional structure.

The presence of the cells having proliferation potency in the extract can be confirmed by any known method for evaluating the cellular proliferative potency and survival rate, e.g., by a cell culture assay using an appropriate growth medium or a biochemical assay such as MTT assay.

Mesenchymal Stem Cells

Mesenchymal stem cells are stem cells with pluripotency and self-replication potency which are present in a trace amount in stromal cells in the mesenchyme tissue, and differentiate into not only cells belonging to the mesenchyme such as osteoblasts, chondrocytes, adipocytes and myocytes, but also neurons, hepatocytes or the like beyond the germ layer. Furthermore, mesenchymal stem cells are known to have a paracrine effect due to humoral factors produced by themselves and a cellular adhesive interaction.

It is assumed that mesenchymal stem cells exert a capability of repairing and regenerating target tissues and cells as well as an immunoregulation capability such as an anti-inflammatory capability based on these effects, thereby providing therapies for various diseases.

The term "abnormal mesenchymal stem cell" used in the present invention means a mesenchymal stem cell in which the above diverse capabilities are lost, or these capabilities are reduced, compared with those of a normal mesenchymal stem cell, and thus the therapeutic effect is lost or the therapeutic effect is reduced, compared with that of the normal mesenchymal stem cell. Furthermore, the present inventors have confirmed that the abnormal mesenchymal stem cell does not have the therapeutic effect or rather has the effect of exacerbating the disease. Such mesenchymal stem cell having the disease-exacerbating effect is also included in the term "abnormal mesenchymal stem cell" used in the present invention.

The present inventors have revealed that the mesenchymal stem cells obtained from individuals with diabetes or rheumatoid arthritis are abnormalized. It is assumed that such abnormalization also occurs in individuals with diseases such as an autoimmune disease, a chronic inflammatory disease and an allergic disease or in aged individuals. Furthermore, it is assumed that the abnormalization of the mesenchymal stem cells may occur in healthy individuals, and the abnormal cells from healthy individuals can be activated by the present invention.

Specific examples of disease in which mesenchymal stem cells are abnormalized include type I diabetes and type II diabetes; autoimmune diseases such as rheumatoid arthritis, systemic lupus erythematosus, Sjögren's syndrome, polymyositis, dermatomyositis, scleroderma, hyperthyroidism, hypothyroidism, autoimmune adrenal dysfunction, pure red cell anemia, multiple sclerosis and autoimmune hepatitis; chronic inflammatory diseases such as chronic hepatitis, hepatic cirrhosis, chronic obstructive pulmonary disease, Crohn's disease, ulcerative colitis and Behcet's disease; allergic diseases such as atopic dermatitis and bronchial asthma; and osteoporosis.

The abnormal mesenchymal stem cell used in the present invention is obtained from a subject. The term "subject" used herein means any animal having mesenchymal stem cells and is preferably an individual of mammals (e.g., primates such as humans or chimpanzees, rodents such as mice, rats, guinea pigs and hamsters, Artiodactyla, such as cows, goats, sheep and pigs, and Perissodactyla such as horses); and rabbits, dogs and cats, and is more preferably an individual of humans.

In one of the embodiments of the present invention, the subject is an individual with the above-described disease in which mesenchymal stem cells are abnormalized or an aged individual. In another embodiment, the disease is preferably diabetes, an autoimmune disease, a chronic inflammatory disease, an allergic disease or osteoporosis, and more preferably diabetes or rheumatoid arthritis.

Taking the safety in the subsequent cell transplant therapy into consideration, it is preferable that the mesenchymal stem cells are obtained from individuals whose species is identical or related to the species of the individuals to which the cells are administered. For example, when human individuals are subjected to cell transplantation, it is preferable to use cells collected from humans of the same species and it is more preferable to use cells collected from the same human individuals to undergo administration, i.e., autologous mesenchymal stem cells.

The mesenchymal stem cells can be obtained from a sample, such as mammalian bone marrow fluid, adipose tissue, tissue from the fetal appendage, and dental pulp, by a general method. For example, when using the bone marrow fluid as the sample, the mesenchymal stem cells can be separated by any known procedure, such as density gradient centrifugation or bone marrow seeding.

The abnormal mesenchymal stem cell may be subcultured in vitro after being obtained from a living body.

In one of the preferred embodiments of the present invention, a bone-marrow-derived cell is used as the abnormal mesenchymal stem cell.

Determination of whether the obtained mesenchymal stem cell is normal or abnormal can be performed by evaluating the therapeutic effect of the cell using an evaluation system reflecting the disease, such as a disease model animal or a disease model animal-derived cell.

The disease used as the evaluation system for abnormality determination may be a disease that can be treated by the normal mesenchymal stem cell. When the obtained mesenchymal stem cell after the activation is planned to be used for therapy, it is preferable to use an evaluation system for the disease identical or related to the disease planned to be treated. For example, when the mesenchymal stem cell is planned to be used in therapy for diabetic nephropathy, the abnormality evaluation of the obtained mesenchymal stem cell is preferably performed with an evaluation system reflecting diabetic nephropathy.

When the obtained mesenchymal stem cell has no therapeutic effect or has a therapeutic effect lower than that of the normal mesenchymal stem cell or when the obtained mesenchymal stem cell has a disease-exacerbating effect, the mesenchymal stem cell can be determined to be abnormal.

As in the following test examples, the abnormality of the mesenchymal stem cell can be determined using an evaluation indicator such as morphology of cells and intracellular organelles, cellular proliferative potency, differentiation potency, levels of the protein expression, gene expression and extracellular secretion of various factors including growth factors, differentiation-related factors and cytokines/chemokines.

As an example, the abnormal mesenchymal stem cell has the following properties different from those of the normal mesenchymal stem cell.

TABLE 1

| | |
|---|---|
| Morphology of cells | Flat fibroblast-like cells with a few projections and wide cell body |
| Morphology of intracellular organelle | Expansion and degeneration of endoplasmic reticulum, a reduction in the number of mitochondria and degeneration of mitochondria such as swelling of cristae, abnormality of autophagy, an increase in the amount of stress fibers |
| Cellular proliferative potency | Low |
| Differentiation potency | The differentiation potency of bone is low |
| Expression levels of proteins or genes in various molecules | An increase in α-smooth muscle actin (SMA), tumor necrosis factor (TNF)-α, interleukin (IL)-1β, interferon (INF)-γ, IL-2, Regulated on activation, normal T cell expressed and secreted (RANTES) or c-Jun N terminal kinase (JNK) ⅓; a decrease in IGF-1 |

These evaluations can be performed by any method commonly used in the fields of cell biology and molecular biology. Specifically, the morphology ofcellsandintracellularorganellescanbeevaluatedbymicroscopyobservation, the cellular proliferative potency can be evaluated by the cell culture assay using an appropriate growth medium or biochemical assay such as MTT assay, the differentiation potency can be evaluated by the differentiation-inducing assay using an appropriate differentiation-inducing medium, the protein expression can be evaluated by protein quantification such as ELISA and Western blotting, and the gene expression can be evaluated by gene quantification such as quantitative PCR and Northern blotting.

When one or more evaluation indicators as described above of the obtained mesenchymal stem cell has a different behavior from that of a normal mesenchymal stem cell, the mesenchymal stem cell can be determined to be abnormal.

Activator of Present Invention and Method for Producing Activated Mesenchymal Stem Cell The activator of the present invention can activate an abnormal mesenchymal stem cell.

The term "activate" used herein means making the abnormal mesenchymal stem cell to regain at least some of the diverse capabilities and to be in a state where the cells can exert a disease therapeutic effect. The abnormal mesenchymal stem cell is activated, whereby it exerts a therapeutic effect equivalent to or stronger than that of the normal mesenchymal stem cell. Furthermore, the term "activate" of the present invention includes making the abnormal mesenchymal stem cell to have an improved therapeutic effect compared with the cells before activation, although the therapeutic effect does not reach the same level as that of the normal mesenchymal stem cell.

The activator of the present invention contains an extract from mammalian fetal appendage as an active ingredient. As for the activator, the extract obtained by the above method can be used as it is or after dilution with an aqueous medium commonly used for cell culture and preparation. Examples of the aqueous medium used for dilution include distilled water, physiological saline and phosphate buffered saline; and culture media commonly used in cell culture such as α-MEM and DMEM.

Furthermore, the present invention relates to a method for producing an activated mesenchymal stem cell including: treating an abnormal mesenchymal stem cell separated from a subject with an activator that includes an extract from mammalian fetal appendage as an active ingredient.

The step of treating the mesenchymal stem cell with the activator, i.e. the activation step, is performed by adding the activator of the present invention to a medium containing the abnormal mesenchymal stem cell and culturing for 24 hours to 144 hours, preferably for 24 hours to 72 hours, more preferably for 48 hours. The temperature and gas concentration in the activation treatment may be within the ranges for the temperature and gas concentration commonly used for mesenchymal stem cell cultivation. The temperature is, for example, from 25° C. to 37° C., preferably from 30° C. to 37° C., and more preferably 37° C. The oxygen concentration is, for example, from 2% to 30% and preferably from 2% to 20%. The activation treatment can be performed a plurality of times until sufficient activation is achieved.

The concentration of the activator in the activation treatment can be appropriately set as long as the activation is achieved. For example, the activator of the present invention contains the extract from fetal appendage in an amount of 0.01 mg/mL to 25 mg/mL, preferably in an amount of 0.05 mg/mL to 10 mg/mL, and more preferably in an amount of 0.1 mg/mL to 5 mg/mL. Under coexistence with a necessary component for the mesenchymal stem cell to proliferate (e.g., a serum component or a medium for mesenchymal stem cell), the activator of the present invention activates the mesenchymal stem cell more efficiently. Therefore, it is preferable to use the activator of the present invention together with these components.

Those skilled in the art can appropriately adjust the concentration of the activator, the temperature, the period of time and the number of times of the activation treatment, depending on the activation status of the cell.

Furthermore, the activation treatment can be performed on not only an abnormal mesenchymal stem cell in a state of being separated from a biological sample but also an abnormal mesenchymal stem cell in a state of being contained in a cell population derived from a biological sample. For example, in the case of a bone-marrow-derived mesenchymal stem cell, by subjecting the obtained bone marrow fluid as it is to the activation treatment, the abnormal mesenchymal stem cell in the cell population contained in the bone marrow fluid can be activated.

Determination of whether the abnormal mesenchymal stem cell is activated can be performed by evaluating the therapeutic effect of the cell after the activation treatment using the evaluation system reflecting the disease as described above. When the mesenchymal stem cell after the activation treatment shows a loss in disease-exacerbating effect and/or shows an increase in therapeutic effect as compared with that before the activation treatment, the mesenchymal stem cell is determined to be activated.

The therapeutic effect of the activated mesenchymal stem cell are sometimes not recovered to the extent equivalent to that of the normal mesenchymal stem cell. However, as long as the therapeutic effect is increased by the activation treatment, such mesenchymal stem cell can be used in the present invention.

Furthermore, the determination of the activation can be performed using a cell biological evaluation indicator similar to that of the abnormality determination, i.e., indicators such as morphology of cells and intracellular organelles, cellular proliferative potency, differentiation potency, levels of the protein expression, gene expression and extracellular secretion of various factors. When the mesenchymal stem cell after the activation treatment has properties identical or close to those of the normal mesenchymal stem cell with respect to one or more evaluation indicators, the mesenchymal stem cell can be determined to be activated.

The mesenchymal stem cell may proliferate by subculturing in vitro simultaneously with or after the activation.

The activated mesenchymal stem cell may be maintained in an undifferentiated state, or may be differentiated into a desired cell. Those skilled in the art appropriately determine the differentiation state of the activated cell depending on the application of the cell, such as target disease to be treated and therapy.

Maintenance of the mesenchymal stem cell in an undifferentiated state can be performed by culturing the mesenchymal stem cell in a medium suitable for maintaining the undifferentiated state, such as HyClone AdvanceSTEM Mesenchymal Stem Cell Expansion Kit (Thermo Fischer Scientific), MesenCult (trademark) MSC Basal Medium (STEMCELL Technology), Stromal Cellutions (trademark) Media (DV Biologics), or Medium kit for mesenchymal stem cells (MSCGM BulletKit, Lonza).

The mesenchymal stem cell can be differentiated by a generally known method such as a cultivation in a differentiation-inducing medium which contains a factor having a differentiation-inducing effect into desired cells. For example, in differentiation into osteoblasts, Bone Morphogenetic Proteins (BMP) 4, BMP2 or the like is used, and in differentiation into adipocytes, dexamethasone, 3-isobutyl-1-methyl xanthine, insulin or the like is used as a differentiation inducing factor.

The method for confirming the mesenchymal stem cell differentiation can be appropriately selected depending on the type of differentiated cells. For example, in order to confirm the differentiation into osteoblasts, a method for detecting alkaline phosphatase in cells (e.g., alkaline phosphatase staining) is used. In order to confirm the differentiation into adipocytes, a method for detecting triglyceride in cells (e.g., Oil Red O staining) is used.

When an abnormal mesenchymal stem cell contained in a cell population derived from a biological sample is subjected to the activation treatment, the mesenchymal stem cell in question may be separated or enriched from the cell population after the activation treatment, if necessary.

Separation or enrichment of the mesenchymal stem cell can be performed by culturing in a medium in which the mesenchymal stem cell is selectively amplified, or by flow cytometry and cell sorting based on one or more cell surface antigens specific to mesenchymal stem cells (e.g., CD29, CD73, CD90, CD105 and CD166).

The mesenchymal stem cell can be stored by a general procedure such as cryopreservation before and after the treatment including activation, proliferating cultivation and differentiation-inducing cultivation. For example, it is possible that the activated mesenchymal stem cell is cultured to proliferate, the resultant cells are separated into portions which contain a constant number of cells, the portions are stored, and then the required amount of portions is thawed and used in each administration.

Application of Mesenchymal Stem Cell of Present Invention

A third embodiment of the present invention relates to a mesenchymal stem cell for the treatment and/or prevention of a disease, wherein the cell is produced by the production method of the second embodiment, and a pharmaceutical for the treatment and/or prevention of a disease including the mesenchymal stem cell and/or its culture.

The activated mesenchymal stem cell obtained by the production method of the present invention can be used for the treatment and/or prevention of a disease. Furthermore, the present invention relates to a pharmaceutical for the treatment and/or prevention of a disease, including an activated mesenchymal stem cell and/or its culture. Furthermore, the present invention provides a method for treating and/or preventing a disease in which activated mesenchymal stem cells or a pharmaceutical containing these cells are used.

The disease to be treated and/or prevented may be any disease which is known to be treated and/or prevented by mesenchymal stem cells.

In one of the embodiments of the present invention, an activated mesenchymal stem cell is used to treat and/or prevent diabetes or its complications, an autoimmune disease, a chronic inflammatory disease, an allergic disease or osteoporosis. Specific examples of these diseases include type I diabetes and type II diabetes and their complications (e.g., diabetic nephropathy, diabetic retinopathy, diabetic neuropathy), cerebral infarction, cerebral apoplexy, myocardial infarction, angina pectoris, arteriosclerosis obliterans; autoimmune diseases such as rheumatoid arthritis, systemic lupus erythematosus, Sjögren's syndrome, polymyositis, dermatomyositis, scleroderma, hyperthyroidism, hypothyroidism, autoimmune adrenal dysfunction, pure red cell anemia, multiple sclerosis and autoimmune hepatitis; chronic inflammatory diseases such as chronic hepatitis, hepatic cirrhosis, chronic obstructive pulmonary disease, Crohn's disease, ulcerative colitis and Behcet's disease; allergic diseases such as atopic dermatitis and bronchial asthma; and osteoporosis.

In a preferred embodiment of the present invention, the disease to be treated and/or prevented is diabetic nephropathy, diabetic retinopathy or diabetic neuropathy. It is assumed that the activated mesenchymal stem cells improve microangiopathy, thereby diabetic complications can be treated and/or prevented. As described in the following examples, rheumatoid arthritis is also a disease which is preferably treated and/or prevented by the activated mesenchymal stem cells.

The pharmaceutical of the present invention contains an effective amount of the activated mesenchymal stem cells.

The term "effective amount" used herein means an amount which is effective for the treatment and/or prevention of the disease. Such effective amount is appropriately adjusted depending on the type of disease, the severity of conditions, the patients or other medical factors.

In a preferred embodiment of the pharmaceutical of the present invention, the effective amount of the mesenchymal stem cells is from $10^6$ to $10^9$ and preferably from $10^7$ to $10^9$, per 1 kg of weight of the individual to be administered.

The pharmaceutical of the present invention may contain an effective amount of a culture of the activated mesenchymal stem cells. The culture is preferably a culture supernatant of the mesenchymal stem cells. It is known that the culture supernatant of mesenchymal stem cells contains various humoral factors produced by mesenchymal stem cells and has a disease therapeutic effect, similarly to mesenchymal stem cells (JP 2013-018756 A and Watanabe, S. et al., J Gastroenterol. 2013; Epub ahead of print, PMID: 24217964). Furthermore, the reference examples described below show the therapeutic effect of the cell culture supernatant of mesenchymal stem cells.

The culture can be obtained by culturing the activated mesenchymal stem cells in a culture medium commonly used in mesenchymal stem cell cultivation such as α-MEM or DMEM.

In a preferred embodiment of the pharmaceutical of the present invention, the effective amount of a culture of the mesenchymal stem cells is from 0.1 mg to 100 mg, preferably from 0.2 mg to 50 mg, and more preferably from 0.5 mg to 20 mg per 1 kg of weight of the individual to be administered, and this amount can be administered in one or more divided doses.

The pharmaceutical of the present invention is commonly used in the form of parenteral formulation, such as injections and drip infusions. Examples of carriers used as parenteral formulations include aqueous carriers such as physiological saline and an isotonic solution containing glucose, D-sorbitol, etc.

Furthermore, the pharmaceutical of the present invention may be a composition containing a buffer, a stabilizer, a preservative and other components which are pharmaceutically acceptable. The pharmaceutically acceptable components are well-known to those skilled in the art. Those skilled in the art can appropriately select and use the pharmaceutically acceptable components, for example from those described in Japanese Pharmacopoeia, sixteenth edition or other written standard, within the scope of his/her normal implementation ability, depending on dosage forms.

The method for administering the pharmaceutical of the present invention is not particularly limited, but in the case of parenteral formulations, there can be exemplified, for example, intravascular administration (preferably intravenous administration), intraperitoneal administration, intestinal administration and subcutaneous administration. In one of the preferred embodiments, the pharmaceutical of the present invention is administered to a living body by intravenous administration. In addition, the pharmaceutical of the present invention may be used in combination with other pharmaceuticals, depending on the disease to be treated and/or prevented.

A fourth embodiment of the present invention relates to a method for the treatment and/or prevention of a disease including administering the pharmaceutical containing an effective amount of the mesenchymal stem cell and/or its culture of the third embodiment of the present invention to a subject. The meaning of each terms in the fourth embodiment is as described in the third embodiment.

The present invention will be described in more detail by the following examples. These examples are provided solely to assist the understanding of the present invention, and the technical scope of the present invention is not limited thereto.

EXAMPLES

Example 1

Preparation of Umbilical Cord Tissue Extracts

Umbilical cord tissues were obtained from human cases (n=20) who had no maternal complications and underwent the cesarean section, by cutting off from umbilical cord roots immediately after the delivery of the placenta. The obtained umbilical cord tissues were collected into sterile containers and retained on ice.

The preparation of extracts from umbilical cord tissues was performed as follows. All the operations were carried out in a clean bench.
1) The blood adhered to the umbilical cord tissue and the blood in the blood vessels were rinsed with physiological saline as much as possible.
2) Aliquots of 10 to 30 mL of cell culture medium α-MEM without serum and antibiotics were dispensed in glass culture dishes.
3) The rinsed umbilical cord tissue was divided into approximately 5 g wet weight portions, and approximately 5 g of the umbilical cord tissue was placed in one culture dish.
4) The amniotic sheath was longitudinally cut open in the medium of the culture dish using tweezers and sharp-pointed scissors.
5) Furthermore, the umbilical artery and the umbilical vein in the longitudinal direction were peeled from the Wharton's jelly using tweezers.
6) Furthermore, the Wharton's jelly and the amniotic sheath were cut into approximately 5-mm thin strips in the longitudinal direction using tweezers.
7) The medium containing all of the cord blood vessels, the Wharton's jelly and the amniotic sheath obtained in 5) and 6) was collected to a 50-mL sample tube.
8) The sample tube of 7) was horizontally placed on a shaker in a refrigerator at 4° C. and shaken reciprocally at 70 to 100 rpm for 72 hours.
9) 72 hours later, the sample tube was centrifuged at 4° C. and 2000 rpm (300×g) for 5 minutes.
10) The supernatant of 9) was recovered to obtain umbilical cord tissue extract (hereinafter, also referred to as "WJ" extract).

The extracts were stored in sterile containers at 4° C. or −80° C. and used in subsequent examples and reference examples. Unless otherwise described, the amount of α-MEM used in 2) was 20 mL, and the extracts were stored at 4° C.

Example 2

Analysis of Umbilical Cord Tissue Extracts

The umbilical cord tissue extracts prepared in Example 1 were subjected to the following analysis.

2-1. Morphology Observation

Figure 1:
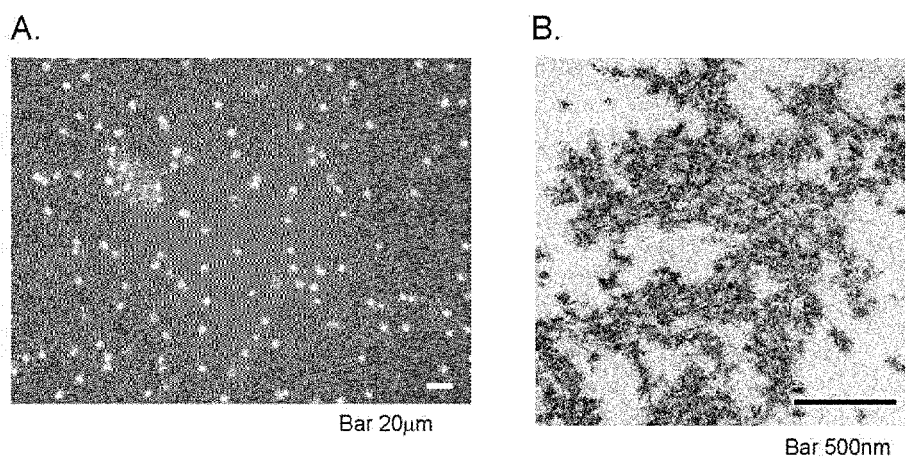
FIG. 1A is a phase contrast microscopy image and FIG. 1B is an electron microscopy image of umbilical cord tissue extract (WJ), which is an example of extract from fetal appendage.

The extracts were subjected to phase-contrast microscope observation using a fluorescence microscope (including phase contrast observation) BZ9000 (KEYENCE) or TE200 (NIKON). In addition to network-structured extracellular-matrix components, erythrocytes assumed to be derived from the cord blood were found out. However, the presence of other cells having proliferation potency was not observed (FIG. 1A).

The extracts were subjected to electron microscope observation using samples for electron microscope observation produced in the following manner. The extracts were fixed with 2.5% glutaraldehyde for 24 hours. Then, the samples were washed with 0.1 M PBS and fixed with a 1% osmium tetroxide aqueous solution, followed by dehydration with ethanol. The samples were immersed in propylene oxide and embedded with an epoxy resin, followed by heat polymerization. Ultra-thin sections of the samples were produced using Ultramicrotome MT-X (RMC), electron-stained, and then observed with a transmission electron microscope H-7650 (Hitachi High-Technologies). The presence of fibrous substances assumed to be extracellular matrices was observed (FIG. 1B).

2-2. Content of Growth Factor, Hyaluronic Acid and Glutamate

Figure 2:
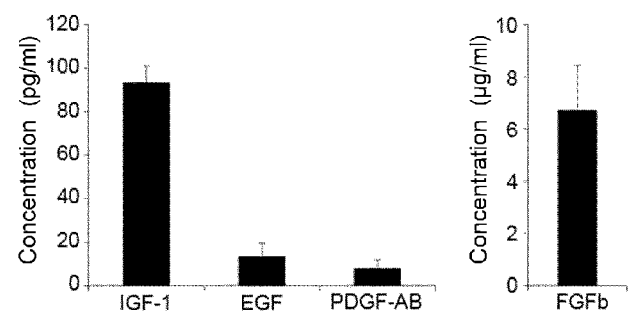
FIG. 2A is a graph showing the content of growth factors.
FIG. 2B is a graph showing the content of hyaluronic acid.
FIG. 2C is a graph showing the content of L-Glutamate in the umbilical cord tissue extracts.
Figure 2:
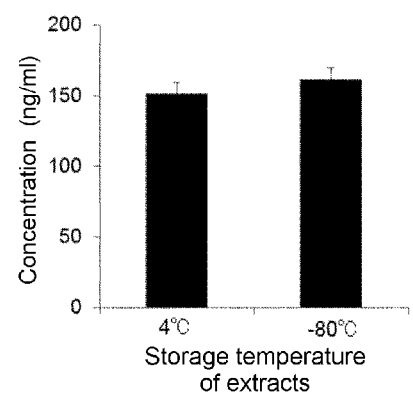
Figure 2:
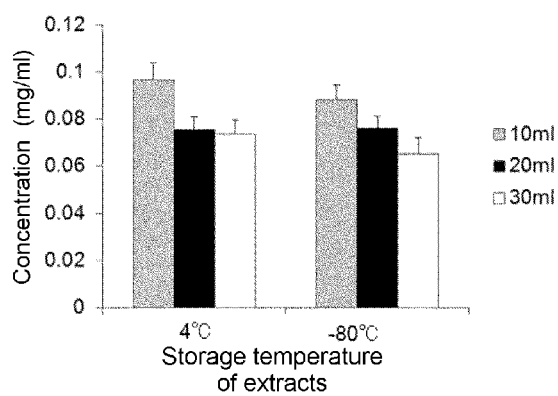

The amounts of growth factors (IGF-1, EGF, PDGF-AB and FGFb) (16 batches of extracts were used), hyaluronic acid (8 batches of extracts were used), L-Glutamate (19 batches of extracts were used) contained in the extracts were measured by ELISA. IGF-1 was measured with Human IGF-I Quantikine ELISA Kit (R&D Systems), EGF was measured with Human EGF Quantikine ELISA Kit (R&D Systems), PDGF-AB was measured with Human PDGF-AB Quantikine ELISA Kit (R&D Systems), FGFb was measured with Human FGF basic Quantikine ELISA Kit (R&D Systems), hyaluronic acid was measured with Hyaluronan Quantikine ELISA Kit (R&D Systems) and L-Glutamate was measured with F-kit L-Glutamate assay kit (J. K International). As for hyaluronic acid and L-Glutamate, the extracts stored at 4° C. as well as at −80° C. were measured. As for L-Glutamate, extracts prepared by using 10 mL, 20 mL or 30 mL of extraction medium (α-MEM) were measured. The results are shown in FIG. 2. With the increase in the amount of extraction medium, the L-Glutamate concentration in the extracts was slightly decreased (FIG. 2C). The storage temperatures of the extracts had no large influence on the content of the measured components (FIGS. 2B and 2C).

2-3. Viscosity

Figure 3:
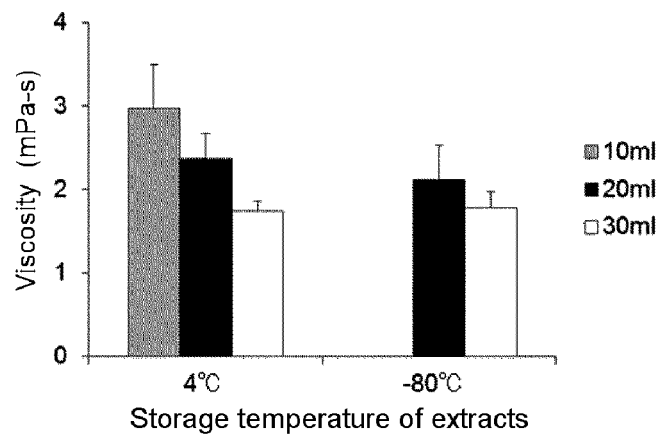
FIG. 3 is a graph showing the viscosity of the umbilical cord tissue extracts.

The viscosity of the extracts prepared by using 10 mL, 20 mL or 30 mL of extraction medium (α-MEM) and stored at 4° C. and −80° C. (15 batches for each extract) was measured with a turning fork viscometer SV-1A (A&D). The results are shown in FIG. 3. Similarly to the result of the L-Glutamate content, the viscosity decreased depending on the amount of the extraction medium used, and the storage temperatures had no influence on the viscosity.

2-4. Content of Exosome

Exosome fractions were extracted from the extracts of the umbilical cord tissues using Total Exosome Isolation Kit (Invitrogen). Exosome fractions were recovered as pellets and subjected to electron microscope observation.

In addition, the recovered pellets were extracted with a buffer, and Western blotting method was performed with the anti-human CD9 antibody (System Biosciences) and the anti-human HSP70 antibody (System Biosciences) to confirm the presence of exosomes by the expression of CD9 and HSP70 as markers. The content of exosomes was quantified by ELISA (CD9, Exosome, ELISA Kit, ExoELISA, System Biosciences) using the anti-human CD9 antibody.

Figure 4:
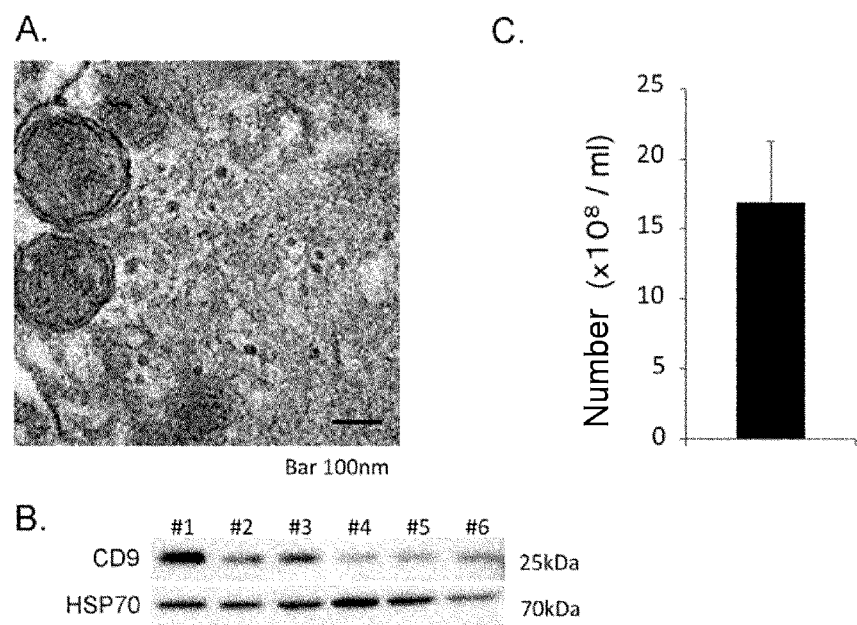
FIG. 4A is an electron microscopy image of exosomes in umbilical cord tissue extracts.
FIG. 4B is Western blotting of the exosomes obtained using anti-CD9 and anti-HSP70 antibodies.
FIG. 4C is a graph showing the content of the exosomes measured using the anti-CD9 antibody, wherein #1 to #6 in FIG. 4B correspond to exosome fractions derived from six different batches of umbilical cord tissue extracts.

FIG. 4A shows an electron microscopy image, FIG. 4B shows the Western blotting results of 6 batches of umbilical cord tissue extracts, and FIG. 4C shows the results of ELISA quantification of 15 batches of umbilical cord tissue extracts. The extracts of the umbilical cord tissues contained approximately $17 \times 10^8$ exosomes/mL on average.

2-5. Culture Assay

Figure 5:
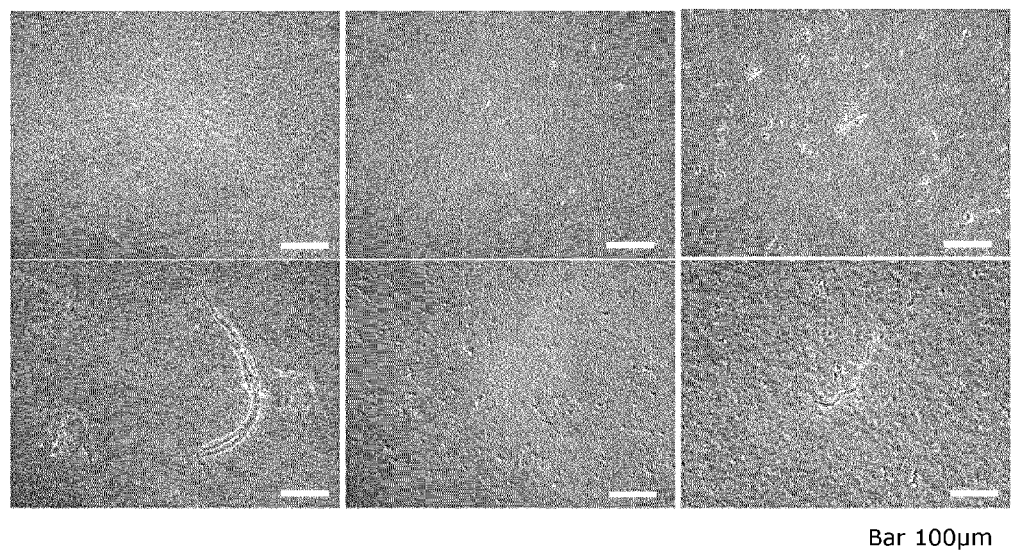
FIG. 5 shows images of culture of different batches of umbilical cord tissue extracts.

To umbilical cord tissue extracts (6 batches, stored at 4° C. for 14 to 90 days), FBS was added at a final concentration of 10%. Then, the mixtures were seeded in culture dishes and cultured at 37° C. in an atmosphere of 5% $CO_2$ for 96 hours. FIG. 5 shows phase contrast microscopy images of the cultured extracts. Collagen fibers, erythrocytes and the like contained in the extracts were observed, however, cells which adhered to the culture dishes and proliferated were not observed. This shows that the extracts do not contain cells that are derived from umbilical cord tissues and have proliferation potency.

Example 3

Activation of Mesenchymal Stem Cells Derived from Diabetic Animals by Umbilical Cord Tissue Extracts 3-1. Collection of Mesenchymal Stem Cells 8-week-old male Sprague-Dawley (SD) rats (Japan SLC) were administered with 500 μL of STZ citrate buffer solution (containing STZ in an amount corresponding to 40 mg/kg body weight) into their tail veins. The blood glucose level of the rats increased to 600 mg/dL or more 1 week after administration of STZ, which was hyperglycemic. The rats were sacrificed eight weeks after STZ administration and long bones were obtained. The whole bone marrow cells were recovered from the long bones and seeded in 150-$cm^2$ culture dishes, followed by cultivation. The cultivation was performed by using α-MEM containing 15% FBS, 1% penicillin, 1% streptomycin and 100 mg/dL of glucose at 37° C. in an atmosphere of 20% $O_2$. The medium was replaced after 72 hours and non-adhered cells were removed to obtain bone-marrow-derived mesenchymal stem cells (DM-MSCs, Passage0 (P0)) as adhered cells. Hereafter, "Passage" or "P" used with a number indicates a number of times of cell passages. For example, cells (P0) indicate cells of which the number of times of passages is zero, i.e. primary culture cells which are not passaged. The cells (P1) indicate cells of which the number of times of passages is one.

Normal rat-derived mesenchymal stem cells as control (Control-MSCs, P0) were obtained in the same manner as that of DM-MSCs except that a citrate buffer solution was administered in place of the STZ solution.

3-2. Activation Treatment

The activation treatment was performed by culturing DM-MSCs (P1) in α-MEM (containing 15% FBS, 1% penicillin and 1% streptomycin) to which the extract of Example 1 was added at a concentration of 1.0 mg/mL at 37° C. in an atmosphere of 20% $O_2$ for 48 hours to 96 hours. When the cells adhered to the culture dishes became 85%-90% confluent, the cells were passaged and cultured in the medium with the extract added in the same manner as described above. The subcultured cells (P3) were designated as DM-MSCs-WJ (+).

The non-activated DM-MSCs-WJ (−) as control were prepared by culturing DM-MSCs (P1) in α-MEM (containing 15% FBS, 1% penicillin and 1% streptomycin) without the extract of Example 1 in the same manner as that of DM-MSCs-WJ (+).

Furthermore, normal rat-derived Control-MSCs as control were prepared by subculturing the Control-MSCs (P1) obtained in 3-1. in the medium without the extract in the same manner as that of DM-MSCs-WJ (−).

3-3. Evaluation of Activated Mesenchymal Stem Cells

The mesenchymal stem cells obtained in 3-1. and 3-2. as described above were evaluated in the following manner.

(1) MTT Assay

Figure 6:
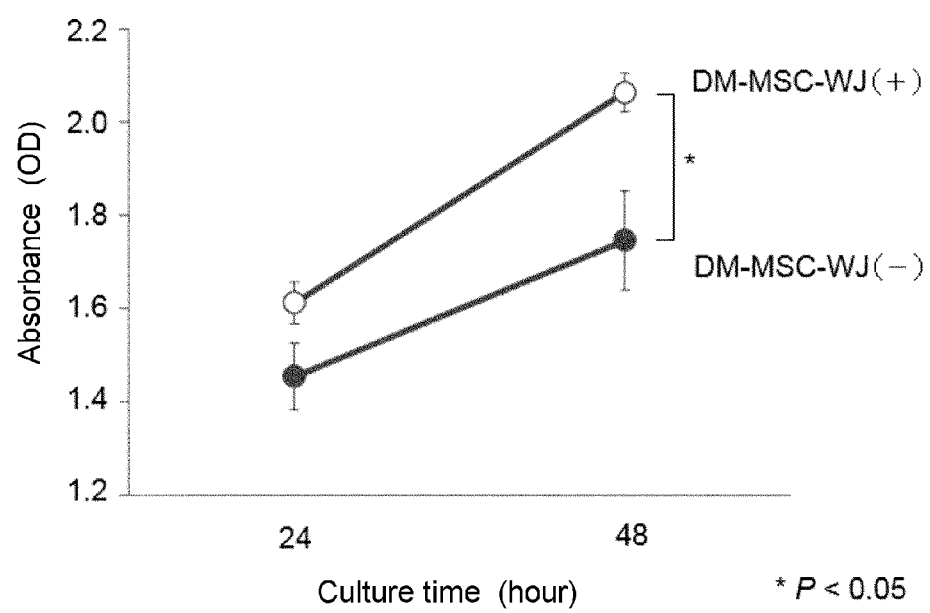
FIG. 6 is a graph showing results of MTT assays of mesenchymal stem cells from streptozotocin (STZ)-induced type I diabetes model rats wherein the cells were subjected to the activation treatment with the umbilical cord tissue extracts (DM-MSCs-WJ (+)) and mesenchymal stem cells from STZ-induced type I diabetes model rats wherein the cells were not subjected to the activation treatment (DM-MSCs-WJ (−))

Each of the mesenchymal stem cells was seeded in 96 multi-well culture dishes. 24 hours later, the cells were cultured in α-MEM to which the extracts (15 batches) of Example 1 were added at a concentration of 0.5 to 1.0 mg/mL or in α-MEM without the extracts for 48 hours. The time of addition of the extracts was defined as time 0. 24 or 48 hours later, WST8 (Water soluble Tetrazolium salts, DOJINDO) was added to each of the wells. The enzyme activity of reduction to a formazan dye was measured and the growth rate of the cells was analyzed (FIG. 6). DM-MSCs-WJ (+) after the activation treatment had high proliferation potency, compared with that of DM-MSCs-WJ (−).

(2) Morphology of Cells

Figure 7:
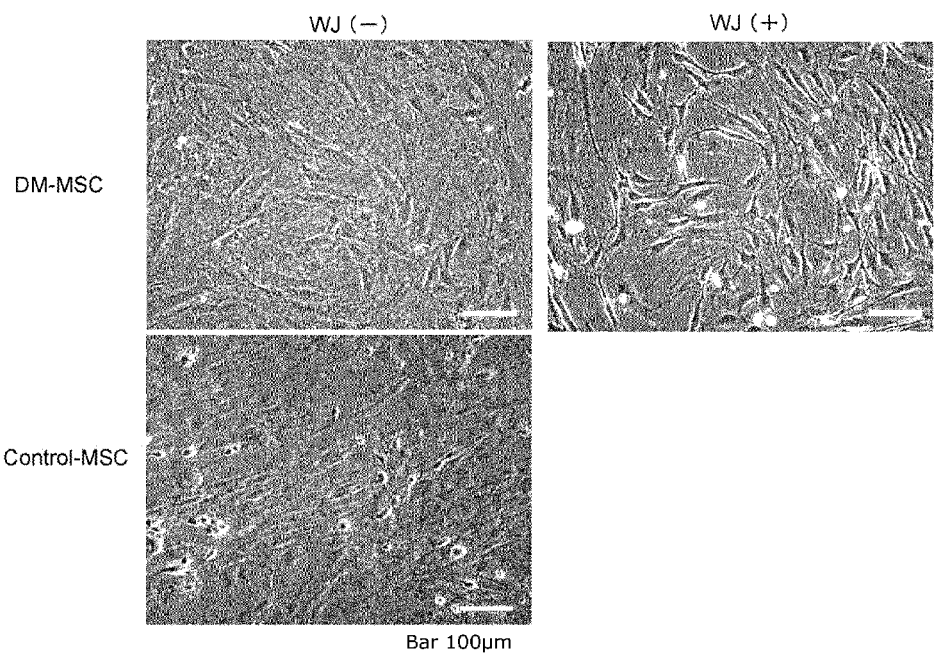
FIG. 7 shows phase contrast microscopy images of mesenchymal stem cells from normal rats (Control-MSCs), DM-MSCs-WJ (−) and DM-MSCs-WJ (+)

The phase contrast microscopy observation was performed in the same manner as in Example 2. DM-MSCs-WJ (−) were flat fibroblast-like cells with a few projections, whereas DM-MSCs-WJ (+) were found to have projections equal to or more than those of Control-MSCs and to have increased thickness (FIG. 7).

(3) Morphology of Intracellular Organelles

Figure 8:
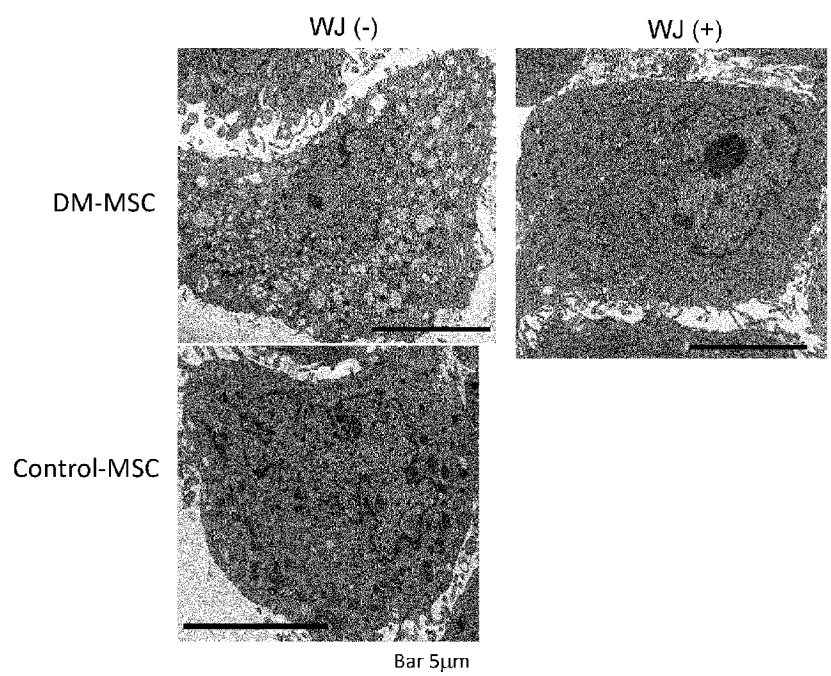
FIG. 8 shows electron microscopy images (low magnification) of Control-MSCs, DM-MSCs-WJ (−) and DM-MSCs-WJ (+)
Figure 9:
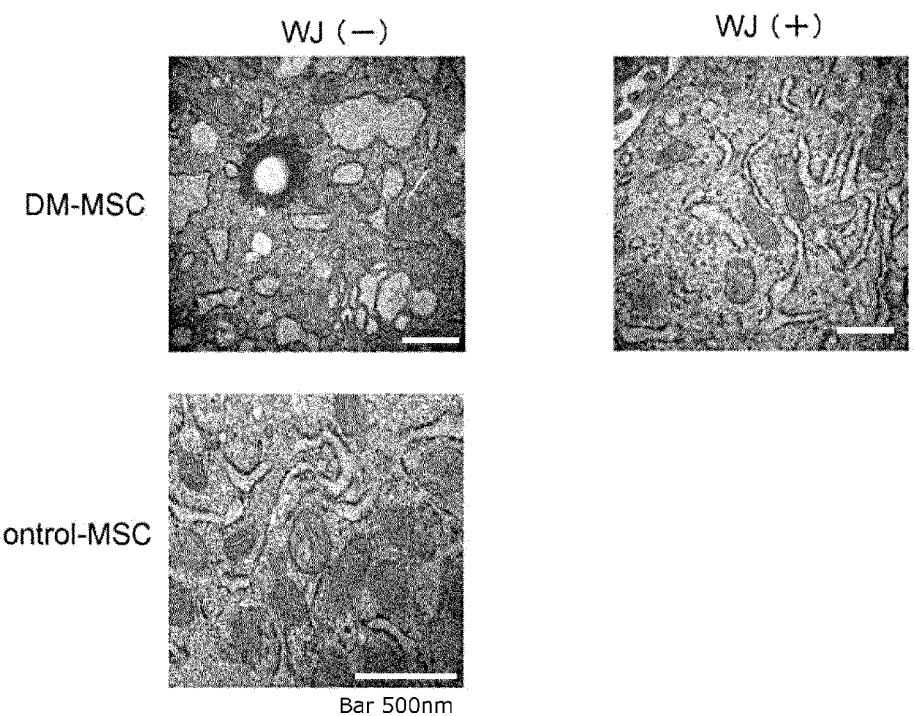
FIG. 9 shows electron microscopy images (high magnification) of Control-MSCs, DM-MSCs-WJ (−) and DM-MSCs-WJ (+)

The electron microscope observation was performed in the same manner as in Example 2. The number of mitochondria in DM-MSCs-WJ (−) decreased, compared with that in Control-MSCs (FIG. 8). Furthermore, in addition to swelling of cristae in the mitochondria, a significant expansion of the endoplasmic reticulum indicating endoplasmic reticulum stress was observed in DM-MSCs-WJ (−) (FIG. 9). An improvement in these morphological abnormalities was observed in DM-MSCs-WJ (+).

(4) Proliferation Potency

The proliferation potency of cells was further evaluated by Ki67 staining and the activation of a signaling factor ERK (Extracellular signal-Regulated Kinase) 1/2, which is a kinase mediating the cellular proliferation, differentiation, survival promoting effect or the like.

1) Ki67 Staining

Figure 10:
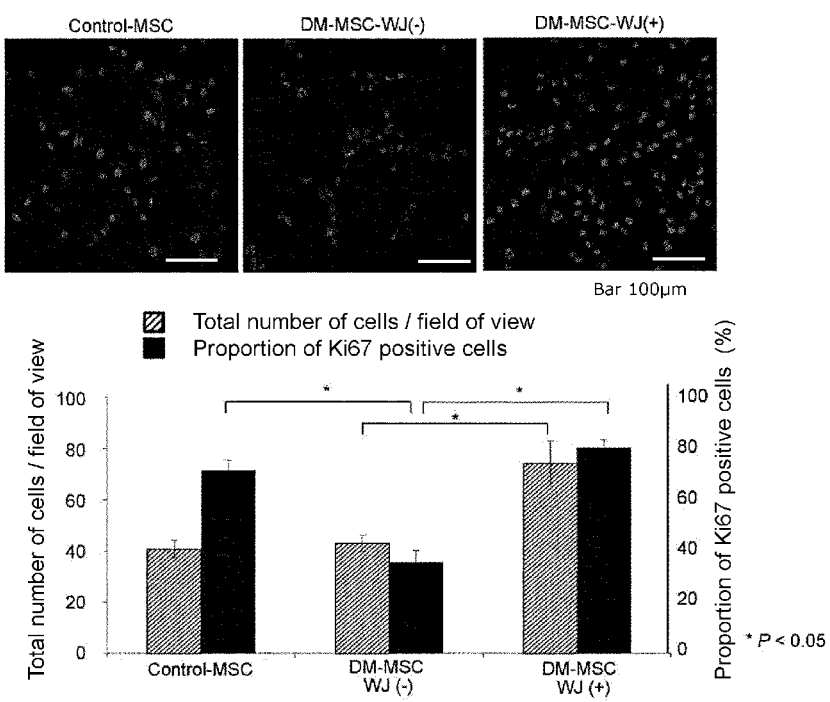
FIG. 10 shows Ki67 staining results of Control-MSCs, DM-MSCs-WJ (−) and DM-MSCs-WJ (+); the upper part shows fluorescence microscopy images and the lower part is a graph showing the total number of cells per field of view, which is calculated from the number of DAPI positive cells and Ki67 positive cells, and the proportion of Ki67 positive cells.

Each of the mesenchymal stem cells was seeded in chamber slides and then cultured in α-MEM to which the extract (1 batch) of Example 1 was added at a concentration of 1.0 mg/mL or in α-MEM without the extract for 48 hours. After the cultivation, the cells were fixed with 4% paraformaldehyde and Ki67-staining was performed by using the anti-Ki67 antibody (abcam) labeled with Cy3. The nuclei were stained with DAPI (DOJINDO). The cells were observed using a confocal laser scanning microscope system: LSM 510 META (ZEISS), and the number of DAPI-positive cells and the number of Ki67-positive cells were counted. The results are shown in FIG. 10. The total cell number of DM-MSCs-WJ (+) after the activation treatment which prolife rated during the specific period of time was significantly increased, compared with that of DM-MSCs-WJ (−). On the other hand, the proportion of the Ki67-positive cells displaying proliferation activity in DM-MSCs-WJ (−) was significantly low, compared with that in Control-MSCs. The proportion in DM-MSCs-WJ (+) after the activation treatment was recovered to the same extent as that in Control-MSCs. Hence, it was shown that the cells were activated by the extract of Example 1.

2) Activation of ERK1/2

Figure 11:
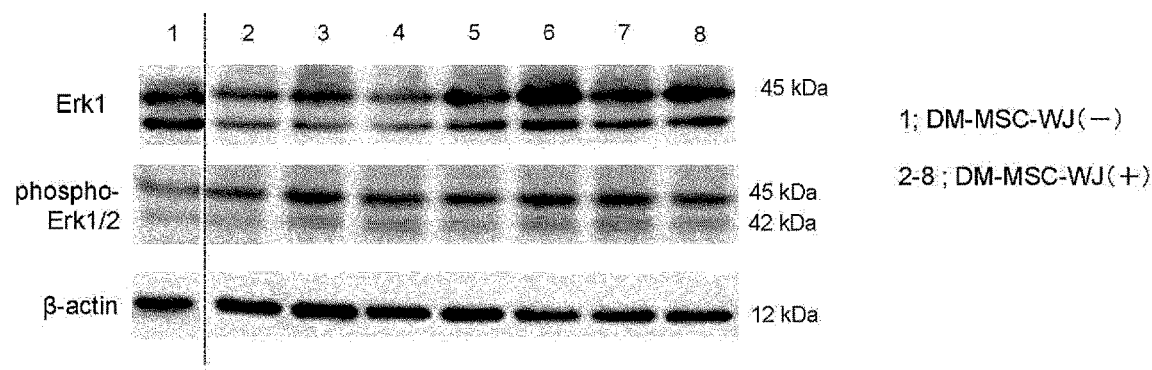
FIG. 11 shows Western blotting showing the activation of ERK1/2 in DM-MSCs-WJ (−) and DM-MSCs-WJ (+), wherein Lane 1 corresponds to DM-MSCs-WJ (−), and Lanes 2 to 8 correspond to DM-MSCs-WJ (+) subjected to the activation treatment with seven different batches of umbilical cord tissue extracts.

Each of the mesenchymal stem cells was seeded and cultured in α-MEM to which the extracts (7 batches) of Example 1 were added at a concentration of 1.0 mg/mL or in α-MEM without the extracts for 48 hours. The cells were collected, and then the proteins were extracted in an ordinary manner and analyzed by Western blotting. ERK1/2 was detected using the anti-ERK1/2 antibody (Santa Cruz), phosphorylated ERK1/2 was detected using the anti-p-ERK1/2 antibody (Cell Signaling Technology), and β-actin was detected using the anti-β-actin antibody (Sigma). The results are shown in FIG. 11. Compared with DM-MSCs-WJ (−), DM-MSCs-WJ (+) after the activation treatment showed an increase in the expression of phosphorylated ERK1/2. This indicates that ERK1/2 is activated by the activation treatment.

(5) Endoplasmic Reticulum Stress

Figure 12:
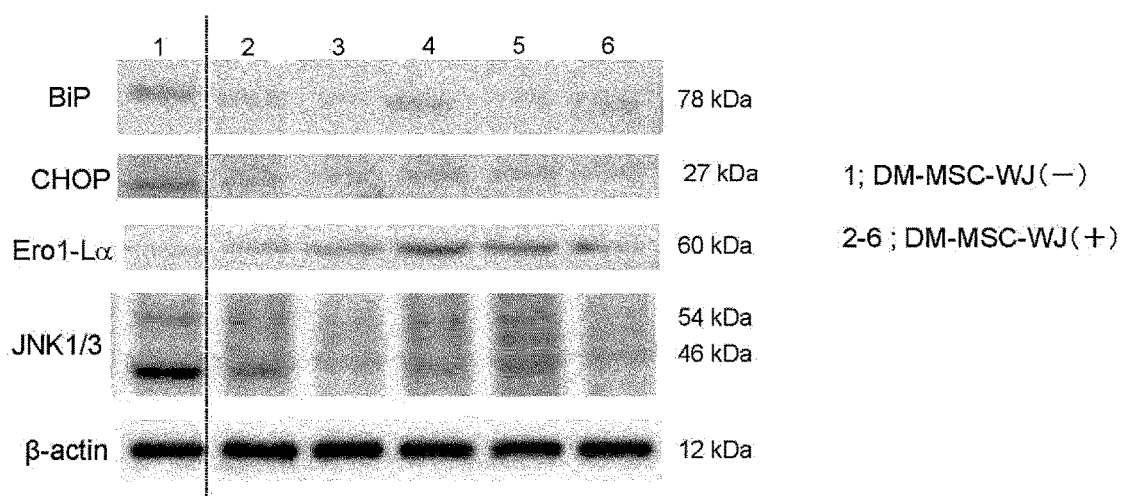
FIG. 12 shows Western blotting showing the expression of endoplasmic reticulum stress-related proteins in DM-MSCs-WJ (−) and DM-MSCs-WJ (+), wherein Lane 1 corresponds to DM-MSCs-WJ (−) and Lanes 2 to 6 correspond to DM-MSCs-WJ (+) subjected to the activation treatment with five different batches of umbilical cord tissue extracts.

Each of the mesenchymal stem cells was seeded and then cultured in α-MEM to which the extracts (5 batches) of Example 1 were added at a concentration of 1.0 mg/mL or in α-MEM without the extracts for 48 hours. The cells were collected, the proteins were extracted in an ordinary manner, and the expression of endoplasmic-reticulum-stress related proteins was analyzed by Western blotting. Binding immunoglobulin Protein (BiP) was detected using the anti-BiP antibody (Cell Signaling Technology), C/EBP-Homologous Protein (CHOP) was detected using the anti-CHOP antibody (Cell Signaling Technology), Ero1-Like protein (Ero1-L) a was detected using the anti-Ero1-Lα antibody (Cell Signaling Technology), and c-Jun N-terminal Kinase (JNK) 1/3 was detected using the anti-JNK1/3 antibody (Santa Cruz). The results are shown in FIG. 12. Compared with DM-MSCs-WJ (−), DM-MSCs-WJ (+) after the activation treatment showed a decrease in the expressions of BiP, CHOP and JNK1/3, and showed an increase in the expression of Ero1-Lα. This result indicates that the endoplasmic reticulum stress is suppressed by the activation treatment, similarly to the results seen in the electron microscope observation of cells.

(6) Expression of Growth Factor, Differentiation-Related Factor and Cytokine/Chemokine Genes mRNAs were extracted from each of the mesenchymal stem cells (reagent; TRI reagent, Molecular Research Center, Inc.). The expression of the factors shown in Table 2 was analyzed by Real-time PCR assay (reagent; Power SYBR (registered trademark) Green PCRMaster Mix, Applied Biosystems, device; Applied Biosystems 7500 real-time PCR system). Glyceraldehyde-3-phosphate-dehydrogenase (GAPDH) was used as control to normalize the expression level of each of the factors.

TABLE 2

| Factor | Forward primer | Reverse primer |
| --- | --- | --- |
| GAPDH | 5'-ATGGGTGTGAAC CACGAGAAA-3' (SEQ ID NO: 1) | 5'-GGATACATTGGG GGTAGGAA-3' (SEQ ID NO: 2) |
| IGF-1 | 5'-TACTTCAACAAG CCCACAGGC-3' (SEQ ID NO: 3) | 5'-TCAGCGGAGCAC AGTACATCTC-3' (SEQ ID NO: 4) |
| α-SMA | 5'-TCCCTGGAGAAG AGCTACGAAC-3' (SEQ ID NO: 5) | 5'-CCAATGAAAGAT GGCTGGAAG-3' (SEQ ID NO: 6) |

TABLE 2-continued

| Factor | Forward primer | Reverse primer |
| --- | --- | --- |
| TNFα | 5'-TGTACCTGGGAG GAGTCTTCCA-3' (SEQ ID NO: 7) | 5'-CAGTCGCTTCAC AGAGCAATG-3' (SEQ ID NO: 8) |
| IL-1β | 5'-CTGACAGACCCC AAAAGATTAAGG-3' (SEQ ID NO: 9) | 5'-CTTGTCGAGATG CTGCTGTGA-3' (SEQ ID NO: 10) |
| IFNγ | 5'-GCCAAGGCACAC TCATTGAAA-3' (SEQ ID NO: 11) | 5'-CTTTTGCCAGTT CCTCCAGATATC-3' (SEQ ID NO: 12) |
| IL-2 | 5'-CAGGCCACAGAA TTGAAACATC-3' (SEQ ID NO: 13) | 5'-CCAGCGTCTTCC AAGTGAAAG-3' (SEQ ID NO: 14) |
| RANTES | 5'-TATGGCTCGGAC ACCACTCC-3' (SEQ ID NO: 15) | 5'-GACAAAGACGAC TGCAAGGTTG-3' (SEQ ID NO: 16) |

The results are shown in FIG. 13. The expression levels of α-SMA, TNFα, IL-1β, IFNγ, IL-2 and RANTES were increased in DM-MSCs-WJ (−), compared with those in Control-MSCs, whereas, the expression levels were decreased in DM-MSCs-WJ (+), compared with those in DM-MSCs-WJ (−). The opposite tendency was observed in IGF-1.

(7) Differentiation Potency into Adipocytes

Each of the mesenchymal stem cells was cultured in an adipose differentiation-inducing culture medium (reagent; Mesenchymal Stem Cell Functional Identification Kit, R&D Systems), followed by induction of differentiation for 14 days. Thereafter, the cells were stained with Oil Red O (Sigma). FIG. 14 shows bright field microscopy images. Although DM-MSCs-WJ (+) showed an increase in the number of cells, compared with DM-MSCs-WJ (−), the proportion of Oil Red O-positive cells to the total cells was the same in both MSCs. Therefore, it is shown that the activation treatment has no effect on the differentiation potency into adipocytes originally included in mesenchymal stem cells.

(8) Cell Surface Antigens

The expression of surface antigens in DM-MSCs-WJ (+) was analyzed by flow cytometry (device; BD FACS Calibur flow cytometer) using the anti-CD90 antibody (Immunotec), the anti-CD44 antibody (Immunotec), the anti-CD45 antibody (Immunotec), the anti-CD43 antibody (Immunotec), the anti-CD31 antibody (Immunotec), the anti-CD11b antibody (Immunotec), and the anti-HLA-DR antibody (abcam). As shown in FIG. 15, DM-MSCs-WJ (+) expressed a mesenchymal stem cell marker: CD90, but did not express negative markers: CD44, CD45, CD43, CD31, CD11b, and HLA-DR. This suggests that the activation treatment has no effect on the cell surface antigens of the mesenchymal stem cells.

Example 4

Examination of Concentration of Umbilical Cord Tissue Extracts and Evaluation of Activation Potency in Absence of Serum Component STZ-administered rats of type I diabetes models and OLETF rats of type II diabetes models were used to examine the concentration of the umbilical cord tissue extracts necessary for activation, and the effect of the presence of the serum component on the activation potency of the umbilical cord tissue extracts was evaluated.

4-1. Examination of Concentration of Extracts to be Added

Figure 16:
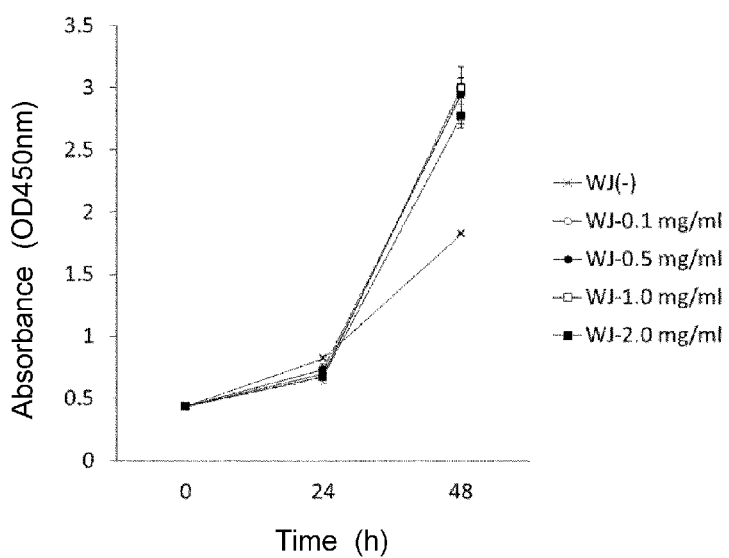
Figure 16:
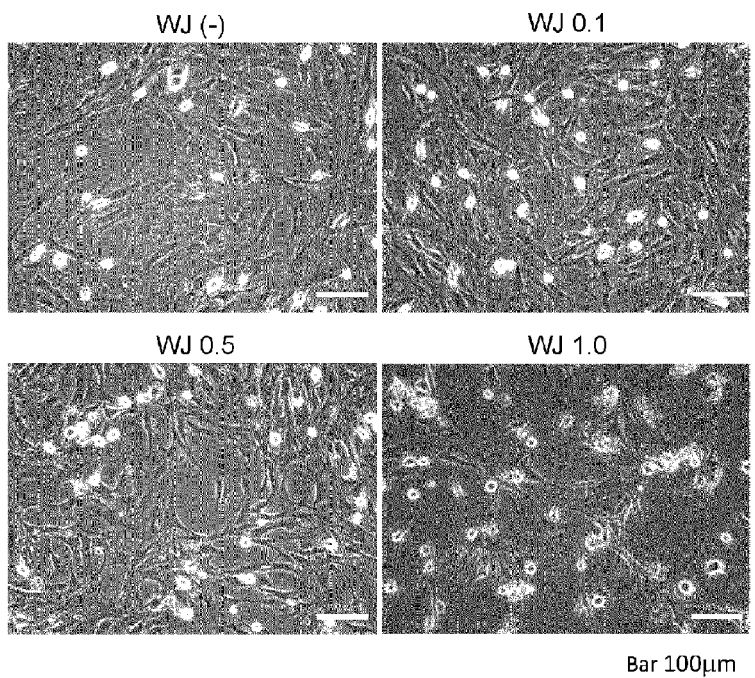
Figure 17:
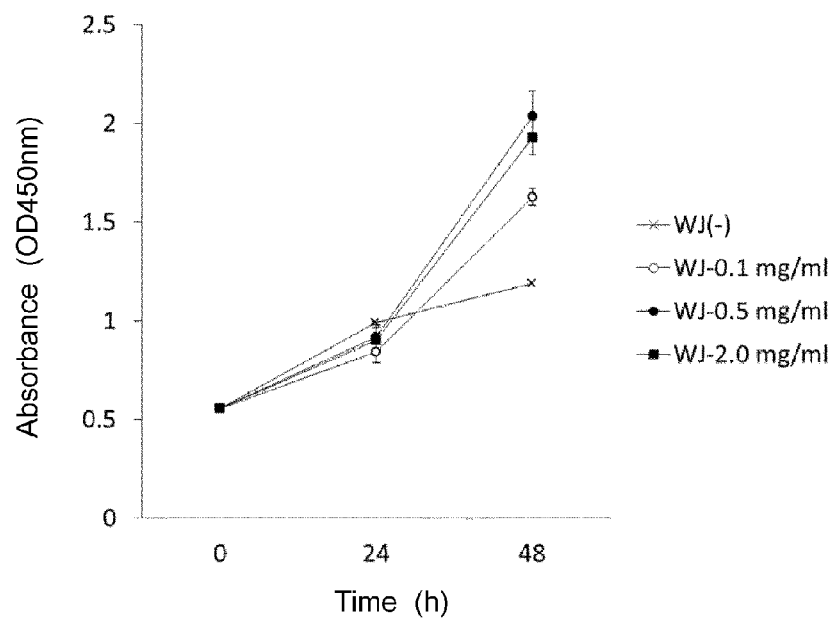
Figure 17:
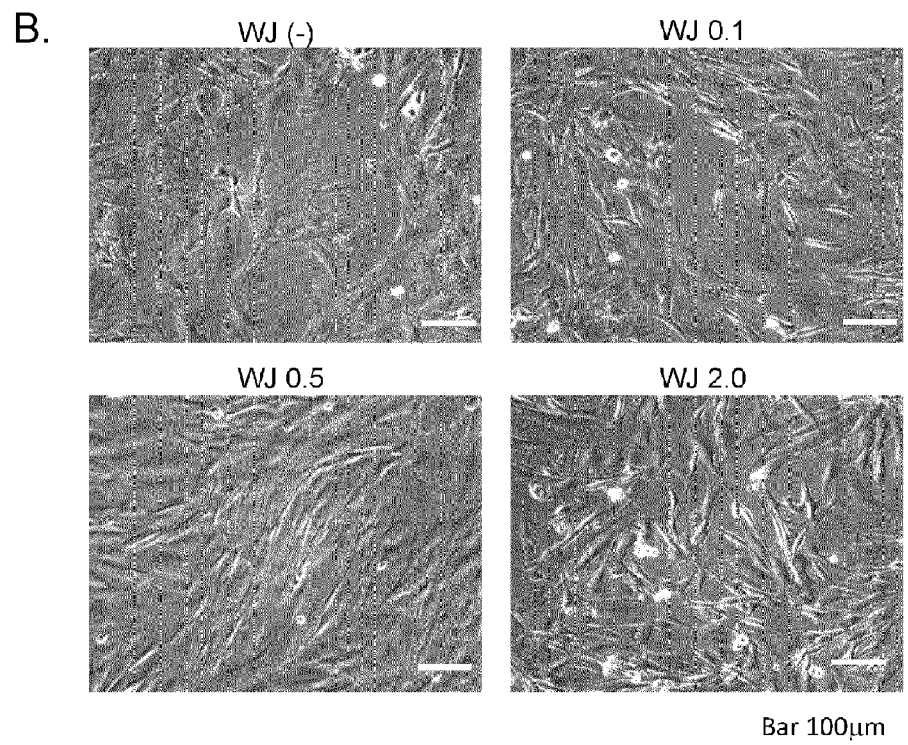

The concentration of the extracts to be added was set to a range of 0.1 mg/mL to 2.0 mg/mL and mesenchymal stem cells prepared from STZ-administered rats and OLETF rats (6-month-old) in the same manner as in 3-1. of Example 3 were subjected to the activation treatment in the same manner as in 3-2. The results of MTT assays and cell morphology observation confirmed that, in the case where the concentration of the extracts added to the mesenchymal stem cells from the diabetic rats was 0.5 mg/mL or more, sufficient activation was given (FIGS. 16 and 17).

4-2. Activation Potency of Extracts in Absence of Serum Component

Figure 18:
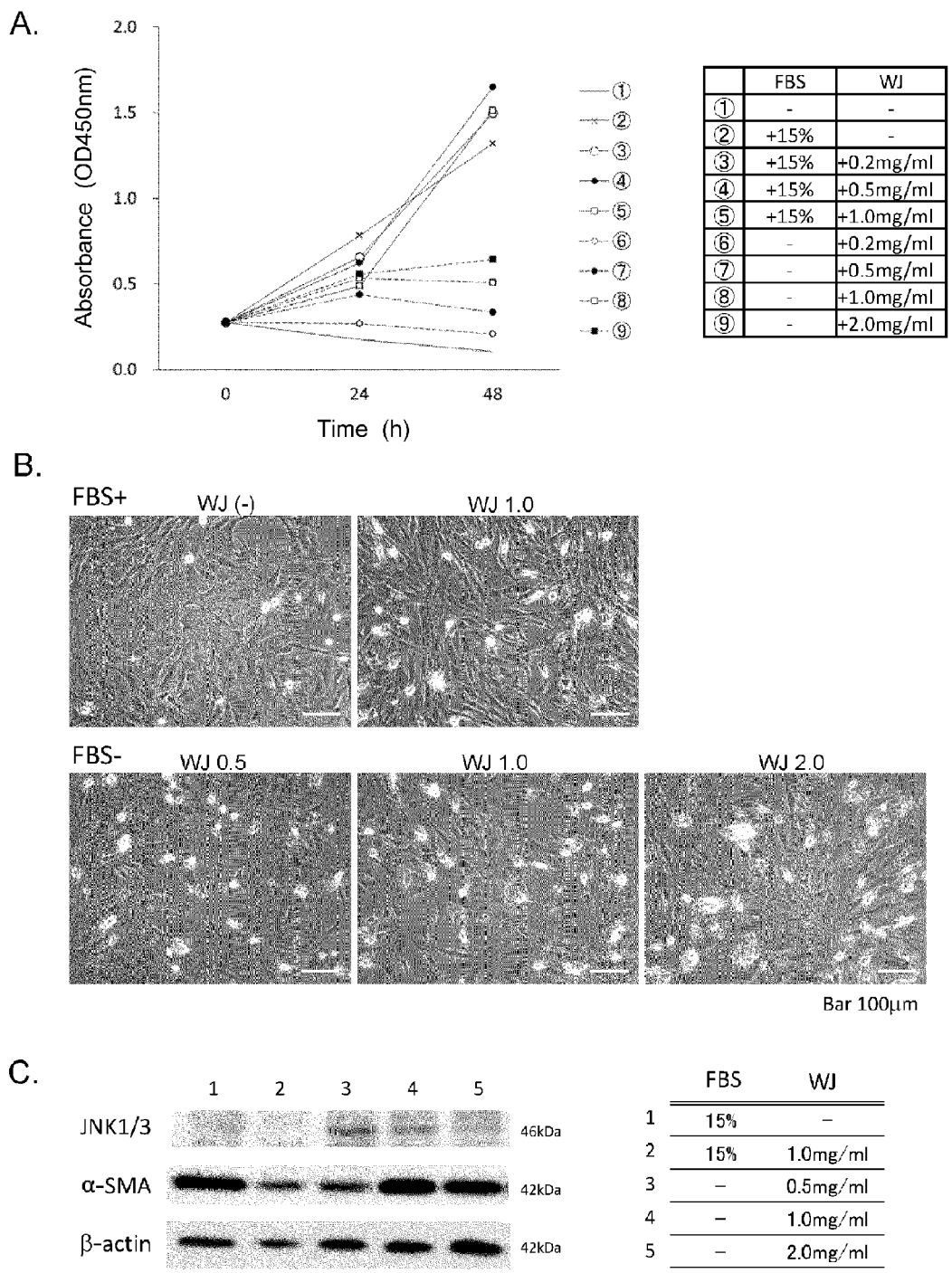
Figure 19:
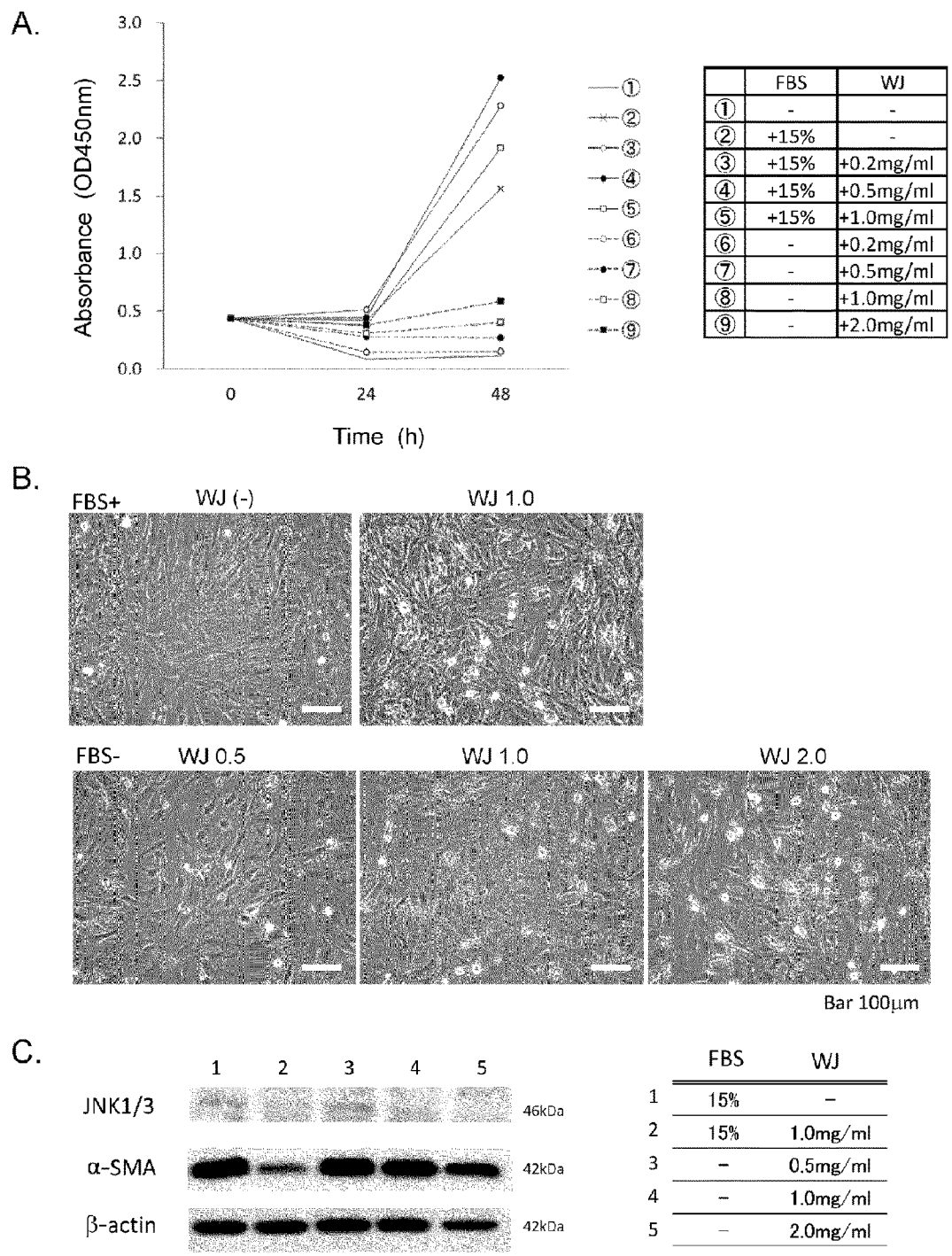

Mesenchymal stem cells of the STZ-administered rats and OLETF rats were cultured in α-MEM without FBS in the same manner as in 4-1., and MTT assay and cell morphology observation were carried out. The results are shown in FIGS. 18 and 19. The cells cultured without FBS and with the extracts showed an extreme decrease in proliferation potency, compared with the cells cultured with FBS and the extracts, and no change was observed in the cell morphology.

As one of the indicators for activation, a change in the expression of JNK1/3 and α-SMA proteins were evaluated. Analysis by Western blotting was performed in the same manner as in 3-3. of Example 3. JNK1/3 was detected using the anti-JNK1/3 antibody (Santa Cruz) and α-SMA was detected using the anti-α-SMA antibody (abcam). As shown in FIGS. 18C and 19C, in the case with FBS and with the extracts, there was a reduction in the amount of JNK1/3 and α-SMA proteins whose expressions in the mesenchymal stem cells from the diabetic rats were increased. However, in the case without FBS, no change in the amount of the proteins was observed or a slight change was observed.

The above results show that the umbilical cord tissue extracts efficiently activate abnormal mesenchymal stem cells in the presence of FBS.

Example 5

Activation of Mesenchymal Stem Cells Separated from Patients with Diabetes

Mesenchymal stem cells were prepared from bone marrow fluid obtained from a patient with type II diabetes (69 years old women, HbA1c value: 6.8%) by the same procedure as Example 3. The resultant cells were used to perform the examination of the concentration of the umbilical cord tissue extracts to be added, and the evaluation of the activation potency in the absence of the serum components in the same manner as in Example 4.

Figure 20:
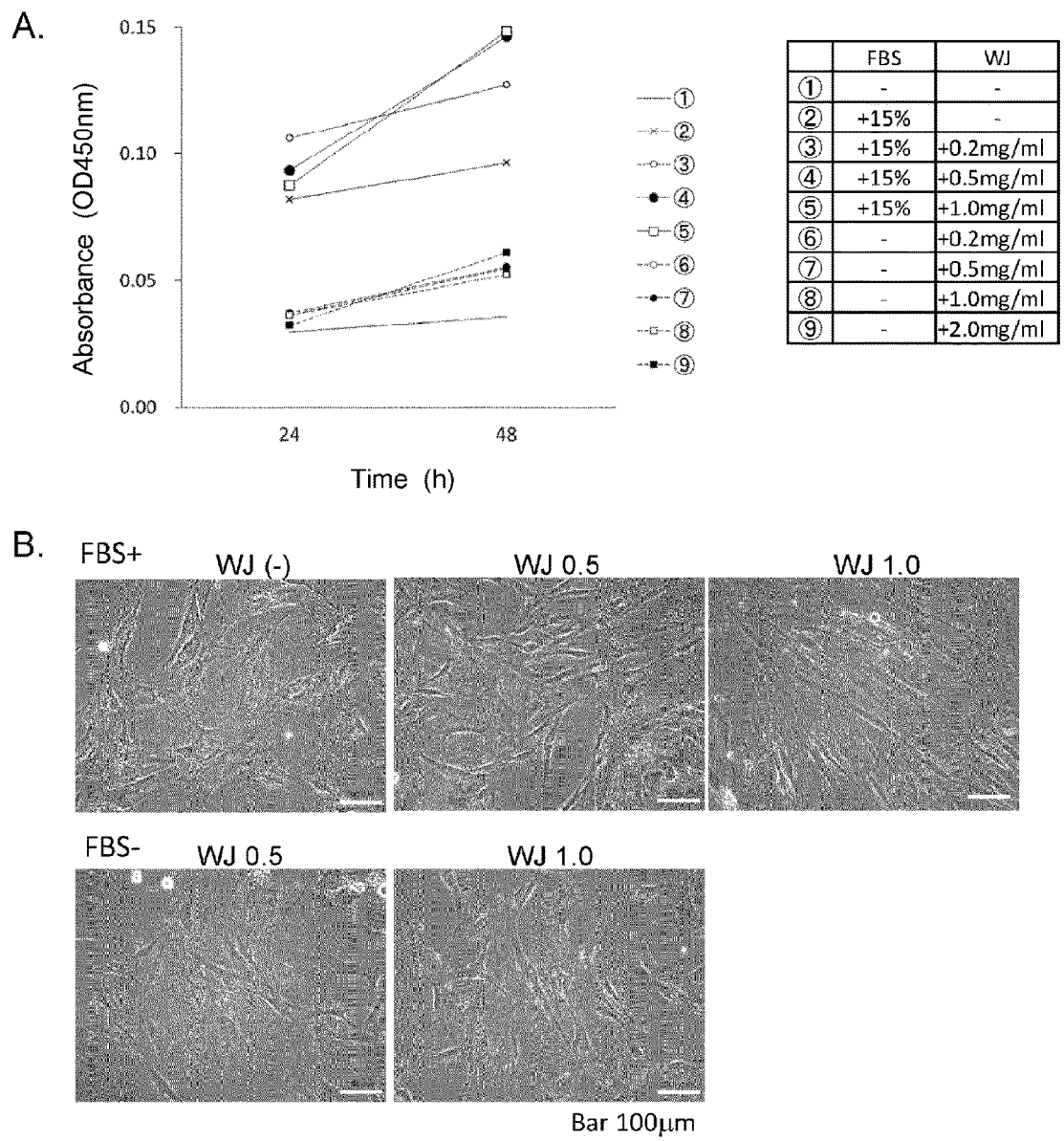

The results are shown in FIG. 20. In the case with FBS, similarly to the mesenchymal stem cells from the diabetic rats, an increase in cellular proliferative potency and a change in the cell morphology were observed in the mesenchymal stem cells from the patient with diabetes when the concentration of the extracts was 0.5 mg/mL or more. However, in the case without FBS, a large change was not observed. FIG. 21 shows changes in total number of cells in the activation treatment with the extracts at a concentration of 0.5 mg/mL in the presence of FBS. In the case with the extracts, the number of the cells significantly increased during the second subculturing.

Figure 22:
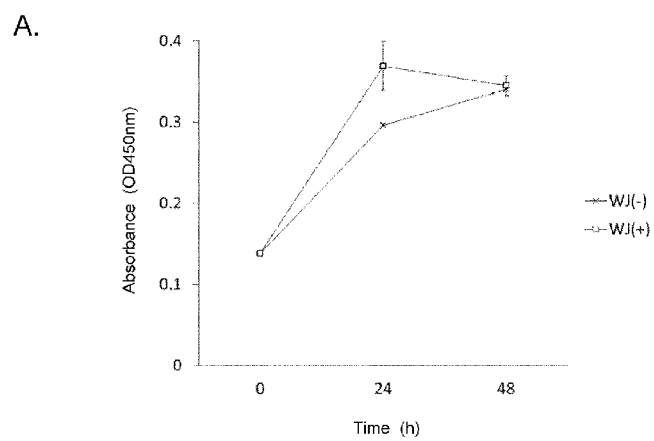
Figure 22:
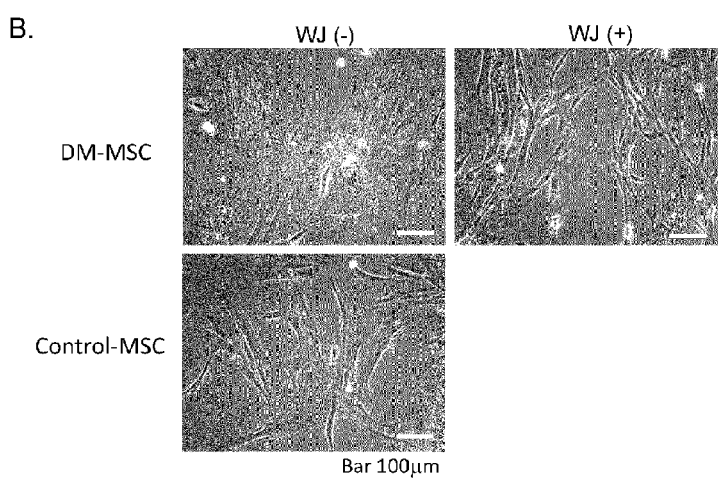

Mesenchymal stem cells from patients with type I diabetes (purchased from DV biologics) were activated with the extracts at a concentration of 1.0 mg/mL in the presence of FBS. The cellular proliferative potency was increased and the cell morphology were changed, similarly to the mesenchymal stem cells from the patient with type II diabetes (FIG. 22).

Example 6

Preparation of Extracts from Placental Tissue and Placental Membrane and Activation of Mesenchymal Stem Cells by Extracts Placentas from human cases (n=2) who underwent the cesarean section were put in sterile bags, and the bags were transferred and stored at 4° C. After being kept frozen (−80° C.) within 24 hours after transfer or directly, i.e. without being frozen, the placentas were separated into each tissues in the following manner and extracts were prepared.

1) The placenta was taken from the sterile bag and unwanted components were rinsed off with physiological saline as much as possible.

2) The placenta was transferred to a flat tray, and separated into a placental membrane and a membrane-peeled maternal placenta tissue.

3) The wet weight of the placental membrane and the maternal placenta tissue were respectively measured.

100 mL of serum free medium (α-MEM) per 50 g (wet weight) was put into a conical tube (225 mL), and the necessary number of tubes was prepared corresponding to the weight.

4) The placental membrane and the maternal placenta tissue were respectively sliced into 5-mm squares using scissors and put into the conical tubes prepared in 3).

5) The conical tubes in 4) were sealed, the opening of each of the tubes was covered with parafilm, and horizontally fixed in a shaker, followed by figure-eight shaking at 80 rpm, at 4° C. for 72 hours.

6) 72 hours later, the conical tubes in 5) were centrifuged at 4° C. at 1000×g for 5 minutes, and supernatants were recovered in new conical tubes.

7) The supernatants recovered in 6) were again centrifuged at 4° C. at 1000×g for 5 minutes and supernatants were recovered, whereby foreign substances such as erythrocyte components and placental tissues were removed.

8) The supernatants recovered in 7) were appropriately dispensed and kept frozen at −80° C. before use.

The average protein concentrations in the resultant placental tissue extract (P) and placental membrane extract (PM) were 9.405 mg/mL and 10.511 mg/mL, respectively. The average protein concentration of the umbilical cord tissue extract obtained from the same donor was 3.074 mg/mL (in all the cases, n=2).

The placental tissue extract (P), the placental membrane extract (PM), and the extract similarly prepared from the whole placental tissue before the separating operation in 2) (P+PM) were used to prepare exosome fractions in the same manner as in 2-4. of Example 2. The expression of HSP70 was analyzed by Western blotting, and the presence of exosomes in all of the extracts was confirmed (FIG. 23).

These extracts were subjected to culture assay in the same manner as in 2-5 of Example 2. After the cultivation, phase-contrast microscope observation was carried out to confirm that there were no cells adhered to culture dishes, namely, the absence of the cells derived from the placental tissue and the placental membrane and having proliferation potency in the extracts (FIG. 24).

The activation potency of each of the placental tissue extracts and the placental membrane extracts on the mesenchymal stem cells from STZ rats was evaluated. Evaluation was performed using the procedure described in the Example 3 except that the placental tissue extract or the placental membrane extract was used at a final concentration of 0.5 mg/mL or 1.0 mg/mL in place of the umbilical cord tissue extract.

FIG. 25A shows the results of MTT assays. The placental tissue extracts and the placental membrane extracts propagated the mesenchymal stem cells from the STZ rats to the extent equivalent to or higher than that of the umbilical cord tissue extracts. FIG. 25B shows phase contrast microscopy images. The mesenchymal stem cells cultured without the extracts were flat polygonal fibroblast-like cells with a few projections, and stress fibers were observed in the cells. When mesenchymal stem cells were cultured with the placental tissue extract or the placental membrane extract, the shape of the mesenchymal stem cells became fusiform, and development of lamellipodia (pseudopodium) was observed. Furthermore, the stress fibers were significantly decreased.

FIG. 25C shows the results obtained by evaluating a change in the expression of JNK1/3 and α-SMA proteins each of which is one of the indicators for activation. In the case of using any of the umbilical cord tissue extracts (Lanes 2 and 3), the placental tissue extracts (Lanes 4 and 5), and the placental membrane extracts (Lanes 6 to 8), there was a reduction in the amount of JNK1/3 and α-SMA proteins whose expressions in the mesenchymal stem cells from the STZ rats were increased. The placental membrane extract (Lane 7) obtained by cutting the placental membrane into thin strip at extraction showed the activity equivalent to that of the placental membrane extract (Lane 8) obtained by mincing the placental membrane.

Example 7

Examination of Activation by Component of Umbilical Cord Tissue Extract

The activation potency of L-Glutamate, hyaluronic acid and exosomes, which are contained in the umbilical cord tissue extract as components, on mesenchymal stem cells was evaluated.

DM-MSCs-WJ (−) obtained in 3-2. of Example 3 were cultured in α-MEM (containing 15% FBS, 1% penicillin and 1% streptomycin) to which the component of Table 3 was added or in α-MEM without the components at 37° C. in an atmosphere of 20% $O_2$ for 48 hours, followed by phase-contrast and electron microscopy observation.

TABLE 3

| Component | Added amount |
| --- | --- |
| L-Glutamate (reagent; L-Glutamine, 200 mM Solution, Gibco) | 5 μL/mL |
| Hyaluronic acid (reagent; Hyaluronic acid Sodium Salt, Wako Pure Chemical Industries) | 400 ng |
| Extract of Example 1 obtained by digesting hyaluronic acid with hyaluronidase (reagent; Hyaluronidase, SIGMA) | Amount at a final concentration of 1.0 mg/mL |

TABLE 3-continued

| Component | Added amount |
| --- | --- |
| Exosome fractions prepared in 2-4. of Example 2 | Amount of exosomes which are derived from the same volume of the extract as that of the extract added in Example 1 |

Figure 26:
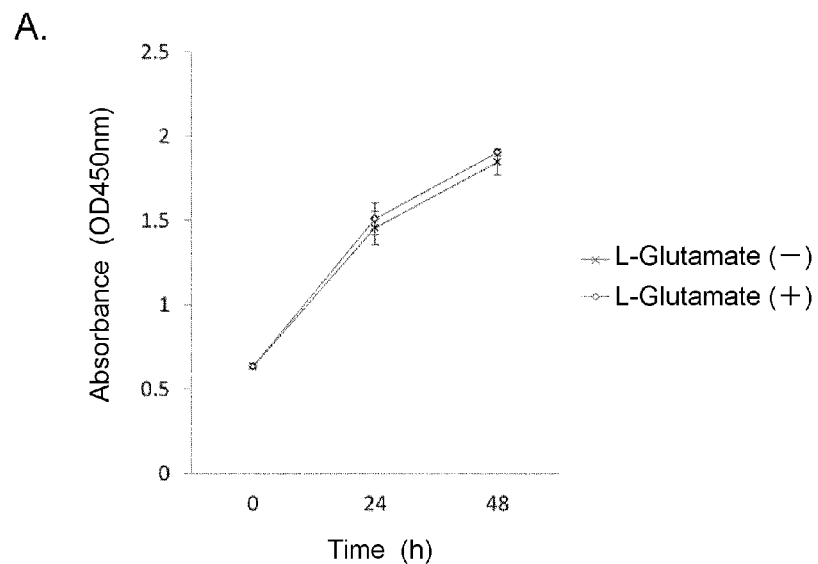
Figure 26:
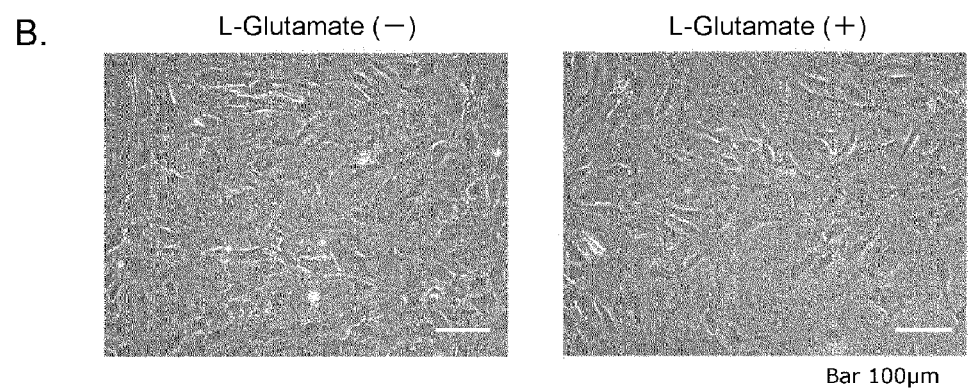
Figure 26:
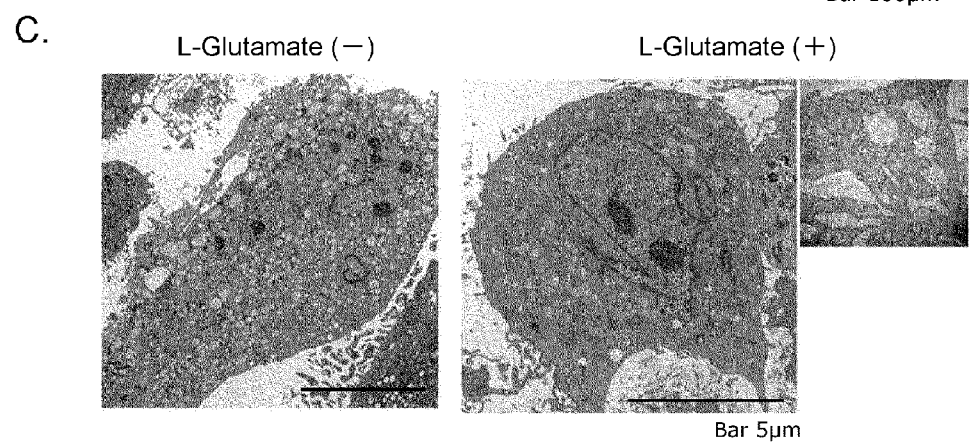
Figure 27:
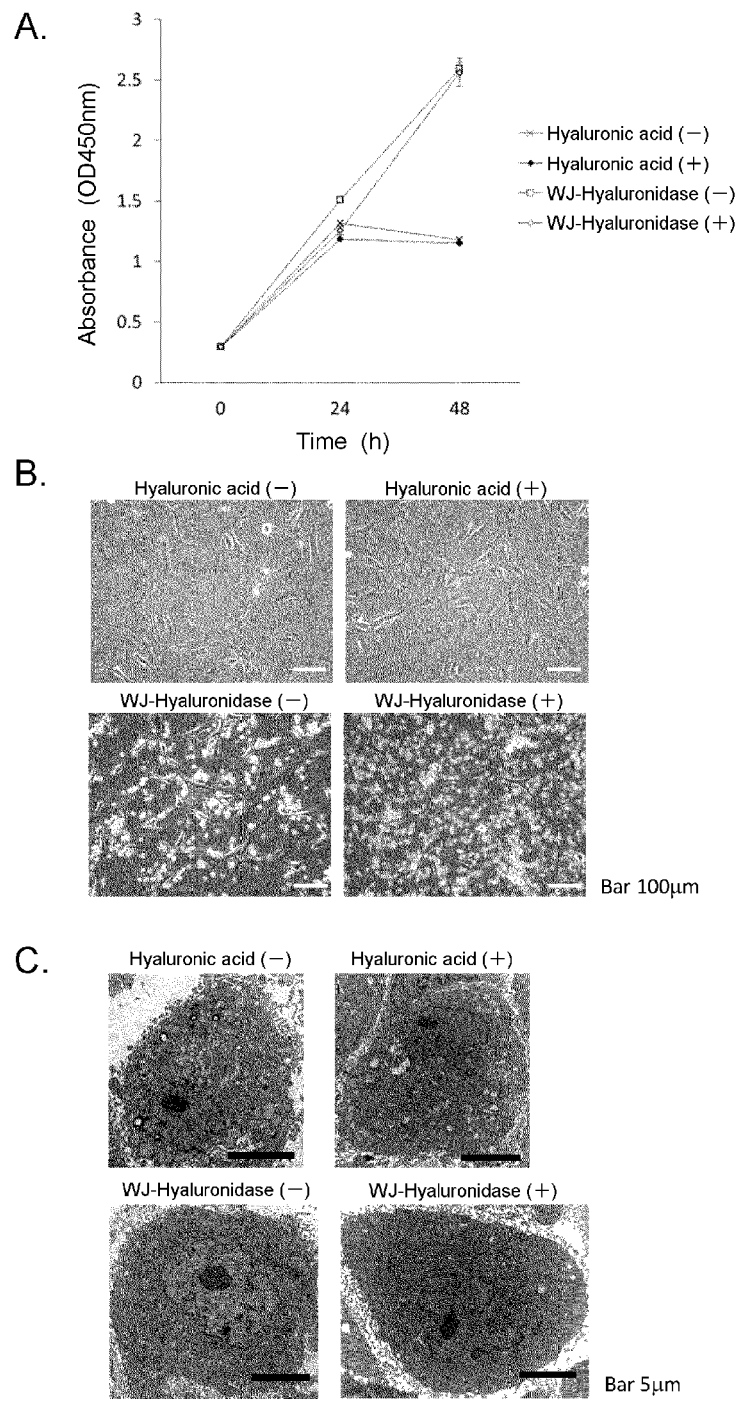
Figure 28:
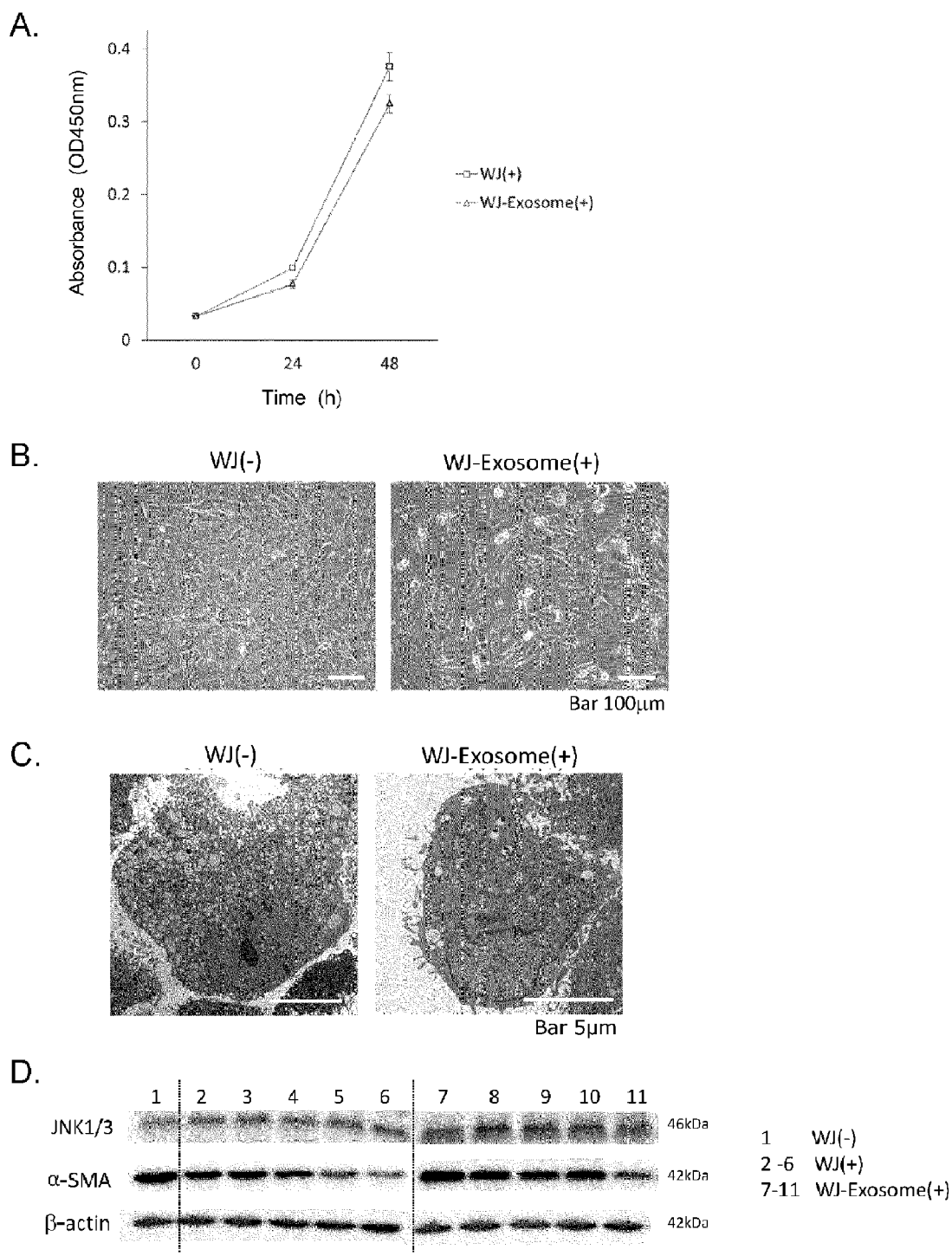

The results are shown in FIGS. 26 to 28. In the case of being cultured in a medium with L-Glutamate or hyaluronic acid, large changes in the proliferation potency and cell morphology of the mesenchymal stem cells were not observed, compared with the case of being cultured in a medium without the above components (FIGS. 26 and 27). In the case of being cultured in a medium with the extract of Example 1 in which hyaluronic acid was digested, the mesenchymal stem cells had high proliferation potency and activated cell morphology, similarly to the case of being cultured in a medium with the extract of Example 1 in which hyaluronic acid was not digested (FIG. 27). Therefore, it is revealed that L-Glutamate or hyaluronic acid alone shows the activation effect on the mesenchymal stem cells not equivalent to the effect of the extract of Example 1, and digestion of hyaluronic acid in the extract of Example 1 does not affect the activation effect on the mesenchymal stem cells.

On the other hand, an increase in proliferation potency was observed in DM-MSCs-WJ (−) cultured in a medium with exosome fractions (FIG. 28A). In addition, the number of projections and the thickness of the cells were increased, and similar cell morphology to the case with the extract of Example 1 was shown (FIG. 28B). Furthermore, the addition of exosome fractions suppressed the expansion of the endoplasmic reticulum (FIG. 28C). A decrease in the expression levels of the JNK1/3 and α-SMA proteins was observed, which was weaker than the case with the extracts of Example 1 (FIG. 28D).

Example 8

Figure 29:
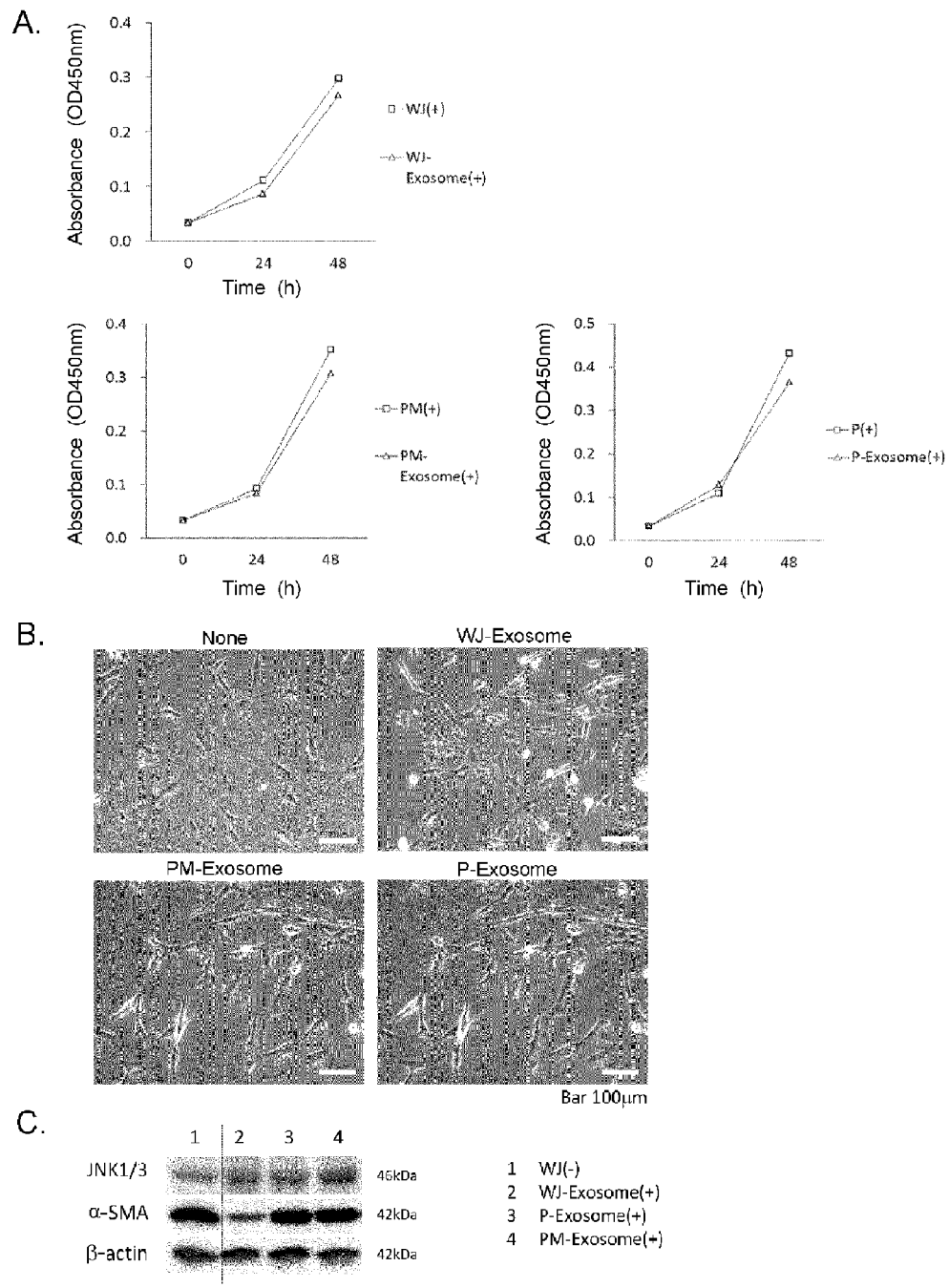

Activation by Exosome Fractions of Placental Tissue Extract and of Placental Membrane Extract The activation of mesenchymal stem cells by exosome fractions of the placental tissue extract and of the placental membrane extract was evaluated in the same manner as in Example 7. The results are shown in FIG. 29. The proliferation potency, the cell morphology and the JNK1/3 and α-SMA expression levels of the mesenchymal stem cells activated by the exosome fractions of the placental tissue extract or of the placental membrane extract had similar tendency to those of the mesenchymal stem cells activated by the exosome fractions of the umbilical cord tissue extract. The results of Examples 7 and 8 indicate that exosome fractions in extracts from fetal appendages are at least one of the components contributing to the activation of mesenchymal stem cells.

Example 9

Therapeutic Effect of Activated Mesenchymal Stem Cells on Diabetic Nephropathy (Mouse Models)

The therapeutic effect of the mesenchymal stem cells (MSCs) activated by the extract of Example 1 was evaluated using diabetic nephropathy model mice.

9-1. Therapeutic Effect of MSCs in which Only Cells (P1) were Subjected to Activation Treatment The used MSCs are as follows:
Control-MSCs and DM-MSCs-WJ (−): cells (P3) obtained in 3-2. of Example 3 were used.
DM-MSCs-WJ (+): the used cells (P3) were obtained by subculturing in the same manner as in 3-2. of Example 3, except that only DM-MSCs (P1) were cultured in a medium with the extract and the subsequent subcultivation was carried out using a medium without the extract (FIG. 30A).

The trial was performed in accordance with the trial plan shown in FIG. 30B. 8-week-old male C57BL/6 mice were administered intraperitoneally with 200 μL of STZ-citrate buffer solution containing STZ in an amount corresponding to 150 mg/kg body weight to produce STZ-induced type I diabetes model mice (STZ mice). Normal group mice were administered with a citrate buffer in place of the STZ solution. 4 weeks after administration, the STZ mice were divided into four groups. In the STZ-Control-MSC group, a single dose of 250 μL of phosphate buffer containing Control-MSCs ($1 \times 10^4$ cells/g (body weight)) was administered into the tail vein. In the STZ-DM-MSC group, a single dose of 250 μL of phosphate buffer containing DM-MSCs-WJ (−) ($1 \times 10^4$ cells/g (body weight)) was administered into the tail vein. In the STZ-DM-MSC-WJ group, a single dose of 250 μL of phosphate buffer containing DM-MSCs-WJ (+) ($1 \times 10^4$ cells/g (body weight)) was administered into the tail vein. In the STZ-Vehicle group, a single dose of 250 μL of phosphate buffer as a vehicle was administered into the tail vein. Every 4 weeks after the administration of the MSCs or the vehicle, the body weight was measured, the blood and the urine were collected. The mice were sacrificed on the 8th week and their kidneys were removed. The blood glucose level was measured using a blood glucose analyzer: Antsense III (HORIBA Medical). Albumin and creatinine in the urine as indicators for kidney function were measured by the turbidimetrical immunoassay and enzymatic method, respectively. Removed kidneys were used for evaluation of organ dysfunction such as microangiopathy.

FIG. 31 shows the body weight change rates when the body weight at the start of administration of the MSCs or the vehicle is set to 1. In the STZ-Vehicle group, a slight body weight decrease was observed compared with the Normal group, whereas in the STZ-Control-MSC group in which Control-MSCs were administered to the diabetic mice, the body weight change was recovered to the extent equivalent to that in the Normal group. In the STZ-DM-MSC group, the body weight was decreased compared with the STZ-Vehicle group, whereas in the STZ-DM-MSC-WJ group, the body weight decrease was suppressed up to the extent equivalent to that in the Normal group or the STZ-Control-MSC group.

FIG. 32 shows the results of blood glucose level. In the STZ-Vehicle group, the blood glucose level was increased compared with the Normal group, whereas in the STZ-Control-MSC group, the increase in blood glucose level was suppressed. The blood glucose level of the STZ-DM-MSC group was higher than that of the STZ-Vehicle group, whereas the blood glucose level of the STZ-DM-MSC-WJ group was gradually increased compared with the STZ-DM-MSC group.

The STZ-Vehicle group showed the highest value of urinary albumin/creatinine ratio (FIG. 33), meanwhile, a decrease with time were observed in the STZ-Control-MSC group. Furthermore, the ratio in the STZ-DM-MSC-WJ group was decreased compared with that in the STZ-DM-MSC group.

9-2. Therapeutic Effect of MSCs in which Cells (P1) to Cells (P3) were Subjected to Activation Treatment Control-MSCs (P3), DM-MSCs-WJ (−) and DM-MSCs-WJ (+) obtained in 3-2. of Example 3 (the activation protocol is shown in FIG. 34A) were used to evaluate the therapeutic effect in the same manner as in 9-1. (FIG. 34B). The results are shown in FIGS. 35 to 37.

The body weight change, blood glucose level and urinary albumin/creatinine ratio showed a tendency similar to or clearer than that of 9-1. A large decrease in the urinary albumin/creatinine ratio was observed in the STZ-Vehicle group and the STZ-DM-MSC group 8 weeks after the administration. This is assumed to be due to hypoproteinemia developed as a result of cachexia in the mice of both groups, which caused less protein excretion to the urine.

Example 10

Therapeutic Effect of Activated Mesenchymal Stem Cells on Diabetic Nephropathy (Rat Models)

The therapeutic effect of MSCs activated by the extract of Example 1 was evaluated using diabetic nephropathy model rats. Unless otherwise described hereinafter, the procedures described in 3-1. and 3-2. of Example 3 and Example 9 were used.

10-1. Therapeutic Effect on Type I Diabetic Nephropathy

Bone marrow cells of male rats with STZ-induced type I diabetes were subcultured twice in a medium without the extract and then subcultured once in a medium without the extract or in a medium with 0.5 mg/mL of the extract. The obtained MSCs (P3) (DM-MSCs-WJ (−) and DM-MSCs-WJ (+), respectively) were used in the following trial (FIG. 38A).

The trial was performed in accordance with the trial plan shown in FIG. 38B. 8-week old male SD rats were administered intravenously with 500 μL of STZ-citrate buffer solution containing STZ in an amount corresponding to 55 mg/kg body weight into the tail vein to produce STZ-induced type I diabetes model rats. 4 weeks after administration, the rats were divided into three groups. In the STZ-DM-MSC group, a single dose of 1000 μL of α-MEM (without containing the serum components and antibiotics) containing DM-MSCs-WJ(−) ($1 \times 10^4$ cells/g (body weight)) was administered into the tail vein. In the STZ-DM-MSC-WJ group, a single dose of 1000 μL of α-MEM containing DM-MSCs-WJ(+) ($1 \times 10^4$ cells/g (body weight)) was administered into the tail vein. In the STZ-Vehicle group, a single dose of 1000 μL of α-MEM as a vehicle was administered into the tail vein. On 0, 1, 4 and 7 weeks after administration of the MSCs or the vehicle, the urine was collected, and albumin and creatinine in the urine were measured.

FIG. 39 shows changes in urinary albumin/creatinine ratio. The urinary albumin/creatinine ratio in the STZ-DM-MSC group changed similarly to that in the STZ-Vehicle group, whereas a decrease was observed in the STZ-DM-MSC-WJ group, suggesting an improvement in kidney function.

10-2. Therapeutic Effect on Type II Diabetic Nephropathy

Bone marrow cells of 6-month-old male OLETF type II diabetes model rats were subcultured twice in a medium without the extract and then subcultured once in a medium without the extract or in a medium with 0.5 mg/mL of the extract to obtain MSCs (P3) (OLETF-DM-MSCs-WJ (−) and OLETF-DM-MSCs-WJ (+), respectively). As control, MSCs (P3) (Control-MSCs) were obtained by subculturing bone marrow cells of normal wild-type rats three times in a medium without the extract (FIG. 40A). These MSCs were used in the following trial.

The trial was performed in accordance with the trial plan shown in FIG. 40B. 6.5-month-old male OLETF rats were divided into four groups. In the OLETF-Control-MSC group, a single dose of 1000 μL of α-MEM containing Control-MSCs ($1\times10^4$ cells/g (body weight)) was administered into the tail vein. In the OLETF-DM-MSC group, a single dose of 1000 μL of α-MEM containing OLETF-DM-MSCs-WJ(−) ($1\times10^4$ cells/g (body weight)) was administered into the tail vein. In the OLETF-DM-MSC-WJ group, a single dose of 1000 μL of α-MEM containing OLETF-DM-MSCs-WJ(+) ($1x\ 10^4$ cells/g (body weight)) was administered into the tail vein. In the OLETF-Vehicle group, a single dose of 1000 μL of α-MEM as a vehicle was administered into the tail vein. On 1, 3 and 6 weeks after administration of the MSCs or the vehicle, the body weight was measured, the blood and the urine were collected. Then, the blood glucose level as well as albumin and creatinine in the urine were measured.

FIG. 41 shows changes in urinary albumin/creatinine ratio. Similarly to the above trials, in the OLETF-Control-MSC group and the OLETF-DM-MSC-WJ group, a decrease in urinary albumin/creatinine ratio, i.e., an improvement in kidney function, was observed.

The results of Examples 9 and 10 indicate that Control-MSCs derived from normal animals have therapeutic effects on diabetes and diabetic nephropathy, meanwhile, DM-MSCs derived from diabetic animals have weak therapeutic effects, or rather have effects of exacerbating these diseases, and the therapeutic effects of DM-MSCs are recovered by the activation treatment using the umbilical cord tissue extract.

Example 11

Activation of Mesenchymal Stem Cells Derived from Rheumatoid Arthritis Model Animals by Umbilical Cord Tissue Extract and Therapeutic Effect of Activated Mesenchymal Stem Cells on Rheumatoid Arthritis 11-1. Collecting of Mesenchymal Stem Cells and Activation Treatment 7- to 9-week old female Lewis rats (Japan SLC) were used to produce rheumatoid arthritis (RA) rats. In sensitization to arthritis, Complete Freund's adjuvant (20 mg/mL of killed tubercle bacillus, Chondrex) and bovine type II collagen solution (2 mg/mL of type II collagen, Chondrex) were mixed in equal amounts to produce an emulsion. The emulsion containing 2 mg of killed tubercle bacillus and 0.2 mg of type II collagens was administered to the tail head of a rat. The emulsion at the same concentration was continuously administered four to five times every 7 to 10 days to develop arthritis.

Development of arthritis was determined based on swelling of the right and left legs, namely, changes in leg volume. A transparent plastic container containing water was placed on an electronic scale (precision: 0.01 g, A&D). The hindleg of the rat was immersed in water up to the depth of the marker line drawn on the top of the leg joint of the rat and allowed to stand. The weight (mg) (mass m, gravity acceleration g) (N) was measured. Since the weight mg is equal to the buoyancy F (N) applied to the leg (F=mg=ρVg), the water density ρ is set to 0.9999 (g/cm$^3$) to calculate the leg volume (cm$^3$). In the case where the total volume of the right and left legs of the rat was 4.5 cm$^3$ or more, the rat was determined to develop arthritis.

The procedures described in 3-1. and 3-2. of Example 3 were used to prepare bone marrow cells from RA rats developing arthritis 6 to 9 weeks after the first emulsion administration or from normal rats. The resultant cells were subcultured twice in a medium without the extract and then subcultured once in a medium without the extract or in a medium with 1.0 mg/mL of the extract of Example 1 (FIG. 43A). The obtained MSCs (P3) (RA-MSCs and RA-MSCs-WJ) were used in the following trials. Furthermore, MSCs (P3) obtained by subculturing bone marrow cells of 7-week-old normal wild-type rats three times in a medium without the extract(Control-MSCs) were used.

11-2. Evaluation of Mesenchymal Stem Cells

In order to confirm the abnormality of mesenchymal stem cells from RA rats, the bone marrow cells ($1\times10^6$ cells) obtained from RA rats or normal rats in 11-1. were separately seeded in 10-cm$^2$ culture dishes and cultured (P0). 10 days later, each of the culture dishes were fixed with methanol, followed by Wright-Giemsa staining. Colonies having a diameter of 2 mm or more were counted. The number of colonies formed was 26 in the case of Control-MSCs (7-week old). The number of colonies formed was 20 in the case of Control-MSCs (12-week old). The number of colonies formed was 3 in the case of RA-MSCs (14-week old). A decrease in colony formation capability was observed in RA-MSCs.

Subsequently, in order to confirm the activation of the mesenchymal stem cells by the extract of the present invention, the proliferation potencies of RA-MSCs (P3) and RA-MSCs-WJ (P3) 48 hours and 72 hours after seeding (24 hours and 48 hours after addition of the extract) were evaluated by MTT assay using the procedure described in 3-3. of Example 3. In both cases of 24 hours and 48 hours after addition of the extract, the proliferation potency of RA-MSCs-WJ was higher than that of RA-MSCs (FIG. 42A).

In addition, MSCs (P3) prepared in the same manner as described above were subjected to morphology observation with a phase-contrast microscope 48 hours after the addition of the extract. As compared with Control-MSCs, the cell body of RA-MSCs was wide and flat and the number of cells was low. In RA-MSCs-WJ, the cell body was narrow like Control-MSCs and a large number of fusiform MSCs were observed (FIG. 42B).

Furthermore, MSCs (P3) were prepared in the same manner as described above except that cells (P2) (2.7 to $3\times10^6$ cells) were seeded in 150-cm$^2$ culture dishes. 48 hours after addition of the extract, cells were detached by trypsin treatment and the total number of cells was measured. The total number of cells was $4.1\times10^6$ cells in the case of Control-MSCs. The total number of cells was $2.6\times10^6$ cells in the case of RA-MSCs. The total number of cells was $6.4\times10^6$ cells in the case of RA-MSCs-WJ. The total cell number of RA-MSCs was lower than that of Control-MSCs, whereas the total cell number of RA-MSCs-WJ was higher than that of RA-MSCs.

11-3. Therapeutic Effect on Rheumatoid Arthritis

Twelve RA rats produced in the same manner as 11-1 and developing arthritis 30 days after the first emulsion administration were divided into four groups (n=3). They were treated as the RA-Vehicle group, the Control-MSC group, the RA-MSC group, and the RA-MSC-WJ group (FIG. 43B). Each of the Control-MSCs, RA-MSCs and RA-MSCs-WJ cultured at P3 ($1\times10$ cells/g (bodyweight)) was suspended in 1 mL of α-MEM and the suspension was administered into the tail vein. In the Vehicle group, 1 mL of α-MEM alone was administered into the tail vein. 6 days after the treatment, the emulsion was administered at a half dose of that used for the first sensitization. Day 0 after treatment was defined as baseline. On day 3, day 5 and day 11 after treatment, swelling of legs was measured. Furthermore, joints of leg (superior, posterior, and tarsal parts) and metatarsal and toe parts (Metatarsophalangeal: MTP joint, Proximal Inter-phalangeal; PIP joint) were visually observed. When swelling and deformation were observed, 0.1 was added in each case. The total was calculated as the joint score. Furthermore, the serum CRP level was measured using the Rat C-Reactive Protein ELISA Kit (eBioscience).

FIG. 44 shows changes in leg volume. On day 3 after treatment, swelling of legs was reduced in the Control-MSC group and the RA-MSC-WJ group. On day 5 and day 11 after treatment, the low level was maintained. On the other hand, changes in swelling of legs were not observed in the RA-MSC group and the RA-Vehicle group. In the RA-MSC-WJ group, swelling was significantly decreased on day 3, day 5 and day 11, compared with day 0 after treatment. Concerning the arthritis score, on day 11 after treatment, arthritis was significantly reduced in the Control-MSC group and the RA-MSC-WJ group, compared with the RA-MSC group (FIG. 45). The CRP level was decreased in the Control-MSC group and the RA-MSC-WJ group on day 11 after treatment (FIG. 46).

The above results indicate that Control-MSCs derived from normal animals have a therapeutic effect on rheumatoid arthritis, meanwhile, RA-MSCs derived from animals with rheumatoid arthritis have no therapeutic effect, and the therapeutic effect of RA-MSCs are recovered by the activation treatment using the umbilical cord tissue extract.

Reference Example 1

Therapeutic Effect of Culture Supernatant of Mesenchymal Stem Cells on Diabetic Nephropathy Concerning Control-MSCs (P3) obtained in 3-2. of Example 3 and the culture supernatant of these MSCs (MSC-CM), the therapeutic effect on diabetic nephropathy was evaluated. The used MSC-CM was obtained by centrifuging a culture solution of the cells (P3).

Reference Example 1-1

Evaluation on STZ-Induced Type I Diabetes Model Mice

Figure 47:
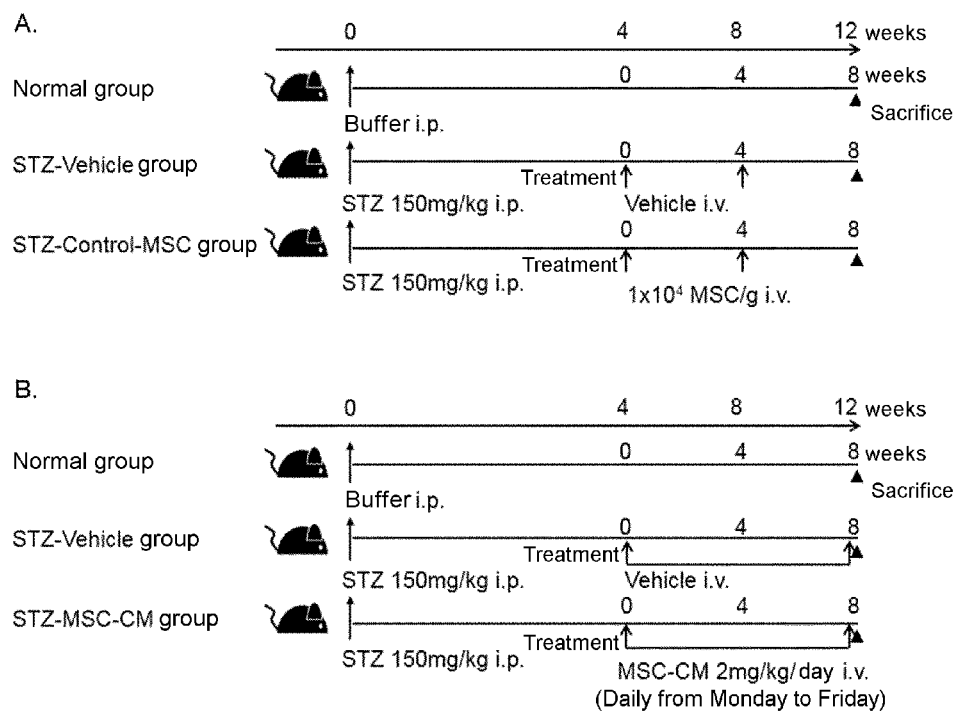

Evaluation trial was performed in accordance with the trial plan shown in FIG. 47. The STZ-administered mice produced in the same manner as in 9-1. of Example 9 were divided into three groups. To the STZ-Control-MSC group, 250 µL of phosphate buffer containing Control-MSCs (1×10 cells/g(bodyweight))) was administered twice every 4 weeks. To the STZ-MSC-CM group, 2 mg/kg (body weight)) of MSC-CM was administered once a day 5 days a week. To the STZ-Vehicle group, 250 µL of phosphate buffer as a vehicle was administered twice every 4 weeks or once a day 5 days a week. This therapeutic trial for 8 weeks was performed and various measurements were carried out in the same manner as in 9-1. of Example 9. Furthermore, tissue sections of the obtained kidneys were produced, and the sections were subjected to PAS staining and Azan staining.

Figure 48:
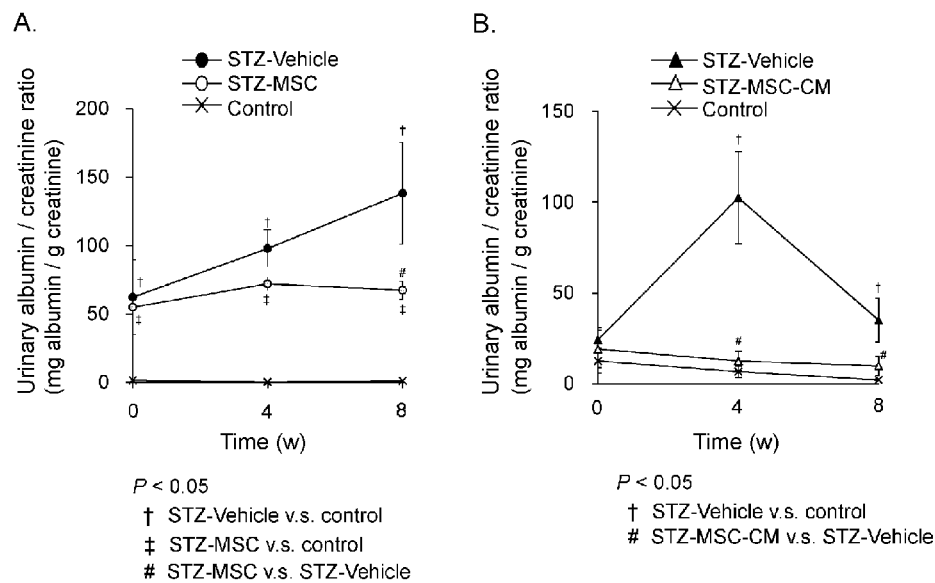

FIG. 48 shows the results of the urinary albumin/creatinine ratio. In the STZ-MSC-CM group, the urinary albumin/creatinine ratio was decreased to the same level as that of the Normal group. FIG. 49 shows microscopy images of stained kidney tissue sections. Expanded glomerular mesangial areas, cellular infiltration, tubulointerstitial inflammatory cell infiltration, and PAS-stain positive degenerated renal tubule were observed in the STZ-Vehicle group, compared with the Normal group. In addition, Azan-stain positive fibril formation was found in the glomerular periphery and tubular interstitium. These changes were suppressed in the STZ-Control-MSC group and the STZ-MSC-CM group.

Reference Examples 1-2

Evaluation on High Fat Diet-Induced Type II Diabetes Model Mice

Figure 50:
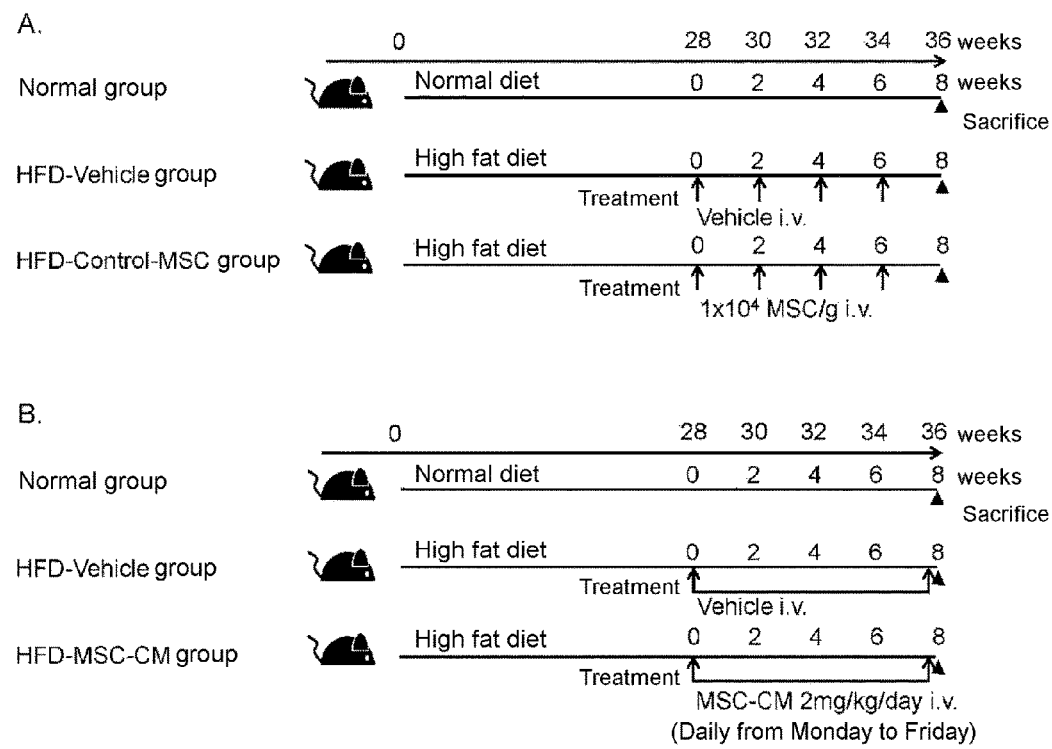

Evaluation trial was performed in accordance with the trial plan shown in FIG. 50. 8-week-old male C57BL/6 mice were fed with a high fat diet containing 60% lard (High-Fat Diet 32, CLEA Japan) to induce diabetes. 28 weeks after the start of feeding, the produced high fat diet-induced type II diabetes model mice were divided into three groups. To the HFD-Control-MSC group, 250 µL of phosphate buffer containing Control-MSCs ($1 \times 10^4$ cells/g (body weight)) was administered four times every 2 weeks. To the HFD-MSC-CM group, 2 mg/kg (body weight)) of MSC-CM was administered once a day 5 days a week. To the HFD-Vehicle group, 250 µL of phosphate buffer as a vehicle was administered four times every 2 weeks or once a day 5 days a week. This therapeutic trial for 8 weeks was performed and various measurements were carried out in the same manner as in 9-1. of Example 9.

FIG. 51 shows the results of the urinary albumin/creatinine ratio. The MSC-CM decreased urinary albumin/creatinine ratio, similarly to the Control-MSCs. FIG. 52 shows microscopy images of stained kidney tissue sections. Hyperplasia of glomerular mesangial matrix, deposition of PAS-stain positive diffusible substances, thickening of glomerular capillary walls and basement membranes, and hyaline degeneration of afferent and efferent arterial walls or arteriolar walls were found in the HFD-Vehicle group, compared with the Normal group. Furthermore, degeneration (ununiformity) of the brush border of proximal tubular epithelium was observed. These changes were reduced in the HFD-Control-MSC group and the HFD-MSC-CM group.

Reference examples 1-1. and 1-2. described above suggest that The MSC-CM has a therapeutic effect on diabetic nephropathy similar to that of the Control-MSCs.

INDUSTRIAL APPLICABILITY

According to the present invention, it is possible to activate an abnormal mesenchymal stem cell whose therapeutic effect is lost or reduced, or rather which has a disease-exacerbating effect. The activated mesenchymal stem cell can be used for the treatment and/or prevention of various diseases.

The invention claimed is:

1. A method for producing activated mesenchymal stem cells in vitro, comprising:
culturing mesenchymal stem cells isolated from an individual having a disease with an effective amount of an extract prepared from a mammalian fetal appendage with an aqueous medium, wherein the disease is selected from the group consisting of diabetes and complications thereof, rheumatoid arthritis and osteoporosis, wherein said extract does not contain cells from the mammal that have proliferation potency,
wherein the expression of a gene is modified in the mesenchymal stem cells, wherein the gene is selected from the group consisting of α-smooth muscle actin (SMA), tumor necrosis factor (TNF)-α, interleukin (IL)-1β, interferon (IFN)-γ, interleukin (IL)-2, Regulated on activation normal T cell expressed and secreted (RANTES), c-Jun N terminal kinase (JNK) 1/3 and insulin-like growth factor (IGF)-1, whereby the activated mesenchymal stem cells are produced.

2. The method according to claim 1, wherein the mammalian fetal appendage is an umbilical cord tissue, a placental tissue or a placental membrane.

3. The method according to claim 1, wherein the mesenchymal stem cells isolated from the individual are bone-marrow-derived mesenchymal stem cells.

4. The method according to claim 1, wherein the disease is diabetes or a complication thereof.

5. The method according to claim 1, wherein the disease is osteoporosis.

6. The method according to claim 1, wherein the disease is rheumatoid arthritis.

7. The method according to claim 1, wherein the mammalian fetal appendage is an umbilical cord tissue.

8. The method according to claim 1, wherein the mammalian fetal appendage is a placental tissue.

9. The method according to claim 1, wherein the mammalian fetal appendage is a placental membrane.

10. The method according to claim 1, wherein after said culturing, the expression of α-SMA, TNF-α, IL-1β, IFN-γ, IL-2, RANTES, or c-JNK 1/3 in the mesenchymal stem cells is decreased.

11. The method according to claim 1, wherein after said culturing, the expression of IGF-1 in the mesenchymal stem cells is increased.

12. The method according to claim 1, wherein the gene is α-SMA.

13. The method according to claim 12, wherein after said culturing, the expression of α-SMA in the mesenchymal stem cells is decreased.

14. The method according to claim 1, wherein the activated mesenchymal stem cells regain a therapeutic effect on treatment of the disease, wherein the disease is diabetes or a complication thereof.

15. The method according to claim 1, wherein the activated mesenchymal stem cells regain a therapeutic effect on treatment of the disease, wherein the disease is rheumatoid arthritis.

16. The method according to claim 1, wherein the activated mesenchymal stem cells regain a therapeutic effect on treatment of the disease, wherein the disease is osteoporosis.

17. The method according to claim 1, further comprising administering an effective amount of the activated mesenchymal stem cells to the individual.

18. The method according to claim 17, wherein the disease is diabetes or a complication thereof.

19. The method according to claim 17, wherein the disease is osteoporosis.

20. The method according to claim 17, wherein the disease is rheumatoid arthritis.

\* \* \* \* \*